(12) United States Patent
Bertozzi et al.

(10) Patent No.: US 10,010,629 B2
(45) Date of Patent: Jul. 3, 2018

(54) COMPOSITIONS AND METHODS FOR IN VIVO IMAGING

(71) Applicant: The Regents of the University of California, Oakland, CA (US)

(72) Inventors: Carolyn Ruth Bertozzi, Stanford, CA (US); Andreas Stahl, El Cerrito, CA (US); Amy Helene Fluitt, San Francisco, CA (US); Elena A. Dubikovskaya, Richmond, CA (US); Allison Cohen, Berkeley, CA (US)

(73) Assignee: The Regents of the University of California, Oakland, CA (US)

(*) Notice: Subject to any disclaimer, the term of this patent is extended or adjusted under 35 U.S.C. 154(b) by 69 days.

(21) Appl. No.: 14/806,207

(22) Filed: Jul. 22, 2015

(65) Prior Publication Data

US 2015/0343094 A1    Dec. 3, 2015

Related U.S. Application Data

(62) Division of application No. 13/695,988, filed as application No. PCT/US2011/036640 on May 16, 2011, now abandoned.

(60) Provisional application No. 61/345,441, filed on May 17, 2010.

(51) Int. Cl.
| | | |
|---|---|---|
| *A61K 49/00* | (2006.01) | |
| *A61K 51/04* | (2006.01) | |
| *C07D 257/02* | (2006.01) | |
| *C07D 277/28* | (2006.01) | |
| *C07D 277/64* | (2006.01) | |
| *C07D 417/04* | (2006.01) | |
| *C07D 487/04* | (2006.01) | |
| *C12Q 1/66* | (2006.01) | |

(52) U.S. Cl.
CPC ...... *A61K 49/0052* (2013.01); *A61K 51/0453* (2013.01); *A61K 51/0482* (2013.01); *C07D 257/02* (2013.01); *C07D 277/28* (2013.01); *C07D 277/64* (2013.01); *C07D 417/04* (2013.01); *C07D 487/04* (2013.01); *C12Q 1/66* (2013.01)

(58) Field of Classification Search
CPC ........ A61K 47/14; A61K 47/48; A61K 51/04; A61K 49/00
See application file for complete search history.

(56) References Cited

U.S. PATENT DOCUMENTS

| | | |
|---|---|---|
| 6,306,993 B1 | 10/2001 | Rothbard et al. |
| 2009/0203879 A1 | 8/2009 | Gengrinovitch |

FOREIGN PATENT DOCUMENTS

| | | | |
|---|---|---|---|
| WO | WO 2008-069824 | | 6/2008 |
| WO | WO-2008069824 | * | 6/2008 |

OTHER PUBLICATIONS

Eiriksdottir, E. et al., "An Improved Synthesis of Releasable Luciferin-CPP Conjugates", Tetrahedron Letters, 2009, vol. 50, Issue 33, pp. 4731-4733.

* cited by examiner

*Primary Examiner* — Michael G Hartley
*Assistant Examiner* — Jagadishwar R Samala
(74) *Attorney, Agent, or Firm* — Bozicevic Field & Francis, LLP; Paula A. Borden; Glenn J. Foulds

(57) ABSTRACT

The present disclosure provides lipid-probe compounds, and compositions comprising the compounds. A subject lipid-probe compound is useful for various imaging applications, which are also provided.

25 Claims, 20 Drawing Sheets

FIG. 18A
FIG. 18B
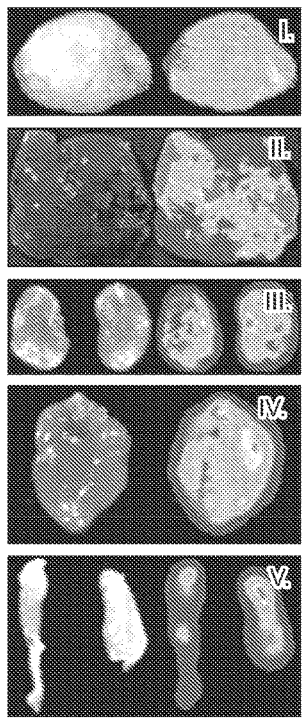
FIG. 18C
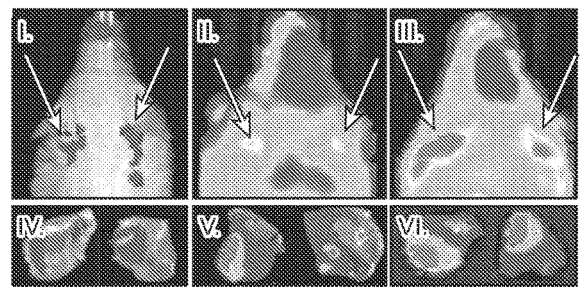
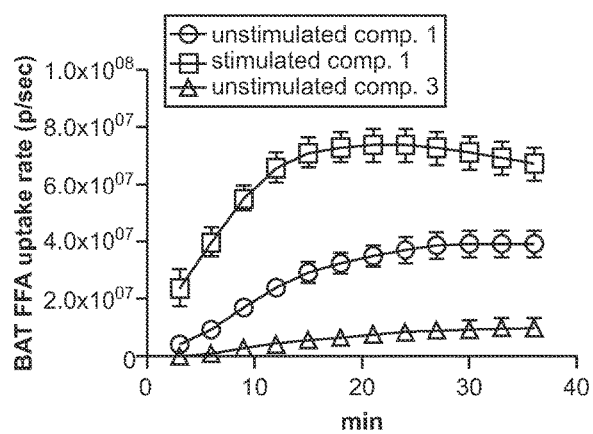
FIG. 18D

ID FFA-luc (compound 1) in poly(ethylene glycol)-
COMPOSITIONS AND METHODS FOR IN VIVO IMAGING

CROSS-REFERENCE

This application is a divisional of U.S. patent application Ser. No. 13/695,988, filed Nov. 2, 2012, which is a U.S. National Phase application under 35 U.S.C. § 371 of International Patent Application No. PCT/US2011/036640, filed May 16, 2011, which claims the benefit of U.S. Provisional Patent Application No. 61/345,441, filed May 17, 2010, each of which applications is incorporated herein by reference in its entirety.

STATEMENT REGARDING FEDERALLY SPONSORED RESEARCH

This invention was made with government support under Grant Nos. GM058867, 2R56DK066336-07, and 5R01KD066336-06, awarded by the National Institutes of Health. The government has certain rights in the invention.

BACKGROUND

Currently, non-invasive imaging approaches for the localization and quantitation of nutrient fluxes rely primarily on the detection of radioisotopes. For example, one approach involves positron emission tomography (PET) utilizing primarily $^{18}$F-labeled glucose analogs (e.g., fludeoxyglucose). There is a need in the art for compositions and methods of in vivo imaging of lipid uptake.

SUMMARY OF THE INVENTION

The present disclosure provides lipid-probe compounds, and compositions comprising the compounds. A subject lipid-probe compound is useful for various imaging applications, which are also provided.

BRIEF DESCRIPTION OF THE DRAWINGS

FIGS. 18A-18D depict the uptake of FFA-luc following injection into mice.

DEFINITIONS

Figure 1:
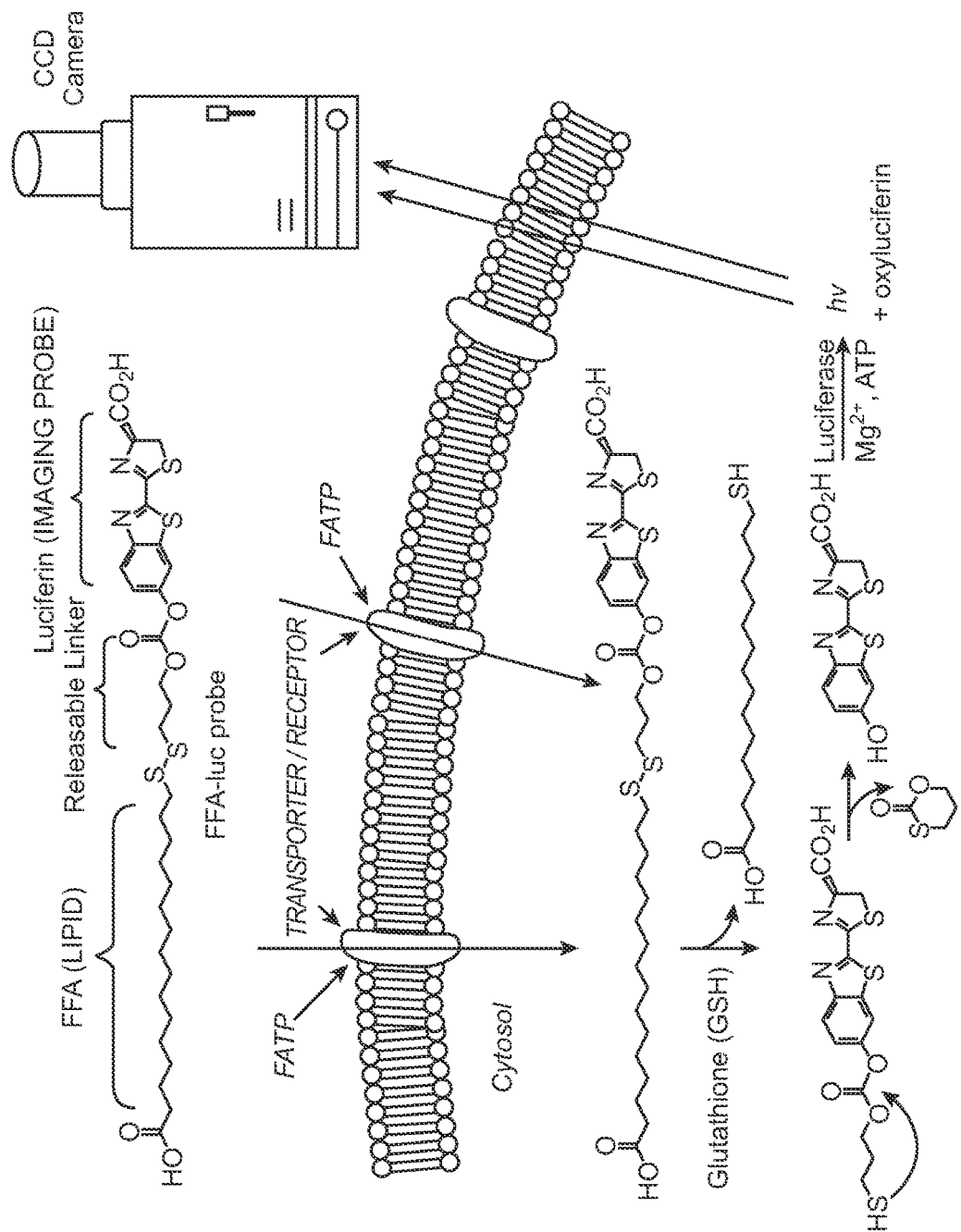
FIG. 1 illustrates a lipid imaging approach as illustrated for a fatty acid (FFA) substrate.

The phrase "in vivo imaging" as used herein refers to methods of detecting the presence of a detectable moiety (e.g., an optically detectable moiety) in a whole, live animal. In vivo imaging may be used to provide two-dimensional as well as three-dimensional (3D) images of an animal. Charge-coupled device cameras, complementary metal oxide semiconductors (CMOS) image sensors, and 3D tomographers can be used to carry out in vivo imaging.

The terms "subject," "individual," "host," and "patient" are used interchangeably herein to a member or members of any multicellular organism, e.g., an animal, including mammalian and non-mammalian species, including human and non-human animals. Subjects and patients thus include, without limitation, humans, non-human primates, canines, felines, ungulates (e.g., equine, bovine, swine (e.g., pig)), avians, rodents (e.g., rats, mice), and other subjects. Non-human animal models, e.g., non-human mammals, e.g. a non-human primate, a murine (e.g., a mouse, a rat), lagomorpha, etc. may be used for experimental investigations.

"Fatty acids" refer to a family of carboxylic acids having a hydrocarbon chain of from about 12 to about 24 carbons in length. Unsaturated fatty acids have at least one carbon-carbon double bond in the hydrocarbon chain. Unsaturated fatty acids include monounsaturated fatty acids (MUFAs) and polyunsaturated fatty acids (PUFAs). Unsaturated fatty acids are designated by the position of the first double bond from the methyl end of the hydrocarbon chain. Omega-3 fatty acids have a first double bond at the third carbon from the methyl end of the chain; and include, e.g., α-linolenic acid (octadeca-9,12,15-trienoic acid), stearidonic acid (octadeca-6,9,12,15-tetraenoic acid), eicosapentaenoic acid (eicosa-5,8,11,14,17-pentaenoic acid; "EPA"), docosapentaenoic acid (docosa-7,10,13,16,19-pentaenoic acid), eicosatetraenoic acid (eicosa-8,11,14,17-tetraenoic acid), and docosahexaenoic acid (docosa-4,7,10,13,16,19-hexaenoic acid; "DHA"). Omega-6 fatty acids have a first double bond at the sixth carbon from the methyl end of the chain; and include, e.g., linoleic acid (9,12-octadecadienoic acid), γ-linolenic acid (6,9,12-octadecatrienoic acid; GLA), eicosadienoic acid (11,14-eicosadienoic acid), dihomo-γ-linolenic acid (8,11,14-eicosatrienoic acid), arachidonic acid (5,8,11,14-eicosatetraenoic acid), docosadienoic acid (13,16-docosadienoic acid), adrenic acid (7,10,13,16-docosatetraenoic acid), docosapentaenoic acid (4,7,10,13,16-docosapentaenoic acid), and calendic acid (8E,10E,12Z-octadecatrienoic acid), and the like. Omega-9 fatty acids have a first double bond at the ninth carbon from the methyl end of the chain; and include, e.g., oleic acid (cis-9-octadecenoic acid); eicosenoic acid (cis-11-eicosenoic acid); mead acid (all-cis-5,8,11-eicosatrienoic acid); erucic acid (cis-13-docosenoic acid); and nervonic acid (cis-15-tetracosenoic acid).

As used herein, "vitamin E" refers to a family of eight molecules having a chromanol ring (chroman ring with an alcoholic hydroxyl group) and a 12-carbon aliphatic side chain containing two methyl groups in the middle and two more methyl groups at the end. The side chain of the tocopherols is saturated, while the side chain of the tocotrienols contain three double-bonds, all of which adjoin a methyl group. The tocopherols and the tocotrienols exist in four isoforms, referred to as alpha, beta, gamma and delta isoforms. The isoforms are named on the basis of the number and position of the methyl groups on the chromanol ring. The alpha form has three methyl groups, the beta and gamma forms have two methyl groups and the delta form has only one methyl group. As used herein, "vitamin E" refers to one or more of α-tocopherol, β-tocopherol, γ-tocopherol, α-tocotrienol, β-tocotrienol, and γ-tocotrienol. "Vitamin E" also includes esters of a vitamin E isoform. For example, "vitamin E" includes esters of a tocopherol, including acetates and succinates.

"Fluorophore" refers to a molecule that, when excited with light having a selected wavelength, emits light of a different wavelength, which may emit light immediately or with a delay after excitation. Fluorophores, include, without limitation, fluorescein dyes, e.g., fluorescein isothiocyanate (FITC), 5-carboxyfluorescein (5-FAM), 6-carboxyfluorescein (6-FAM), 2',4',1,4,-tetrachlorofluorescein (TET), 2',4',5',7',1,4-hexachlorofluorescein (HEX), and 2',7'-dimethoxy-4',5'-dichloro-6-carboxyfluorescein (JOE); cyanine dyes, e.g. Cy3, CY5, Cy5.5, QUASAR™ dyes etc.; dansyl derivatives; rhodamine dyes (TRITC) and derivatives, e.g. 6-carboxytetramethylrhodamine (TAMRA), CAL FLUOR™ dyes, tetrapropano-6-carboxyrhodamine (ROX). BODIPY fluorophores, ALEXA™ dyes, Oregon Green, pyrene, perylene, benzopyrene, squarine dyes, coumarin dyes, CF dyes, DyLight Fluors, the Oyster dyes, the FluoProbes dyes, the Atto dyes, the HiLyte Fluors, luminescent transition metal and lanthanide complexes, and derivatives thereof, and the like. The term fluorophores includes excimers and exciplexes of such dyes.

A "luminescent probe" or "luminophore" refers to a molecule that, when it undergoes a chemical reaction, can convert chemical energy to produce a light emission. A chemiluminescent reaction may include, for example, a chemical or enzymatic reaction. Luminescent probes include, without limitation, a luciferin (e.g., a firefly luciferin); an aminoluciferin; coelenterazine; a coelenterazine analog, a membrane permeant coelenterazine analog, dihydroluciferin; luciferin 6' methylether; luciferin 6' chloroethylether, a red-shifted thermostable luciferase, and a 1,2-dioxetane containing compound.

A "linker" or "linking group" refers to a single bond or a chain of from about 1 to about 20, or from about 20 to about 50, methylene groups in length, for example of about 2, 3, 4, 5, 6, 8, 10, 12, 14, 16, 18 or 20, or from 20 to 50, methylene groups in length, where the methylene backbone is optionally substituted with a sulfur, nitrogen or oxygen heteroatom, which linker may comprise one, two, three, five, seven or more backbone heteroatoms. The bonds between methylenes may be saturated or unsaturated, usually not more than one, two, or three unsaturated bonds will be present in a linker backbone. Each of the backbone atoms may be substituted or unsubstituted, for example with an alkyl, aryl or alkenyl group. A linker may include, without limitations, oligo(ethylene glycol); a polypeptide; ethers, thioethers, tertiary amines, alkyls, which may be straight or branched, e.g., methyl, ethyl, n-propyl, 1-methylethyl (isopropyl), n-butyl, n-pentyl, 1,1-dimethylethyl (t-butyl), and the like; carbamates, carbonates, carbamides (urea-like), esters, thioesters, aryls, amides, imines, phosphate esters, hydrazones, acetals, an orthoester, or combinations thereof.

The term "organic group" and "organic radical" as used herein means any carbon-containing group, including hydrocarbon groups that are classified as an aliphatic group, cyclic group, aromatic group, functionalized derivatives thereof and/or various combinations thereof. The term "aliphatic group" means a saturated or unsaturated linear or branched hydrocarbon group and encompasses alkyl, alkenyl, and alkynyl groups, for example. The term "alkyl group" means a substituted or unsubstituted, saturated linear or branched hydrocarbon group or chain (e.g., $C_1$ to $C_8$) including, for example, methyl, ethyl, isopropyl, tert-butyl, heptyl, isopropyl, n-octyl, dodecyl, octadecyl, amyl, 2-ethylhexyl, and the like. Suitable substituents include carboxy, protected carboxy, amino, protected amino, halo, hydroxy, protected hydroxy, nitro, cyano, monosubstituted amino, protected monosubstituted amino, disubstituted amino, $C_1$ to $C_7$ alkoxy, $C_1$ to $C_7$ acyl, $C_1$ to $C_7$ acyloxy, and the like. The term "substituted alkyl" means the above defined alkyl group substituted from one to three times by a hydroxy, protected hydroxy, amino, protected amino, cyano, halo, trifloromethyl, mono-substituted amino, di-substituted amino, lower alkoxy, lower alkylthio, carboxy, protected carboxy, or a carboxy, amino, and/or hydroxy salt. As used in conjunction with the substituents for the heteroaryl rings, the terms "substituted (cycloalkyl)alkyl" and "substituted cycloalkyl" are as defined below substituted with the same groups as listed for a "substituted alkyl" group. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polycyclic aromatic hydrocarbon group, and may include one or more heteroatoms, and which are further defined below. The term "heterocyclic group" means a closed ring hydrocarbon in which one or more of the atoms in the ring are an element other than carbon (e.g., nitrogen, oxygen, sulfur, etc.), and are further defined below.

"Organic groups" may be functionalized or otherwise comprise additional functionalities associated with the organic group, such as carboxyl, amino, hydroxyl, and the like, which may be protected or unprotected. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ethers, esters, haloalkyls, nitroalkyls, carboxyalkyls, hydroxyalkyls, sulfoalkyls, etc.

The terms "halo" and "halogen" refer to the fluoro, chloro, bromo or iodo groups. There can be one or more halogen, which are the same or different. Halogens of particular interest include chloro and bromo groups.

The term "haloalkyl" refers to an alkyl group as defined above that is substituted by one or more halogen atoms. The halogen atoms may be the same or different. The term "dihaloalkyl" refers to an alkyl group as described above that is substituted by two halo groups, which may be the same or different. The term "trihaloalkyl" refers to an alkyl group as describe above that is substituted by three halo groups, which may be the same or different. The term "perhaloalkyl" refers to a haloalkyl group as defined above wherein each hydrogen atom in the alkyl group has been replaced by a halogen atom. The term "perfluoroalkyl" refers to a haloalkyl group as defined above wherein each hydrogen atom in the alkyl group has been replaced by a fluoro group.

The term "cycloalkyl" means a mono-, bi-, or tricyclic saturated ring that is fully saturated or partially unsaturated. Examples of such a group included cyclopropyl, cyclobutyl, cyclopentyl, cyclohexyl, cycloheptyl, adamantyl, cyclooctyl, cis- or trans decalin, bicyclo[2.2.1]hept-2-ene, cyclohex-1-enyl, cyclopent-1-enyl, 1,4-cyclooctadienyl, and the like.

The term "(cycloalkyl)alkyl" means the above-defined alkyl group substituted for one of the above cycloalkyl rings. Examples of such a group include (cyclohexyl)methyl, 3-(cyclopropyl)-n-propyl, 5-(cyclopentyl)hexyl, 6-(adamantyl)hexyl, and the like.

The term "substituted phenyl" specifies a phenyl group substituted with one or more moieties, and in some instances one, two, or three moieties, chosen from the groups consisting of halogen, hydroxy, protected hydroxy, cyano, nitro, trifluoromethyl, $C_1$ to $C_7$ alkyl, $C_1$ to $C_7$ alkoxy, $C_1$ to $C_7$ acyl, $C_1$ to $C_7$ acyloxy, carboxy, oxycarboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl)carboxamide, protected N—($C_1$ to $C_6$ alkyl)carboxamide, N,N-di($C_1$ to $C_6$ alkyl) carboxamide, trifluoromethyl, N—(($C_1$ to $C_6$ alkyl)sulfonyl) amino, N-(phenylsulfonyl)amino or phenyl, substituted or unsubstituted, such that, for example, a biphenyl or naphthyl group results.

Examples of the term "substituted phenyl" includes a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3, or 4-hydroxyphenyl, 2,4-dihydroxyphenyl, the protected-hydroxy derivatives thereof and the like; a nitrophenyl group such as 2, 3, or 4-nitrophenyl; a cyanophenyl group, for example, 2, 3 or 4-cyanophenyl; a mono- or di(alkyl)phenyl group such as 2, 3, or 4-methylphenyl, 2,4-dimethylphenyl, 2, 3 or 4-(iso-propyl)phenyl, 2, 3, or 4-ethylphenyl, 2, 3 or 4-(n-propyl)phenyl and the like; a mono or di(alkoxy)phenyl group, for example, 2,6-dimethoxyphenyl, 2, 3 or 4-(iso-propoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy) phenyl group such as 2, 3 or 4-carboxyphenyl or 2,4-di (protected carboxy)phenyl; a mono- or di(hydroxymethyl) phenyl or (protected hydroxymethyl)phenyl such as 2, 3 or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl) phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl, and the like.

The term "(substituted phenyl)alkyl" means one of the above substituted phenyl groups attached to one of the above-described alkyl groups. Examples of include such groups as 2-phenyl-1-chloroethyl, 2-(4'-methoxyphenyl) ethyl, 4-(2',6'-dihydroxy phenyl)n-hexyl, 2-(5'-cyano-3'-methoxyphenyl)n-pentyl, 3-(2',6'-dimethylphenyl)n-propyl, 4-chloro-3-aminobenzyl, 6-(4'-methoxyphenyl)-3-carboxy (n-hexyl), 5-(4'-aminomethylphenyl)-3-(aminomethyl)n-pentyl, 5-phenyl-3-oxo-n-pent-1-yl, (4-hydroxynapth-2-yl) methyl and the like.

As noted above, the term "aromatic" or "aryl" refers to six membered carbocyclic rings. Also as noted above, the term "heteroaryl" denotes optionally substituted five-membered or six-membered rings that have 1 to 4 heteroatoms, such as oxygen, sulfur and/or nitrogen atoms, in particular nitrogen, either alone or in conjunction with sulfur or oxygen ring atoms.

Furthermore, the above optionally substituted five-membered or six-membered rings can optionally be fused to an aromatic 5-membered or 6-membered ring system. For example, the rings can be optionally fused to an aromatic 5-membered or 6-membered ring system such as a pyridine or a triazole system, and preferably to a benzene ring.

The following ring systems are examples of the heterocyclic (whether substituted or unsubstituted) radicals denoted by the term "heteroaryl": thienyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl.

Substituents for the above optionally substituted heteroaryl rings are from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, alkyl, substituted alkyl, cycloalkyl, substituted cycloalkyl, (cycloalkyl)alkyl, substituted (cycloalkyl)alkyl, phenyl, substituted phenyl, phenylalkyl, and (substituted phenyl)alkyl. Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl rings, "lower alkoxy" means a $C_1$ to $C_4$ alkoxy group, similarly, "lower alkylthio" means a $C_1$ to $C_4$ alkylthio group.

The term "(monosubstituted)amino" refers to an amino group with one substituent chosen from the group consisting of phenyl, substituted phenyl, alkyl, substituted alkyl, $C_1$ to $C_4$ acyl, $C_2$ to $C_7$ alkenyl, $C_2$ to $C_7$ substituted alkenyl, $C_2$ to $C_7$ alkynyl, $C_7$ to $C_{16}$ alkylaryl, $C_7$ to $C_{16}$ substituted alkylaryl and heteroaryl group. The (monosubstituted) amino can additionally have an amino-protecting group as encompassed by the term "protected (monosubstituted)amino." The term "(disubstituted)amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heteroaryl. The two substituents can be the same or different.

The term "heteroaryl(alkyl)" denotes an alkyl group as defined above, substituted at any position by a heteroaryl group, as above defined.

"Optional" or "optionally" means that the subsequently described event, circumstance, feature, or element may, but need not, occur, and that the description includes instances where the event or circumstance occurs and instances in which it does not. For example, "heterocyclo group optionally mono- or di-substituted with an alkyl group" means that the alkyl may, but need not, be present, and the description includes situations where the heterocyclo group is mono- or disubstituted with an alkyl group and situations where the heterocyclo group is not substituted with the alkyl group.

"Substituted" refers to a group in which one or more hydrogen atoms are independently replaced with the same or different substituent(s). Exemplary substituents include, but are not limited to, alkylenedioxy (such as methylenedioxy), -M, $-R^{60}$, $-O^-$, $=O$, $-OR^{60}$, $-SR^{60}$, $-S^-$, $=S$, $-NR^{60}R^{61}$, $=NR^{60}$, $-CF_3$, $-CN$, $-OCN$, $-SCN$, $-NO$, $-NO_2$, $=N_2$, $-N_3$, $-S(O)_2O^-$, $-S(O)_2OH$, $-S(O)_2R^{60}$, $-OS(O)_2O^-$, $-OS(O)_2R^{60}$, $-P(O)(O^-)_2$, $-P(O)(OR^{60})(O^-)$, $-OP(O)(OR^{60})(OR^{61})$, $-C(O)R^{60}$, $-C(S)R^{60}$, $-C(O)OR^{60}$, $-C(O)NR^{60}R^{61}$, $-C(O)O^-$, $-C(S)OR^{60}$, $-NR^{62}C(O)NR^{60}R^{61}$, $-NR^{62}C(S)NR^{60}R^{61}$, $-NR^{62}C(NR^{63})NR^{60}R^{61}$ and $-C(NR^{62})NR^{60}R^{61}$ where M is halogen; $R^{60}$, $R^{61}$, $R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring.

Compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

A subject compound may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see, e.g., the discussion in Chapter 4 of "Advanced Organic Chemistry", 4th edition J. March, John Wiley and Sons, New York, 1992).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a lipid-probe compound" includes a plurality of such compounds and reference to "the imaging method" includes reference to one or more imaging methods and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides lipid-probe compounds, and compositions comprising the compounds, which compounds are useful in various in vitro and in vivo imaging methods.

Compounds

The present disclosure provides compounds that provide for detection of lipid uptake in a living cell (in vitro or in vivo), e.g., in a living eukaryotic cell in a multicellular organism. A subject compound is referred to herein as a "lipid-probe compound."

A subject lipid-probe compound includes a compound of formula (I):

Q-L-X—Y          (I)

wherein Q is a lipid (e.g., a fatty acid, a glycerolipid, a sterol, an oxisterol, a phospholipid, a sphingolipid, a prenol lipid, and the like);

L is a cleavable linker comprising a cleavable bond that provides for release of Y or X—Y following cleavage of the linker;

X is an optional leaving group (e.g., O, S, or NH); and

Y comprises a detectable moiety that, after release, generates a detectable signal, either directly or through action of another molecule (e.g., after being acted upon by an enzyme). Y is also referred to herein as a "probe."

As noted above, Q is a lipid, e.g., a lipid that is taken up by an active transport mechanism, into a living cell (e.g., a living eukaryotic cell). In formula (I), Q can be selected from an unsaturated fatty acid, a polyunsaturated fatty acid, a saturated fatty acid, an essential fatty acid, a trans fatty acid, a glycerolipid (e.g., a triglyceride, a diglyceride, a monoglyceride), a very long-chain fatty acid, a long-chain fatty acid, a medium-chain fatty acid, a short-chain fatty acid, a free fatty acid, a sterol or oxisterol (e.g., a cholesterol ester, cholesterol, a bile acid, a steroid hormone), a vitamin derived fatty acid (e.g., derived from vitamin E or K), a phospholipid, a sphingolipid, a ganglioside, a prenol lipid (e.g., a carotenoid, vitamin E or K, a ubiquinone). Sterols include, e.g., lanosterols, lumisterols, stigmasterols, sitosterols, mycosterols, ergosterols, cholesterols, and thiocholesterols; as well as esters of same. In certain embodiments, in formula (I), Q is an aliphatic monocarboxylic fatty acid having an aliphatic tail comprising up to 30 C atoms, which acid may be linear or branched, saturated or unsaturated (e.g., a $C_6$ to $C_{14}$ saturated fatty acid). In certain embodiments, in formula (I), Q is selected from lauric acid, palmitic acid, stearic acid, hexanoic acid, decanoic acid, myristic acid, caprylic acid and the like. dicarboxylic fatty acids, particularly from $C_4$ to $C_{10}$ dicarboxylic acids. In certain embodiments, in formula (I), Q is derived from a fatty dicarboxylic acid such as glutaric acid, adipic acid or pimelic acid.

As used herein, the term "cleavable linker" refers to a linker that can be selectively cleaved to produce two products. Application of suitable cleavage conditions to a molecule containing a cleavable linker that is cleaved by the cleavage conditions will produce two byproducts. A cleavable linker of the present invention is stable, e.g. to physiological conditions, until the molecule is contacted with a cleavage-inducing stimulus, such as a cleavage-inducing agent (e.g., an enzyme, an oxidizing agent) or cleavage-inducing conditions (e.g., a reducing environment). The cleavable linker includes a cleavable bond. In some cases, cleavage of the cleavable bond (e.g., a disulfide bond, an ester, an amide, etc.) releases a functional group (e.g., a nucleophilic thiol group, an amino, an alcohol, etc.) that is capable of intramolecularly reacting with a further functional group of the linker (e.g., a carbonate group, an ester, a carbamate, an aryl ether) to release Y or X—Y (e.g., via a cyclization-release reaction). In some cases, cleavage of the cleavable bond provides for spontaneous release of Y or X—Y, e.g., where a cascade occurs in which an electron pair is donated from the site of cleavage through to a leaving group X resulting in cleavage of a second bond and release of X—Y. Exemplary cleavable linkers and conditions are set forth below and are depicted in the exemplary compounds, scheme 2 and FIGS. 1 and 15.

In certain embodiments, in formula (I), the cleavable linker L can be cleaved by an enzyme. In certain embodiments, in formula (I), the cleavable linker L is susceptible to cleavage (e.g., by hydrolysis, by nucleophilic displacement, by oxidation or by reduction) under particular physiological conditions (e.g., reducing conditions, oxidizing conditions, acidic pH or basic pH). In certain embodiments, in formula (I), L comprises a cleavable bond such as a disulfide bond that is susceptible to cleavage under reducing conditions (e.g., cleavage by a sufficient concentration of glutathione). In certain instances, L comprises a peptidase substrate, where the cleavable bond is a scissile amide bond, susceptible to cleavage by the peptidase. In certain embodiments, in formula (I), L comprises a cleavable bond that is susceptible to cleavage (e.g., by hydrolysis) at a particular pH, such as at a pH of 5 or less, 4 or less, 3 or less, or even 2 or less. In certain cases, the cleavable bond is susceptible to cleavage at a pH of 9 or more, 10 or more, 11 or more, or even 12 or more.

In some embodiments, L is a polypeptide that comprises an enzyme cleavage site. In some embodiments, L is a polypeptide that comprises an enzyme cleavage site that is cleaved by an intracellular enzyme. In some embodiments, L is a polypeptide that comprises an enzyme cleavage site that is cleaved by an enzyme present in the cell membrane. In some embodiments, L is a polypeptide that comprises an enzyme cleavage site that is cleaved by an enzyme present in an intracellular organelle.

In some embodiments, L comprises a cleavage site that is cleaved by an esterase (e.g., an intracellular esterase).

In certain embodiments, in formula (I), cleavage of the cleavable bond in linker L directly releases Y. In certain instances, cleavage of the cleavable bond in linker L unmasks a functional group that triggers the release of Y or X—Y. In certain embodiments, upon cleavage of the cleavable bond in linker L, a nucleophilic moiety of the linker is unmasked, that can undergo intramolecular reaction at an electrophilic site adjacent to a leaving group X to trigger the release of X—Y. The cleavable linker L provides for release of Y or X—Y by fragmentation or degradation of the linker.

In certain embodiments, in formula (I), the cleavable linker L can include, but is not limited to, an alkyl, an ether, a carbamate, a carbonate, a carbamide (urea), an ester, a thioester, an aryl, an amide, an imine, a phosphate ester, a hydrazone, an acetal, an orthoester, or combinations thereof. In certain embodiments, in formula (I), the cleavable linker L is described by one of the following structures (where optional leaving group X of formula (I) is also shown in the general structures for clarity and context):

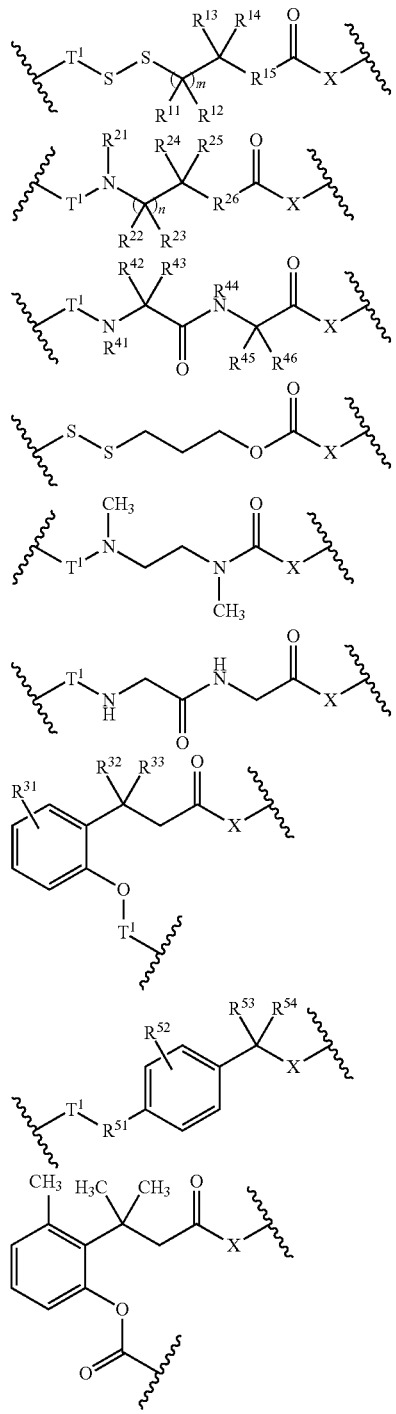

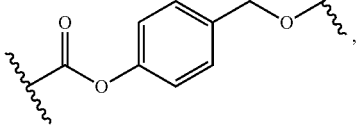

where m and n are independently 1, 2 or 3;

$R^{15}$, $R^{26}$ and $R^{51}$ are independently selected from O, S and NR, where R is hydrogen or alkyl;

$T^1$ is a covalent bond or a linking group, where $T^1$ links the structures to Q;

$R^{31}$ and $R^{52}$ are independently one or more groups, each $R^{31}$ and $R^{52}$ independently selected from H, an alkyl, an aliphatic, an amino, an aryl, an acyl, an alkoxy, an aryloxy, an acyloxy, a carbonyl, a cyano, a halogen, hydroxyl, a heterocyclic group, a nitro, a thio, a sulfinyl, a sulfonyl, and a trifluoromethyl; and $R^{11}$, $R^{12}$, $R^{13}$, $R^{14}$, $R^{21}$, $R^{22}$, $R^{23}$, $R^{24}$, $R^{25}$, $R^{32}$, $R^{33}$, $R^{41}$, $R^{42}$, $R^{43}$, $R^{44}$, $R^{45}$, $R^{46}$, $R^{53}$ and $R^{54}$ are independently selected from hydrogen, an alkyl, an aryl, a heterocyclic group, and an amino acid sidechain group. In some instances, $T^1$-N is a cleavable bond. In some instances, $T^1$-O is a cleavable bond. In some instances, $T^1$-$R^{51}$ is a cleavable bond.

In certain embodiments, the leaving group X may be part of the detectable moiety Y, such that X—Y are combined in a single group. For example, when a luciferin is used, the detectable moiety Y may incorporate the leaving group as part of the detectable moiety.

In formula (I), Y comprises a moiety that is released upon cleavage of the cleavable linker; wherein Y comprises a moiety that, after release, generates a detectable signal, either directly or through action of another molecule (e.g., after being acted upon by an enzyme).

In some embodiments, Y comprises a luminophore such as a luciferin (e.g., a firefly luciferin); an aminoluciferin; coelenterazine; a modified coelenterazine as described in U.S. Pat. No. 7,537,912; a coelenterazine analog as described in U.S. Patent Publication No. 2009/0081129 (e.g., a membrane permeant coelenterazine analog as described in U.S. Patent Publication No. 2009/0081129, e.g., one of Structures II, III, IV, V, and VI of U.S. Patent Publication No. 2009/0081129); aminoluciferin; dihydroluciferin; luciferin 6' methylether; or luciferin 6' chloroethylether. See, e.g., Branchini, B. R. et al. *Anal. Biochem.* 2010, 396, 290-296; and Mezzanotte, L. et al., In vivo bioluminescence imaging of murine xenograft cancer models with a red-shifted thermostable luciferase. *Mol. Imaging Biol.* (2009, Nov. 9, online; PubMed ID: 19937390).

In some embodiments, Y comprises an optionally substituted luciferin moiety, where luciferin moiety is described by one of the following structures:

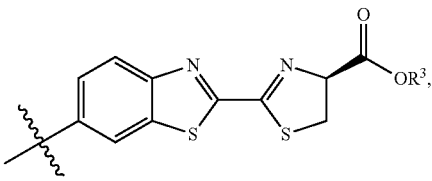

-continued

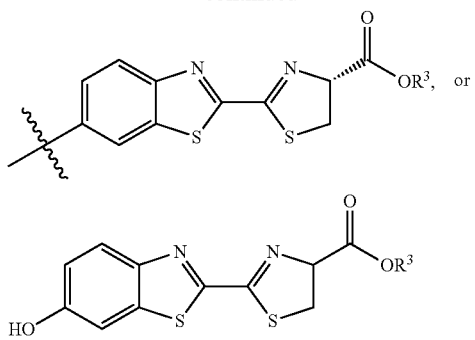

wherein R³ is hydrogen, alkyl or substituted alkyl. The luciferin structure herein is shown with the attachment point to the linker. Depending on the atom at the attachment point, upon cleavage of the linker to release Y, Y can include a luciferin moiety or an aminoluciferin moiety described by one of the following structures:

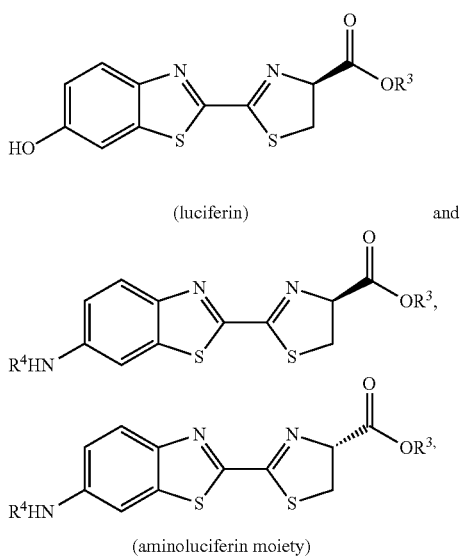

wherein R³ is hydrogen, alkyl or substituted alkyl; and R⁴ is hydrogen, alkyl, substituted alkyl or alkoxy.

In some embodiments, Y comprises an optionally substituted coelenterazine moiety, where coelenterazine has the structure:

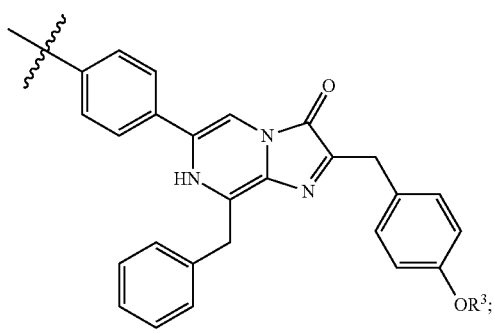

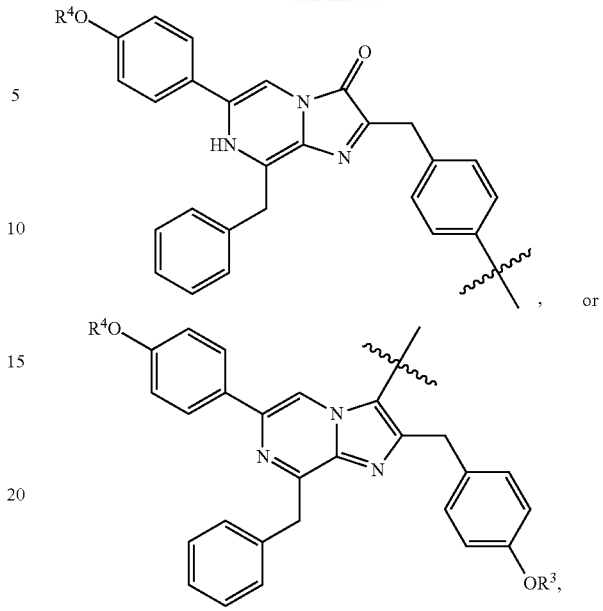

wherein $R^3$ and $R^4$ are each independently selected from hydrogen, acyl, acyloxy, and acylamino. The coelenterazine structures herein are shown with different attachment points to the linker.

In some embodiments, Y comprises a compound of the formula:

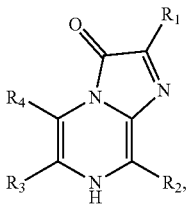

wherein $R^1$, $R^2$, $R^3$, and $R^4$ can be independently H, alkyl, heteroalkyl, aryl, or combinations thereof. The structure can be attached to the linker as a substituent on the core rings or as a substituent on any of $R^1$, $R^2$, $R^3$, and $R^4$. In the above structure, the core ring structure can be optionally substituted. The structure is described in U.S. Pat. No. 7,537,912. In some embodiments, Y comprises a modified coelenterazine as described in U.S. Pat. No. 7,537,912, which is herein incorporated by reference in its entirety.

In some embodiments, Y comprises an optionally substituted membrane-permeant coelenterazine moiety of the formula:

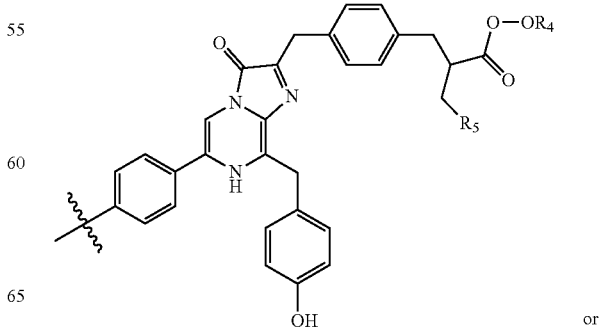

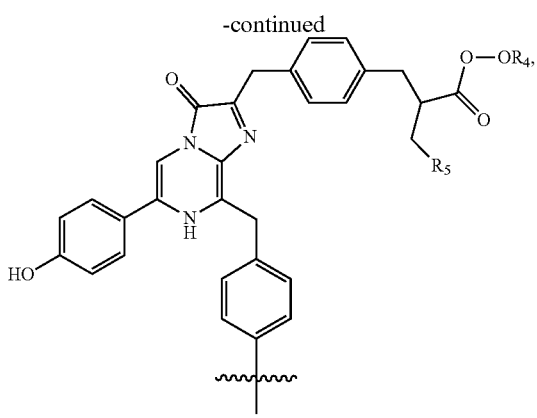

wherein $R_4$ and $R_5$ may independently be alkyl or aralkyl, and $R_4$ may be aryl or optionally substituted aryl, aralkyl or optionally substituted aralkyl, and $R_5$ may be alkyl, optionally substituted alkyl, alkoxy, aralkyl, or optionally substituted aralkyl, aryl, or a heterocycle. The structures herein are shown with attachment points to the linker.

In some embodiments, Y comprises an optionally substituted membrane-permeant coelenterazine moiety of the formula:

wherein p may be an integer ranging from 1 to 20. The structures herein are shown with attachment points to the linker.

In some embodiments, Y comprises an optionally substituted membrane-permeant coelenterazine moiety of the formula:

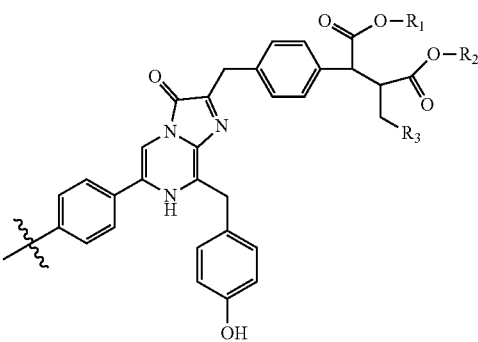

or

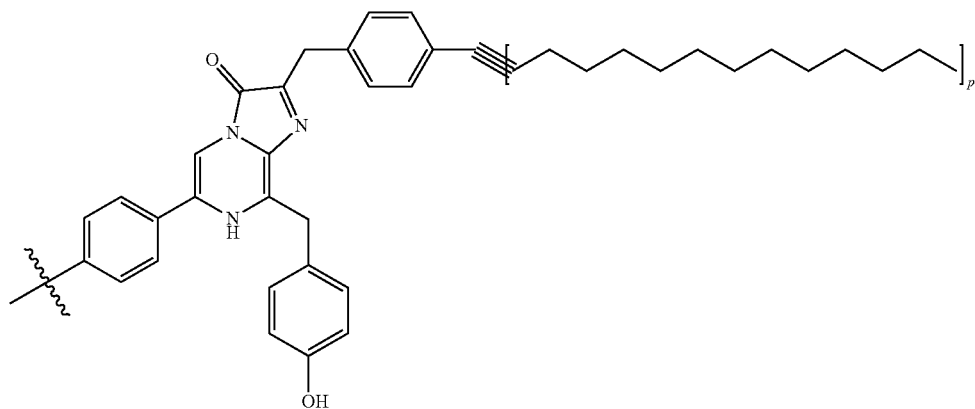

or

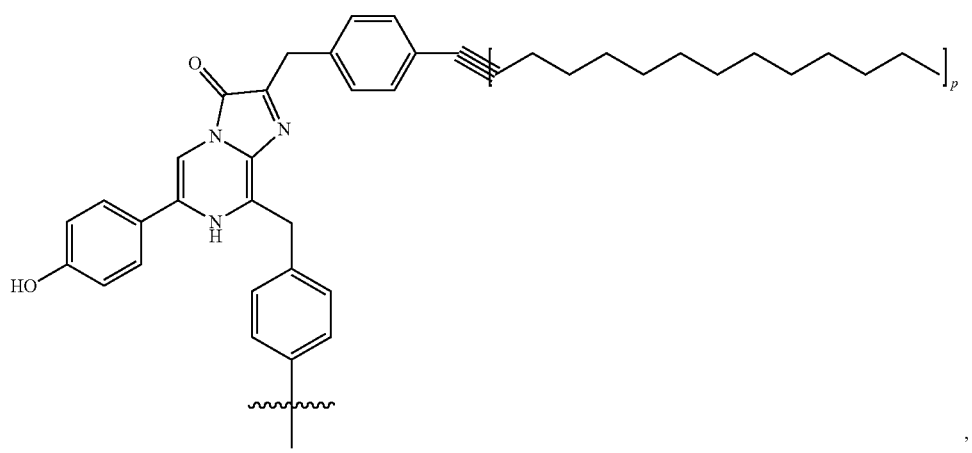

,

-continued

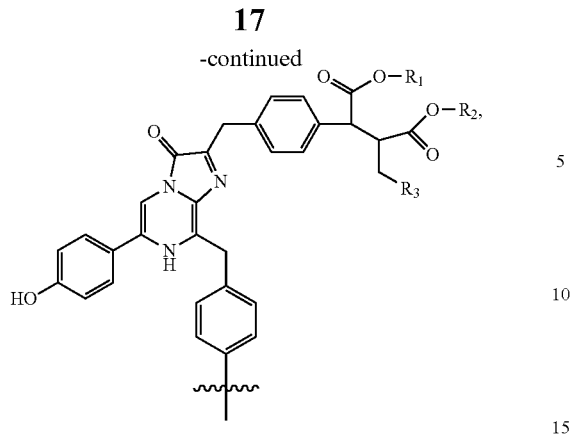

wherein $R_1$, $R_2$, and $R_3$ are independently alkyl, optionally substituted alkyl, alkenyl, or aralkyl. The structures herein are shown with attachment points to the linker.

In some embodiments, Y comprises an optionally substituted membrane-permeant coelenterazine moiety of the formula:

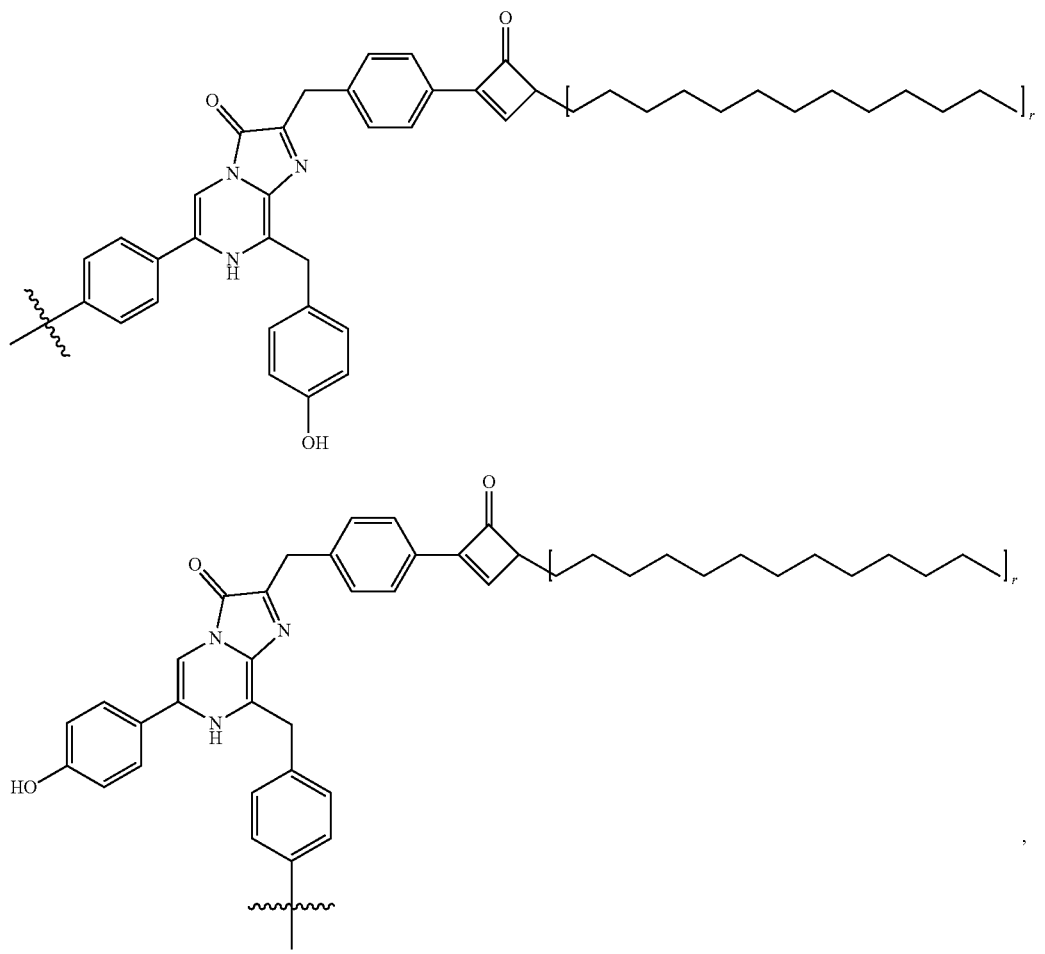

in which r may be an integer from 1 to 20. The structures herein are shown with attachment points to the linker.

In some embodiments, Y comprises an optionally substituted membrane-permeant coelenterazine moiety of the formula:

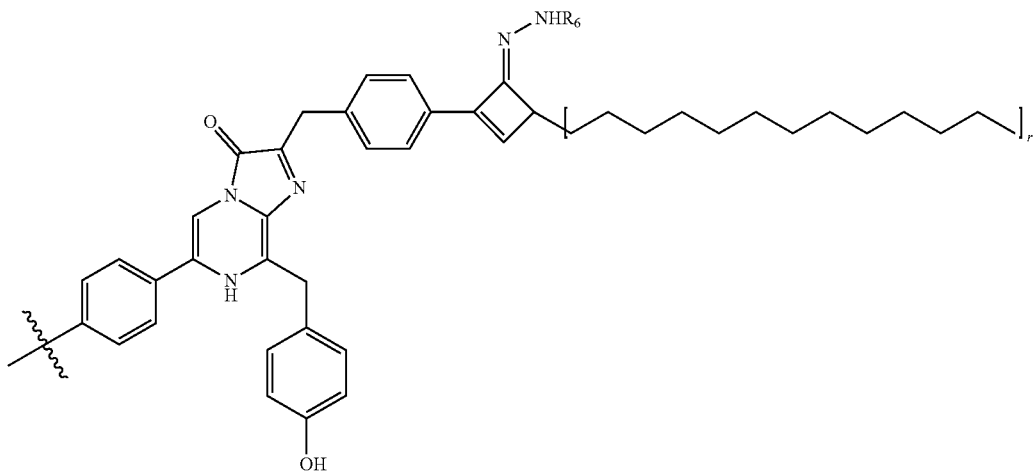

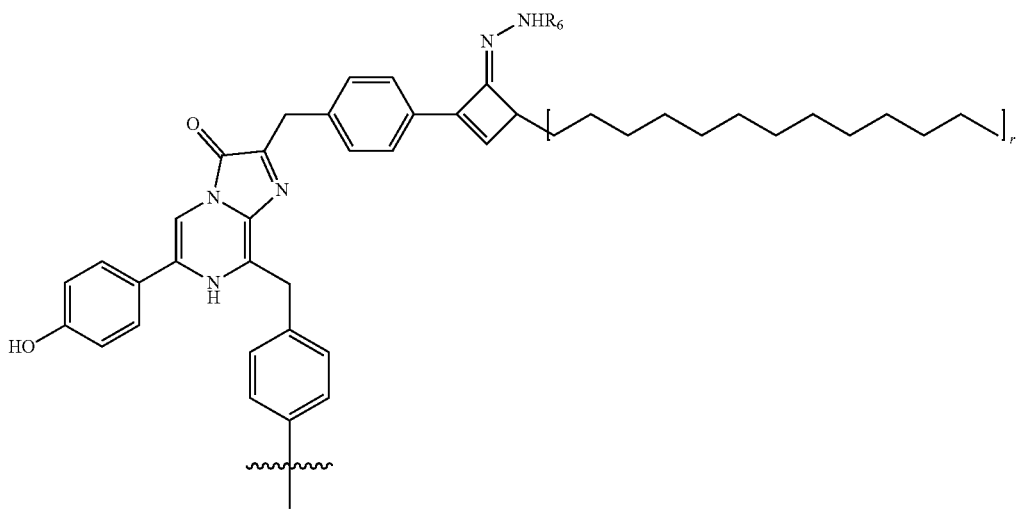

in which r may be an integer from 1 to 20 and R6 may be alkyl, aryl, aralkyl, optionally substituted alkyl, optionally substituted aryl, optionally substituted aralkyl, or alkoxyalkyl. The structures herein are shown with attachment points to the linker.

In some embodiments, Y comprises a moiety of the formula:

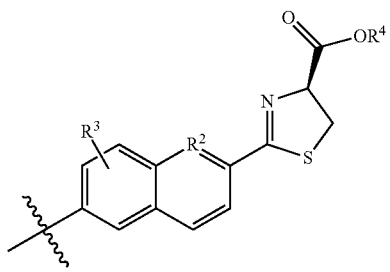

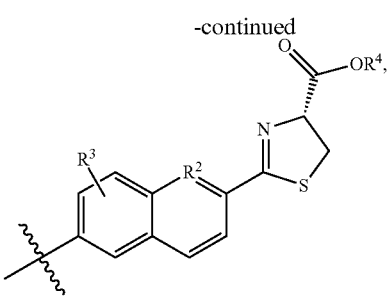

where $R^2$ is N or CH; $R^3$ is hydrogen, halo, hydroxy, alkyl (e.g., methyl), alkoxy, amino, substituted amino (e.g., —NRR'), —CH$_2$N=R, or CH$_2$NRR', where R and R' are each independently selected from hydrogen, alkyl, aryl and heterocycle. The structures herein are shown with attachment points to the linker. In the above structure, the ring structures can be optionally substituted.

In some embodiments, Y comprises a moiety of the formula:

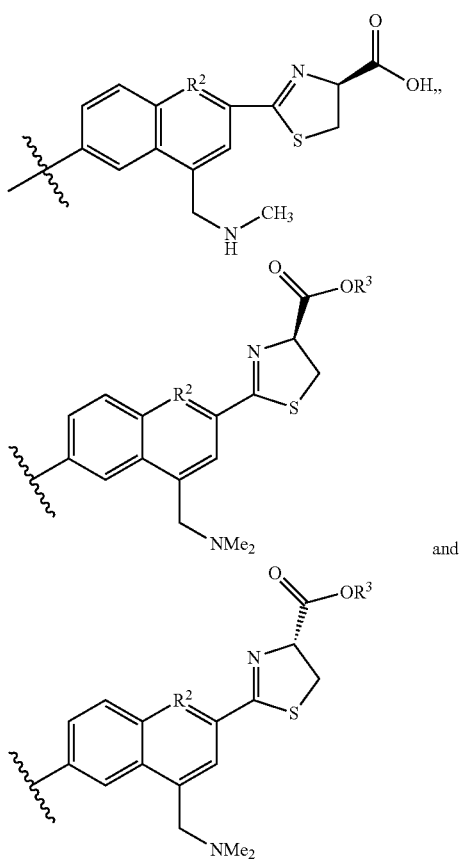

where $R^2$ is N or CH; and $R^3$ is hydrogen, alkyl or substituted alkyl. The structures herein are shown with attachment points to the linker. In the above structure, the ring structures can be optionally substituted.

In some embodiments, Y comprises a moiety of the formula:

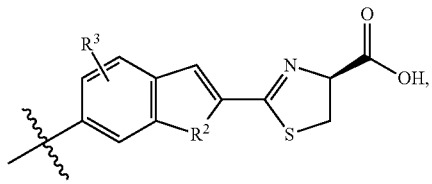

wherein $R^2$ is O or S; $R^3$ is hydrogen, halo, alkyl, alkoxy, amino, substituted amino, —$CH_2N=R$, or $CH_2NRR'$, wherein R is alkyl and R' is alkyl. The structures herein are shown with attachment points to the linker. In the above structure, the ring structures can be optionally substituted.

In some embodiments, Y comprises a moiety of one of the following formulas:

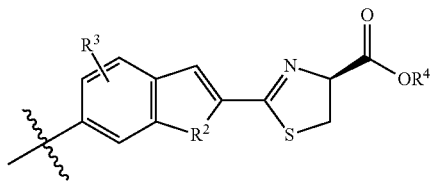

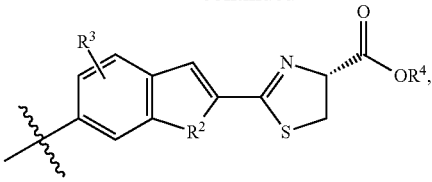

where $R^2$ is O or S; $R^3$ is hydrogen, halo, hydroxyl, alkyl (e.g., methyl), alkoxy, amino, substituted amino (e.g., —NHRR'), —$CH_2N=R$, or $CH_2NRR'$, where R and R' are each independently selected from hydrogen, alkyl, aryl and heterocycle; and $R^4$ is hydrogen, alkyl or substituted alkyl. In the above structure, the ring structures can be optionally substituted.

In some embodiments, Y comprises a moiety of one of the following formulas

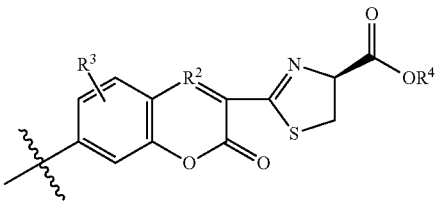

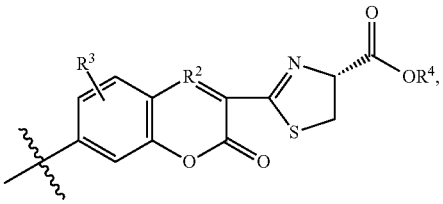

where $R^2$ is N or CH; $R^3$ is hydrogen, halo, hydroxyl, alkyl (e.g., methyl), alkoxy, amino, substituted amino (e.g., —NHRR'), —$CH_2N=R$, or $CH_2NRR'$, wherein R and R' are each independently selected from hydrogen, alkyl, aryl and heterocycle; and $R^4$ is hydrogen, alkyl or substituted alkyl. The structures herein are shown with attachment points to the linker. In the above structure, the ring structures can be optionally substituted.

In some embodiments, Y comprises a contrast agent or a radioisotope, where the contrast agent or radioisotope is one that is suitable for use in imaging, e.g., imaging procedures carried out on humans. Non-limiting examples of labels include radioisotope such as $^{123}$I (iodine), $^{18}$F (fluorine), $^{99}$Tc (technetium), $^{111}$In (indium), and $^{67}$Ga (gallium), and contrast agent such as gadolinium (Gd), dysprosium, and iron. Radioactive Gd isotopes ($^{153}$Gd) also are available and suitable for imaging procedures in non-human mammals. For example, Y can comprise Gd chelates, such as Gd diethylene triamine pentaacetic acid (GdDTPA), Gd tetraazacyclododecanetetraacetic acid (GdDOTA), polylysine-Gd chelates, or derivatives thereof. See, Caravan et al., Chem. Rev. 99:2293-2352 (1999), Lauffer et al., J. Magn. Reson. Imaging, 3:11-16 (1985), and Curtet et al., Invest. Radiol., 33(10):752-761 (1998).

In some embodiments, Y comprises a chelating ligand, such as a chelating ligand of the following structure, or derivatives thereof:

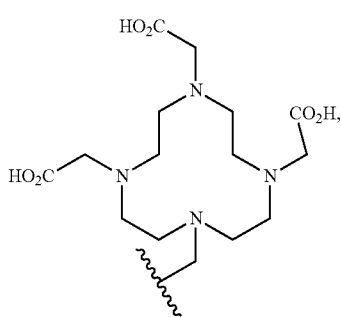 [SMILES: *CN1CCN(CC(=O)O)CCN(CC(=O)O)CCN(CC(=O)O)CC1]

such that Y complexes a gadolinium ion, as shown below:

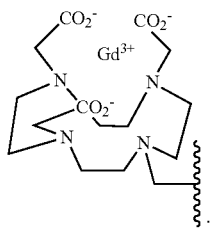

In some embodiments, Y comprises an agent suitable for detection by magnetic resonance imaging (MRI), were agents suitable for detection by MRI include, e.g., paramagnetic or ferromagnetic substances, for example chelated Gd (e.g., Gd-DOTA, Gd-GDTA), and iron oxide nanoparticles.

In certain embodiments, Y comprises a computed tomography (CT), a positron emission tomography (PET), or a single photon emission computed tomography (SPECT) radiotracer that could be any compounds containing carbon-11, nitrogen-13, oxygen-15, fluorine-18, and rubidium-82 radionuclides incorporated into water, glucose, ammonia, or any other synthetic molecule. In some embodiments Y contains radioisotope such as $^{123}$I (iodine), $^{99}$Tc (technetium), $^{111}$In (indium), and $^{67}$Ga (gallium). Suitable PET/SPECT contrast agents include, e.g., a positron emitter, for example $^{11}$C, $^{13}$N, $^{18}$F, $^{82}$Ru, and $^{15}$O. Iodinated CT contrast agents can be used.

Figure 14:
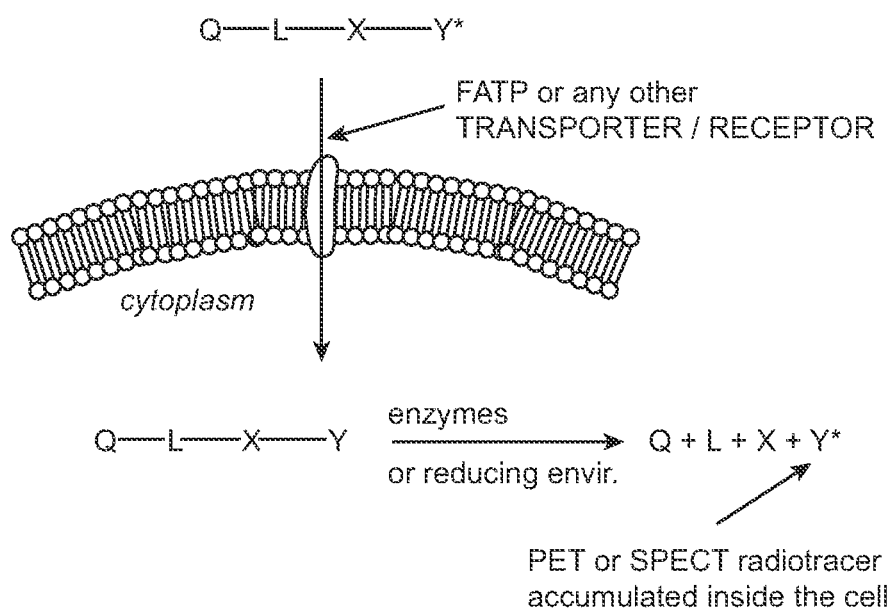
FIG. 14 depicts an example of the use of a PET/SPECT contrast agent in a subject lipid-probe compound.

In certain embodiments where Y comprises a CT, PET, or SPECT radiotracer the probe can work via the mechanism depicted in FIG. 14.

Figure 15:
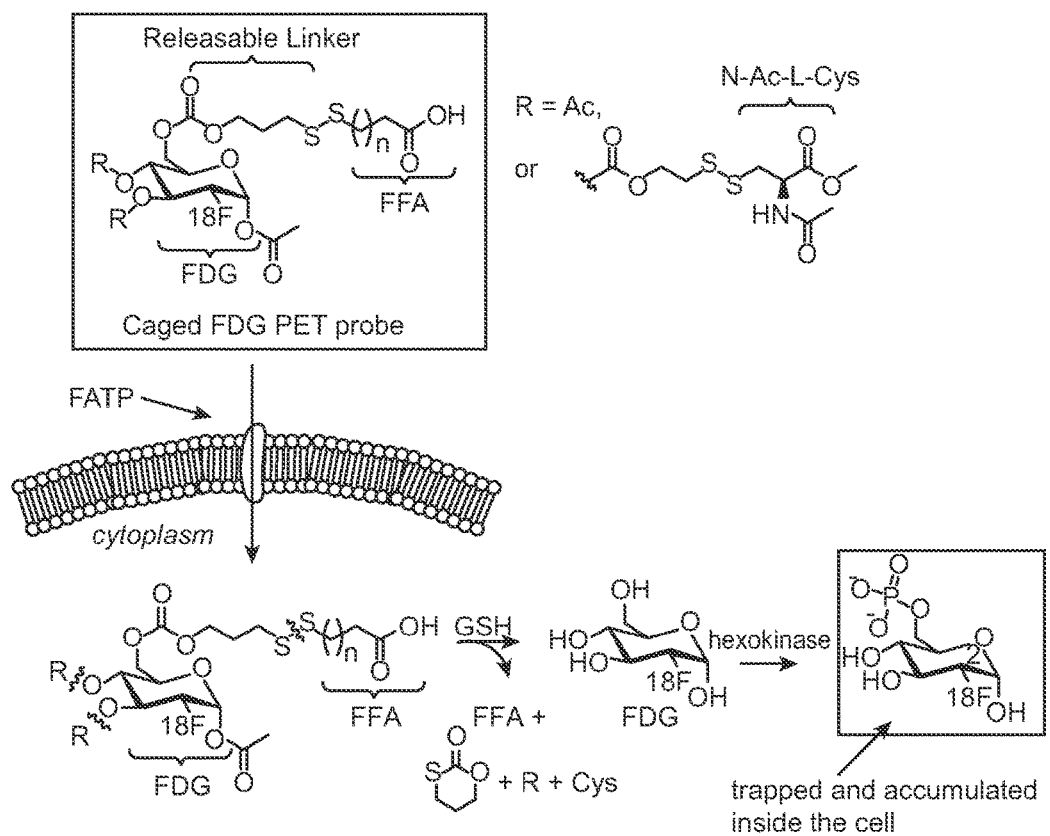
FIG. 15 depicts an example of the use of a caged FDG contrast agent in a subject lipid-probe compound.

As an example, Y* can be a caged fludeoxyglucose (FDG) derivative as shown in FIG. 15. Upon internalization inside the cell, the caging groups will fall off and FDG will be trapped and accumulated inside the cells based on its usual mechanism.

In certain embodiments, Y comprises a fluorophore, which fluorophore can be any molecule that is fluorescent (a molecule that absorbs energy of a specific wavelength and re-emits energy at a different wavelength). Specific examples may include: a derivatives of rhodamine (TRITC), a derivative of fluorescein, coumarins, cyanine, DyLight Fluors, CF dyes, the DyLight Fluors, the Oyster dyes, the FluoProbes dyes, the Atto dyes, the Alexa Fluors, the HiLyte Fluors, and others.

In some embodiments, Y is a fluorescent protein. Suitable fluorescent proteins include, e.g., a green fluorescent protein (GFP), e.g., a GFP from *Aequoria victoria* or a mutant or derivative thereof, as described in U.S. Pat. Nos. 6,066,476; 6,020,192; 5,985,577; 5,976,796; 5,968,750; 5,968,738; 5,958,713; 5,919,445; 5,874,304; a red fluorescent protein; a yellow fluorescent protein; any of a variety of fluorescent and colored proteins from Anthozoan species, as described in, e.g., Matz et al. (1999) *Nature Biotechnol.* 17:969-973; and the like.

In certain embodiments, in formula (I), L is $T^1$-Z-$T^2$ such that the compound is of formula (II):

$$Q\text{-}T^1\text{-}Z\text{-}T^2\text{-}X\text{—}Y \qquad (II)$$

where Q, X and Y are as defined above;

$T^1$ and $T^2$ are independently a covalent bond or a linking group; and

Z comprises a cleavable bond that, after cleavage, unmasks a functional group that provides for release of Y or X—Y, and generation of a detectable signal.

In certain embodiments, in formula (II), $T^2$ comprises an electrophilic center adjacent to X, and the functional group is a nucleophilic group that reacts intramolecularly at the electrophilic center to release X—Y. In certain instances, the cleavable bond is part of the $T^1$-$Z^1$-$T^2$ backbone, such that unmasking the functional group leads to cleavage of $T^1$-Z-$T^2$. In certain instances, the cleavable bond is not part of the $T^1$-$Z^1$-$T^2$ backbone but rather is part of a backbone substituent, such that unmasking the functional group does not cleave $T^1$-$Z^1$-$T^2$.

In certain embodiments, in formula (II), cleavage of the cleavable bond unmasks a functional group that leads to spontaneous release of X—Y, via electron pair donation.

In certain embodiments, in formula (II), T1-Z comprises a peptide substrate for an enzyme (e.g., a peptidase such as trypsin) that provides for enzyme catalyzed cleavage of the cleavable bond.

In certain embodiments, a subject lipid-probe compound is of the structure of formula (III):

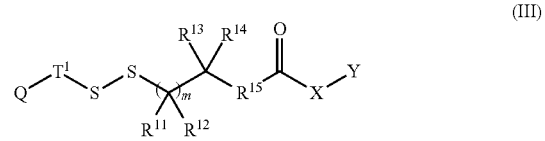

where Q, X, $T^1$ and Y are as defined above;

m is 1, 2 or 3;

$R^{15}$ is selected from O, S and NH; and $R^{11}$, $R^{12}$, $R^{13}$ and $R^{14}$ are independently selected from hydrogen, an alkyl, an aryl and a heterocyclic group.

In certain embodiments, in formula (III), m is 2; $R^{11}$, $R^{12}$, $R^{13}$ and $R^{14}$ are hydrogen; $R^{15}$ is O; and $T^1$ is a single bond connecting Q and S. In certain embodiments, in formula (III), Q is a saturated fatty acid comprising 20 carbons or less; and X—Y is luciferin.

In certain embodiments, a subject lipid-probe compound is of the structure of formula (IV):

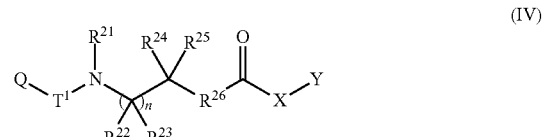

where Q, X, $T^1$ and Y are as defined above;

n is 1, 2 or 3;

$R^{26}$ is selected from O, S and NH; and $R^{21}$, $R^{22}$, $R^{23}$, $R^{24}$ and $R^{25}$ are independently selected from hydrogen, an alkyl, an aryl and a heterocycle.

In certain embodiments, in formula (IV), n is 1; $R^{21}$ is methyl; $R^{22}$, $R^{23}$, $R^{24}$ and $R^{25}$ are hydrogen; and $R^{26}$ is O or $NCH_3$. In certain embodiments, in formula (IV), Q is a saturated fatty acid comprising 20 carbons or less; and X—Y is luciferin.

In certain embodiments, a subject lipid-probe compound is of the structure of formula (V):

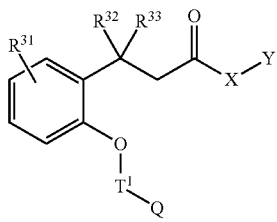

where Q, X, $T^1$ and Y are as defined above;
$R^{31}$ is one or more groups, each $R^{31}$ independently selected from H, an alkyl, an aliphatic, an amino, an aryl, an acyl, an alkoxy, an aryloxy, an acyloxy, a carbonyl, a cyano, a halogen, hydroxyl, a heterocyclic group, a nitro, a thio, a sulfinyl, a sulfonyl, and a trifluoromethyl; and
$R^{32}$ and $R^{33}$ are independently selected from hydrogen, an alkyl, an aryl and a heterocycle.

In certain embodiments, in formula (V), $R^{31}$, $R^{32}$ and $R^{33}$ are hydrogen. In certain embodiments, in formula (V), Q is a saturated fatty acid comprising 20 carbons or less; and X—Y is luciferin.

In certain embodiments, a subject lipid-probe compound is of the structure of formula (VI):

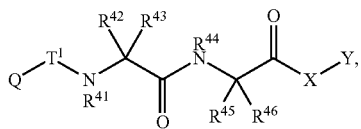

where Q, X, $T^1$ and Y are as defined above;
$R^{41}$ and $R^{44}$ are independently selected from hydrogen, an alkyl, an aryl and a heterocycle; and
$R^{42}$, $R^{43}$, $R^{45}$ and $R^{46}$ independently selected from hydrogen an alkyl, an aryl a heterocyclic group and an amino acid sidechain. In certain instances, at least one of $R^{42}$ and $R^{43}$ are H, and at least one of $R^{45}$ and $R^{46}$ are H.

In certain embodiments, in formula (VI), $R^{41}$ and $R^{44}$ are hydrogen; and $R^{42}$, $R^{43}$, $R^{45}$ and $R^{46}$ are independently selected from hydrogen and an amino acid sidechain, where at least one of $R^{42}$ and $R^{43}$ are hydrogen, and at least one of $R^{45}$ and $R^{46}$ are hydrogen. In certain embodiments, in formula (VI), Q is a saturated fatty acid comprising 20 carbons or less; and X—Y is luciferin.

In certain embodiments, a subject lipid-probe compound is of the structure of formula (VII):

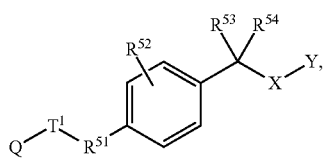

where Q, X, $T^1$ and Y are as defined above;
$R^{51}$ is O, S or NH;
$R^{52}$ is one or more groups, each $R^{52}$ independently selected from H, an alkyl, an aliphatic, an amino, an aryl, an acyl, an alkoxy, an aryloxy, an acyloxy, a carbonyl, a cyano, a halogen, hydroxyl, a heterocyclic group, a nitro, a thio, a sulfinyl, a sulfonyl, and a trifluoromethyl; and
$R^{53}$ and $R^{54}$ are independently selected from hydrogen, an alkyl, an aryl and a heterocyclic group.

In certain embodiments, in formula (VII), $R^{51}$ is O; and $R^{52}$, $R^{53}$ and $R^{54}$ are hydrogen. In certain embodiments, in formula (VII), $T^1$-$R^{51}$ comprises a cleavable boronic ester; X is O; and $R^{52}$, $R^{53}$ and $R^{54}$ are hydrogen. In certain embodiments, in formula (VII), Q is a saturated fatty acid comprising 20 carbons or less; and X—Y is luciferin.

In certain embodiments, a subject lipid-probe compound is one of the following structures:

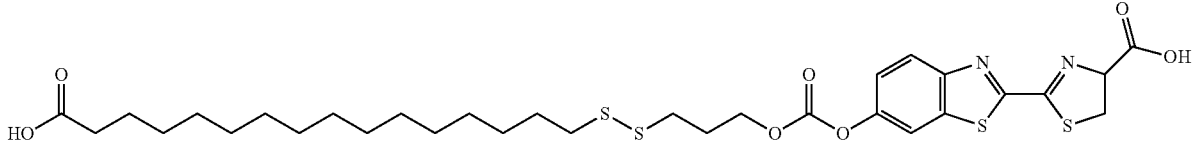

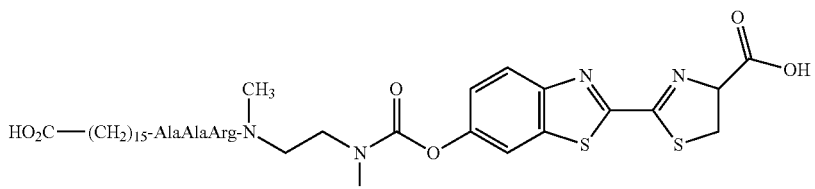

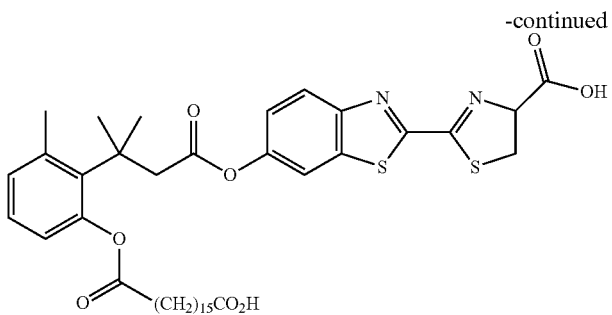

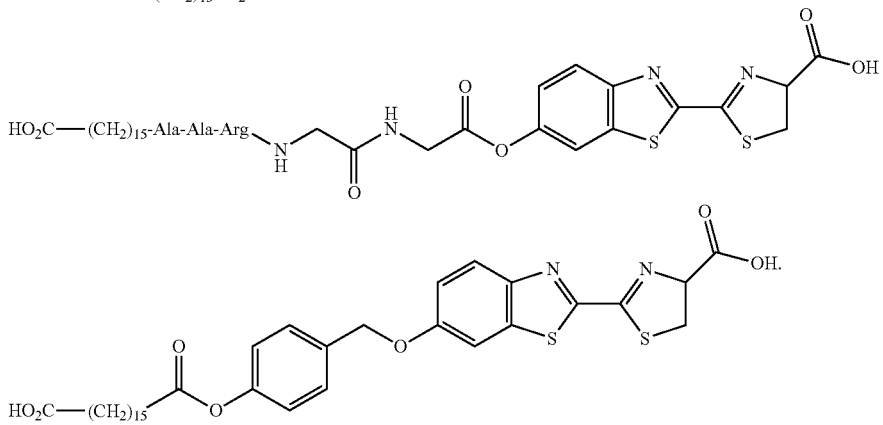

A subject lipid-probe compound is in some embodiments hydrophobic. In some embodiments, a subject lipid-probe compound is rendered hydrophobic by association with a carrier that provides for hydrophobicity. Examples of suitable carriers are described below.

Compositions

The present disclosure provides compositions, including pharmaceutical compositions, comprising a subject lipid-probe compound. A subject composition can comprise, in addition to a subject lipid-probe compound, one or more of: a salt, e.g., NaCl, MgCl, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as Tween-20, etc.; a protease inhibitor; and the like.

In some embodiments, a subject composition includes a carrier, where suitable carriers include, but are not limited to, albumin; a lipoprotein particle; a mixed micelle (e.g., a micelle comprising taurocholate); a poly(ethylene glycol) (PEG); an oil (e.g., a biocompatible oil such as olive oil); a lipid nanoparticle as described in U.S. Pat. No. 7,691,405; a microparticle as described in U.S. Pat. No. 7,713,942; and the like.

In some embodiments, a subject composition is a pharmaceutical composition, e.g., a pharmaceutical composition comprising a subject lipid-probe compound and a pharmaceutically acceptable excipient. Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., $17^{th}$ edition, 1985. The composition or formulation to be administered will, in any event, contain a quantity of the compound adequate to achieve the desired image in the subject to which the composition is administered. The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Utility

As noted above, a subject lipid-probe compound finds use in various in vitro and in vivo imaging applications. A subject lipid-probe compound can be used to monitor uptake of a lipid in vivo; to determine the kinetics of uptake of a lipid; to determine the localization of uptake of a lipid (e.g., uptake into a particular organ or tissue); etc. A subject lipid-probe compound can be used in screening methods to identify agents that modulate lipid uptake, and that are therefore candidates for treating disorders of lipid uptake (e.g., obesity, and the like).

A subject detection assay takes advantage of the fact that the lipid-probe compound is actively taken up into a cell (e.g., by active transport), and the probe accumulates in the cell. After the lipid-probe compound has been taken up by the cell, the probe is released from the lipid-probe compound. Accumulation of the probe in a cell thus increases the signal-to-noise ratio.

A subject detection assay is useful in various diagnostic applications. A subject detection method can be used to detect uptake of a lipid into a living cell in vivo. Such a method finds use, e.g., in diagnosing abnormalities of lipid uptake. For example, a cardiac disorder can be diagnosed by detecting an abnormality in lipid uptake into cardiac tissue.

As another example, a liver disorder (e.g., fatty liver disease) can be diagnosed by detecting an abnormality of lipid uptake into the liver.

A subject detection assay can also be used to monitor efficacy of treatment, e.g., treatment for a cardiac disorder, treatment for a liver disorder, treatment for a kidney disorder, etc. As subject detection assay can also be used to monitor the progression of a disease or disorder over time.

Detection of Lipid Uptake into a Living Cell In Vitro

The present disclosure provides a method of detecting lipid uptake into a living cell in vitro. In some embodiments, a subject detection method involves contacting a subject lipid-probe compound with a living cell in vitro, e.g., a subject lipid-probe compound is contacted with cells growing in suspension (e.g., as unicellular entities) or as a monolayer in in vitro cell culture; and detecting a signal generated following uptake of the lipid-probe compound into the cell. The cells can be primary cells, non-transformed cells, cells isolated from an individual, immortalized cell lines, etc.

Non-limiting examples of cells are cells of multicellular organisms, e.g., cells of invertebrates and vertebrates, such as myoblasts, cardiomyocytes, neutrophils, erythrocytes, osteoblasts, chondrocytes, basophils, eosinophils, adipocytes, invertebrate neurons (e.g., Helix aspera), vertebrate neurons, mammalian neurons, adrenomedullary cells, melanocytes, epithelial cells, and endothelial cells; tumor cells of all types (e.g., melanoma, myeloid leukemia, carcinomas of the lung, breast, ovaries, colon, kidney, prostate, pancreas and testes); cardiomyocytes, endothelial cells, lymphocytes (T-cell and B cell), mast cells, vascular intimal cells, hepatocytes, leukocytes including mononuclear leukocytes; stem cells such as hematopoietic stem cells, neural, skin, lung, kidney, liver and myocyte stem cells; osteoclasts, connective tissue cells, keratinocytes, melanocytes, hepatocytes, and kidney cells.

Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

Suitable methods of detecting a signal generated following uptake of a subject lipid-probe compound into a living cell in vitro include, e.g., microscopy, fluorescence activated cell sorting, spectroscopy (e.g., a multi-well plate reader that detects luminescence), luminometers, photomultiplier tubes, and the like.

Detection of Lipid Uptake into a Living Cell In Vitro or In Vivo

The present disclosure provides a method of detecting lipid uptake into a living cell in vivo, e.g., in a living multicellular organism. In some embodiments, the method involves administering a subject lipid-probe compound (or a composition comprising a subject lipid-probe compound) to a multicellular organism (e.g., an individual such as a mammal); and detecting a signal generated following uptake of the lipid into a cell of the multicellular organism (e.g., in a cell of the individual). A subject detection method can also be carried out ex vivo, e.g., where a tissue or cells are taken from an individual and imaged.

Suitable methods of detecting a signal generated following uptake of a subject lipid-probe compound into a living cell in vitro include, e.g., microscopy, fluorescence activated cell sorting, spectroscopy (e.g., a multi-well plate reader that detects luminescence), luminometers, photomultiplier tubes, and the like. Suitable methods of detecting a signal generated following uptake of a subject lipid-probe compound into a living cell in vivo include, e.g., use of a charged-coupled device (CCD) camera; a cooled CCD camera; or any other such device.

In some in vitro and/or in vivo embodiments, the cell(s) in which lipid uptake is being detected is(are) genetically modified to produce luciferase, e.g., where the probe portion of the lipid-probe compound is a luciferin or similar compound, as described above. For example, in some embodiments, a subject method involves use of a non-human transgenic animal (e.g., a rat, mouse, lagomorph, ungulate, etc.) comprising a transgene that comprises a nucleotide sequence encoding a luciferase.

Luciferase-encoding nucleic acids from any of a wide variety of vastly different species, e.g., the luciferase genes of *Photinus pyralis* and *Photuris pennsylvanica* (fireflies of North America), *Pyrophorus plagiophthalamus* (the Jamaican click beetle), *Renilla reniformis* (the sea pansy), and several bacteria (e.g., *Xenorhabdus luminescens* and *Vibrio* spp), can be used. In addition, variant luciferase can be used; see, e.g., variant luciferase described in U.S. Pat. No. 7,507,565. Numerous luciferase amino acid sequences (and corresponding encoding nucleotide sequences) are available; see, e.g., GenBank Accession Nos.: 1) BAH86766, and GenBank AB508949 for the corresponding encoding nucleotide sequence; 2) CAA59282 (*Photinus pyralis*) and GenBank X84847 for the corresponding encoding nucleotide sequence; 3) ABD66580.1 (*Diaphenes pectinealis*); 4) AAV32457.1 *Cratomorphus distinctus*); 5) AAR20792.1 (*Pyrocoelia rufa*); 6) AAR20794.1 (*Lampyris notiluca*); 7) AAL40677 (*Pyrocystis lunula*), and GenBank AF394059 for the corresponding encoding nucleotide sequence; and 8) AAV35380 (*Pyrocystis noctiluca*), and GenBank AY766385 for the corresponding encoding nucleotide sequence.

In some embodiments, the luciferase is encoded by a nucleotide sequence encoding the luciferase, and the nucleotide sequence is operably linked to a control element. Suitable control elements include promoters, enhancers, and the like. In some embodiments, the promoter is a constitutive promoter. In other embodiments, the promoter is an inducible promoter. In other embodiments, the promoter is a cell type-specific promoter. Such promoters are well known in the art.

In some embodiments, luciferase is expressed as a transgene in a non-human transgenic animal (e.g., a rat, a mouse, an ungulate, a lagomorph, etc.). In some embodiments, the luciferase is expressed in all cells of the transgenic non-human animal. In other embodiments, the luciferase is expressed in a subset of cells in the transgenic non-human animal. For example, in some embodiments, the luciferase is expressed only in neurons in the transgenic non-human animal. As another example, in some embodiments, the luciferase is expressed only in cardiac cells. As another example, in some embodiments, the luciferase is expressed only in intestinal cells (e.g., intestinal epithelial cells). In these embodiments, the luciferase-encoding transgene comprises a nucleotide sequence encoding luciferase, where the nucleotide sequence is operably linked to a cell type-specific control element.

In some embodiments, a subject lipid-probe compound can be used to detect lipid uptake in a non-transgenic animal, e.g., a non-transgenic mammal, a human, etc., e.g., where the lipid-probe compound comprises gadolinium or other such moiety as the probe. Where the subject lipid-probe compound includes gadolinium or other such moiety as the probe, suitable detection methods include magnetic resonance imaging.

A subject detection method can be used to detect lipid uptake in a cell in response to an internal or an external stimulus. External and internal signals (stimuli) include, but are not limited to, infection of a cell by a microorganism, including, but not limited to, a bacterium (e.g., *Mycobacterium* spp., *Shigella, Chlamydia*, and the like), a protozoan (e.g., *Trypanosoma* spp., *Plasmodium* spp., *Toxoplasma* spp., and the like), a fungus, a yeast (e.g., *Candida* spp.), or a virus (including viruses that infect mammalian cells, such as human immunodeficiency virus, foot and mouth disease virus, Epstein-Barr virus, and the like; viruses that infect plant cells; etc.); change in pH of the medium in which a cell is maintained or a change in internal pH; excessive heat relative to the normal range for the cell or the multicellular organism; excessive cold relative to the normal range for the cell or the multicellular organism; an effector molecule such as a hormone, a cytokine, a chemokine, a neurotransmitter; an ingested or applied drug; a ligand for a cell-surface receptor; a ligand for a receptor that exists internally in a cell, e.g., a nuclear receptor; hypoxia; a change in phospholipid structure; light; dark; caloric restriction; caloric intake; mitogens, including, but not limited to, lipopolysaccharide (LPS), pokeweed mitogen; stress; antigens; sleep pattern (e.g., sleep deprivation, alteration in sleep pattern, and the like); an apoptosis-inducing signal; electrical charge (e.g., a voltage signal); ion concentration of the medium in which a cell is maintained, or an internal ion concentration, exemplary ions including sodium ions, potassium ions, chloride ions, calcium ions, and the like; presence or absence of a nutrient; metal ions; a transcription factor; a tumor suppressor; cell-cell contact; adhesion to a surface; peptide aptamers; RNA aptamers; intrabodies; and the like.

For example, in some embodiments, a cell is contacted with a subject compound and an internal or external stimulus is applied; and the signal produced by the compound is detected and compared to the signal detected in the absence of the internal or external stimulus.

A subject detection method can be used to detect the level of lipid uptake into a cell (in vitro or in vivo) as a function of a particular physiological state. For example, lipid uptake is measured in a cell when the cell (e.g., a single cell in vitro; or a cell in a multicellular organism) is in a first physiological state; and lipid uptake is measured in the same cell when the cell is in a second physiological state. For example, the first physiological state could be the absence of disease or absence of a condition; and the second physiological state could be a disease state or a particular condition. Thus, for example, lipid uptake can be measured in cells or tissues of individual to detect the presence of a disease state or a condition. Disease states and other conditions that may affect lipid uptake include, but are not limited to, diabetes, obesity, cardiac disorders, liver disorders, skeletal muscle disorders, and the like.

A subject detection method can be used to detect lipid uptake into a cell (e.g., a single cell in vitro; or a cell in a multicellular organism) over time. For example, lipid uptake is detected at a first time and at a second time; and the levels of lipid uptake detected at the first and second times are compared. In some embodiments, the first time is before treatment with an agent (e.g., a therapeutic agent); and the second time is after treatment with an agent. In these embodiments, the level of lipid uptake can be used to determine the effect of treatment of an individual with the agent. For example, response to treatment with an anti-obesity drug can be monitored using a subject method.

In some embodiments, a subject method can be used to determine the effect of diet on lipid uptake. For example, response to dietary changes can be monitored using a subject method.

A subject lipid-probe compound can be used to determine the effect that an agent has on the lipid uptake into a cell and/or cells (e.g., a single cell in vitro; or a cell in a multicellular organism). Agents that can be tested for an effect on lipid uptake into a cell include, but are not limited to, therapeutic agents; hormones; anti-obesity agents; anti-diabetic agents; and any other agent that can be administered to cells and/or multicellular organisms.

A subject lipid-probe compound can be administered to an individual via any number of modes and routes of administration. In some embodiments, a subject compound is administered systemically (e.g., via intravenous injection; via oral administration; etc.). In other embodiments, a subject compound is administered locally. A subject compound can be administered intravenously, intratumorally, peritumorally, orally, topically, subcutaneously, rectally, vaginally, or any other enteral or parenteral route of administration. A subject compound can be administered at a local site, e.g., at, near, or into a particular organ or tissue.

Screening Methods

The present disclosure provides methods of identifying an agent that modulates (increases or decreases) uptake of a lipid into a cell in vivo or in vitro. The methods generally involve contacting an in vitro cell, or administering to a multicellular organism (e.g., an experimental laboratory animal such as a rat or mouse), a subject lipid-probe compound and a test agent; and determining the effect, if any, of the test agent on the uptake of the lipid-probe compound into the cell in vitro or into a cell (e.g., into an organ or into a tissue) of the multicellular organism.

Whether the test agent modulates uptake of the lipid-probe compound into a cell (or organ or tissue) can be determined by detecting the released probe. In some embodiments, as described above, detection of the released probe (e.g., luciferin, coelenterazine, etc.) in a multicellular organism occurs when the released probe is acted upon by luciferase present in the multicellular organism, e.g., where the multicellular organism comprises a transgene that encodes a luciferase. In other embodiments, as described above, detection of the probe is by MRI (e.g., where the lipid-probe compound comprises an MRI agent such as gadolinium).

A test agent of interest for increasing uptake of a lipid into a cell is a test agent that increases uptake of a lipid into a cell (or organ, or tissue) by at least about 10%, at least about 25%, at least about 50%, at least about 2-fold, at least about 2.5-fold, at least about 5-fold, at least about 10-fold, or more than 10-fold, compared to the level of uptake of the lipid into the cell (or organ, or tissue) in the absence of the test agent. For example, an agent that increases uptake of a fatty acid into brown adipose tissue can be considered a candidate agent for controlling weight gain.

A test agent of interest for decreasing uptake of a lipid into a cell is a test agent that reduces uptake of a lipid into a cell (or organ, or tissue) by at least about 10%, at least about 20%, at least about 30%, at least about 40%, at least about 50%, at least about 60%, at least about 70%, at least about 80%, or at least about 90%, or more, compared to the level of uptake of the lipid into the cell (or organ, or tissue) in the absence of the test agent. A test agent of interest that reduces uptake of a lipid into a cell (or organ, or tissue) is considered a candidate agent for the treatment of a disorder such as obesity, hepatosteatosis, and the like.

The terms "candidate agent," "test agent," "agent," "substance," and "compound" are used interchangeably herein. Test agents encompass numerous chemical classes, typically synthetic, semi-synthetic, or naturally-occurring inorganic or organic molecules. Test agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or are readily producible.

Test agents may be small organic or inorganic compounds having a molecular weight of more than 50 and less than about 2,500 daltons. Test agents may comprise functional groups necessary for structural interaction with other macromolecules such as proteins, e.g., hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Test agents are also found among biomolecules including peptides, saccharides, fatty acids, steroids, purines, pyrimidines, derivatives, structural analogs or combinations thereof.

Assays of the invention include controls, where suitable controls include controls (e.g., cells; non-human animal) not contacted with or administered the test agent. A plurality of assays can be run in parallel with different test agent concentrations to obtain a differential response to the various concentrations. Typically, one of these concentrations serves as a negative control, i.e. at zero concentration or below the level of detection.

As noted above, a subject screening method can be used to identify candidate agents for treating various disorders. A subject screening method can also be used as a secondary screen, e.g., to determine whether a drug being developed to treat a certain disorder will have an adverse effect on cardiac function. For example, a transgenic non-human animal comprising a transgene that encodes luciferase, and that expresses the luciferase in a cardiac-specific manner, can be used to determine whether a drug being developed to treat a certain disorder will have an adverse effect on uptake of a lipid into cardiac cells.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); nt, nucleotide(s); i.m., intramuscular(ly); i.p., intraperitoneal(ly); s.c., subcutaneous(ly); and the like.

Example 1

Synthesis of FFA-luciferin Compounds

Synthesis of FFA-Luc Compound 1

The synthesis of compound 1 is summarized in Scheme 1 below.

Scheme 1. Synthesis of FFA-luc probe.

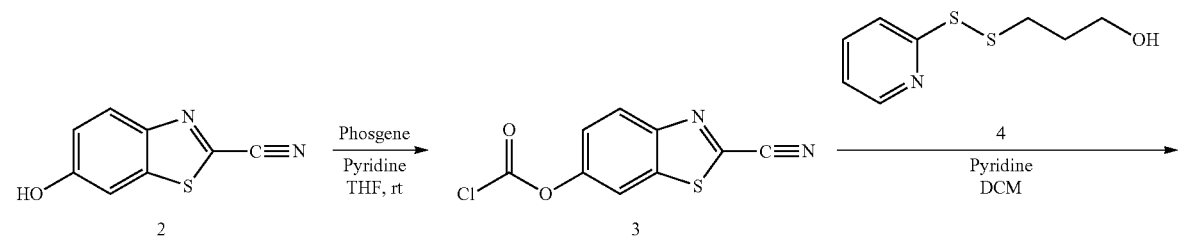

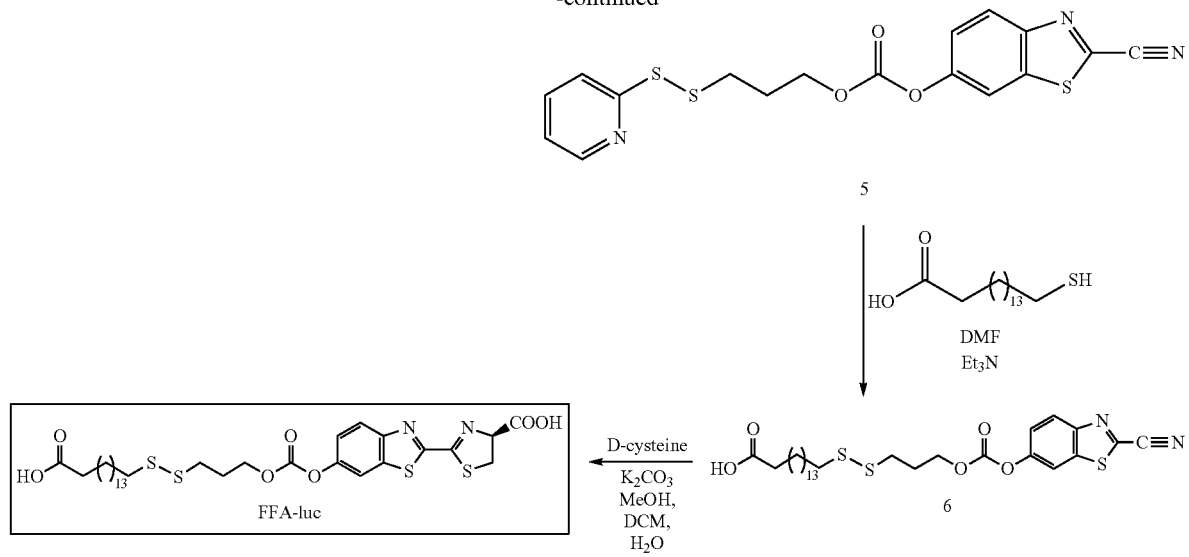

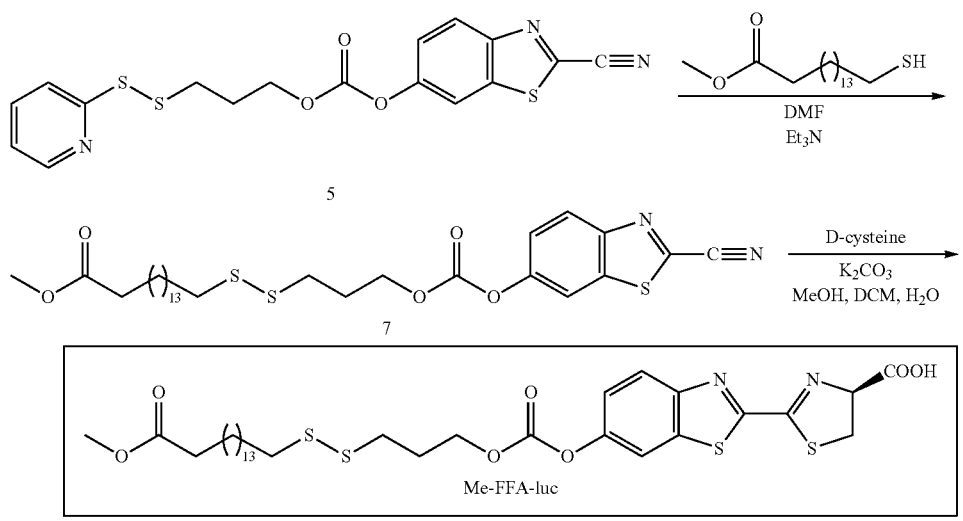

All chemical reagents obtained from commercial suppliers were used without further purification unless noted. All compounds/solvents were purchased from Sigma-Aldrich except D-cysteine hydrochloride, which was from Anaspec, Inc, 16-mercaptohexadecanoic acid and methyl-16-mercaptohexadecanoate which were from Asemblon INC, and 2-cyano-6-hydroxybenzothiazole which was from Shanghai Chemical Pharm-Intermediate Tech. Co., Ltd. Air- and moisture-sensitive reactions were performed in oven-dried glassware under an $N_2$ atmosphere. Solvents were degassed by sparging with nitrogen for at least 20 min. Deionized water was obtained from a Milli-Q purification system. Dichloromethane ($CH_2Cl_2$) was dried by passage over a column of activated alumina under an $N_2$ atmosphere. Flash chromatography was performed using Silicycle SiliaFlash P60 230-400 mesh silica gel. Analytical thin layer chromatography was performed using glass-backed Silicycle Ultra-Pure silica gel 60 Å F254 plates. Reversed phase high performance liquid chromatography (RP-HPLC) was performed on a Varian Pro Star system with a Varian UV-Vis detector model 330 using a Microsorb C-18 preparative column (21.4×250 mm) at a flow rate of 10 mL/min. Gradients of $H_2O$ and MeOH were used as the mobile phase.

All NMR spectra ($^1H$) were obtained on Bruker DRX-500, AVB-400, and AVQ-400 MHz spectrometers. Data for $^1H$ NMR spectra are reported as follows: chemical shift, multiplicity (s=singlet, d=doublet, dd=doublet of doublet, t=triplet, q=quintet, and m=multiplet), and integration. Data for $^1H$ NMR spectra were referenced to residual solvent peaks ($CDCl_3$: 7.26 ppm and $CD_3OD$: 3.31 ppm).

The synthesis of FFA-luc is outlined in Scheme 1. 2-cyano-6-hydroxybenzothiazole 2 is converted into the chloroformate 3 by reaction with a solution of phosgene in toluene (20%) and pyridine in THF. This is then coupled with 3-(pyridin-2-yldisulfanyl)propan-1-ol (4) to give carbonate 5. The thiopyridyl moiety of 5 was displaced with 16-mercaptohexadecanoic acid in DMF to give the transporter-linker conjugate 6. Condensation with D-cysteine completed the luciferin scaffold, resulting in FFA-luc (compound 1).

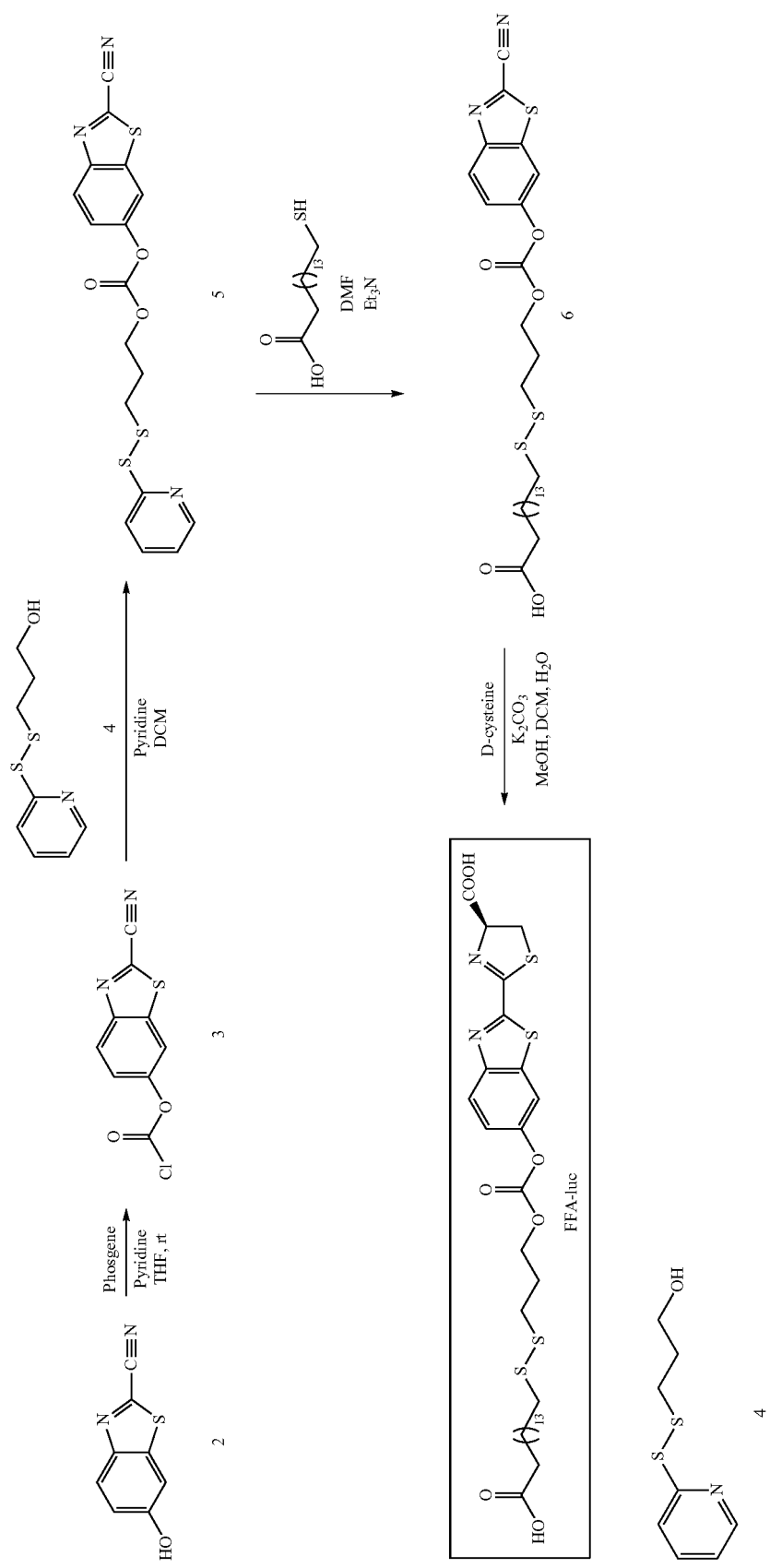
Scheme 1: Synthesis of FFA-luc compound 3-(pyridin-2-yldisulfanyl)propan-1-ol (4). 4 was prepared as reported previously with slight modifications. To an oven dried flask under nitrogen at room temperature equipped with a stir bar was added 2'-aldrithiol (3.84 g, 17.44 mmol) in 12 mL of methanol purged with nitrogen. To this mixture was added 3-mercaptopropanol dropwise (0.50 mL, 5.81 mmol). The solution turned yellow and was allowed to stir for 3 hours. The solvent was then removed in vacuo and flash chromatography was performed using 1:1 hexanes: ethyl acetate. The product was a yellow oil. The NMR matched those previously reported.

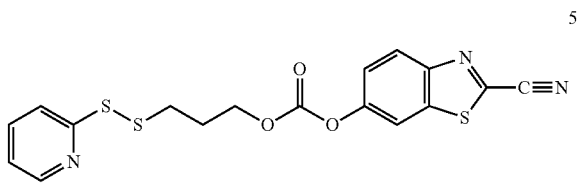 [SMILES: N#Cc1nc2ccc(OC(=O)OCCCSSc3ccccn3)cc2s1]

2-cyanobenzo[d]thiazol-6-yl 3-(pyridin-2-yldisulfanyl) propyl carbonate (5). To an oven dried flask equipped with a stir bar and a Teflon cap under nitrogen was added phosgene (20% w/v in toluene) (0.98 mL, 1.99 mmol). A solution of 2-cyano-6-hydroxybenzothiazole (2) (88.5 mg, 0.50 mmol) and pyridine (44.18 µL, 0.55 mmol) in tetrahydrofuran (6 mL) was added dropwise over 30 min to the reaction flask. This was allowed to stir overnight. The flask was purged into a solution of aqueous potassium hydroxide for 10 min and then the solvent was evaporated in vacuo. A solution of 3-(pyridin-2-yl-disulfanyl)-propan-1-ol (4) (100.00 mg, 0.50 mmol) and pyridine (44.18 µL, 0.55 mmol) in methylene chloride (4 mL) was added to the flask at room temperature under nitrogen. This was allowed to stir for 1 h and then the solvent was evaporated in vacuo. The compound was purified by reverse phase high performance liquid chromatography (RP-HPLC) (40% methanol/60% water to 100% methanol over 45 min then 100% methanol for 12 min, maximum peak elution at 38.9 min). The methanol was removed from fractions containing product. $^1$H NMR (CDCl$_3$, 500 MHz): $\delta_H$ 2.17 (2H), 2.93 (2H), 4.40 (2H), 7.08 (1H), 7.51 (1H), 7.61 (2H), 7.84 (1H), 8.07 (1H), 8.45 (1H) Calcd for C$_{17}$H$_{14}$N$_3$O$_3$S$_3$ [M+H]$^+$ 404.0, found 404.0.

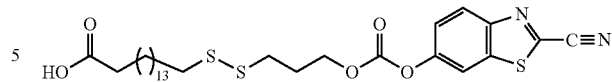

16-((3-((2-cyanobenzo[d]thiazol-6-yloxy)carbonyloxy)propyl)disulfanyl)hexadecanoic acid (6). 5 (50.00 mg, 0.12 mmol) and 16-mercaptohexadecanoic acid (26.0 mg, 0.09 mmol) were placed in a flask. To this flask was added N,N'-dimethylformamide (DMF) (9 mL) and triethylamine (25.87 µL, 0.19 mmol). The reaction was allowed to stir for 2 h at room temperature. The reaction was concentrated in vacuo and purified by RP-HPLC (40% methanol/60% water to 100% methanol over 45 min then 100% methanol for 20 min, maximum peak elution at 54.5 min). The methanol was removed from fractions containing product.

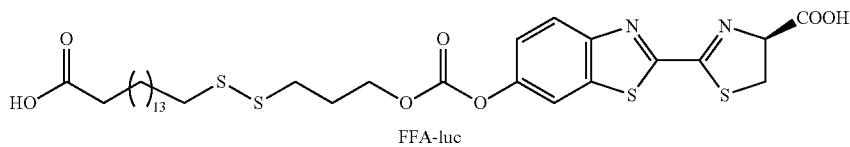

FFA-luc (S)-2-(6-((3-((15-carboxypentadecyl)disulfanyl)propoxy)carbonyloxy)benzo[d]thiazol-2-yl)-4,5-dihydrothiazole-4-carboxylic acid (FFA-luc). D-cysteine hydrochloride (13.5 mg, 0.09 mmol) was placed in a flask which contained 6 (49.90 mg, 0.09 mmol). To this flask was added methanol (5 mL) and dichloromethane (5 mL). A solution of potassium carbonate (11.8 mg, 0.09 mmol) in water (2 mL) and methanol (5 mL) was added to the reaction. The reaction was allowed to stir for 5 min at room temperature (RT) at which time it was quenched by acidification to a pH of 3-4 with 1M HCl. The organic solvent was removed in vacuo and the remaining water removed via lyophilization. The crude material was purified by RP-HPLC (40% methanol/60% water to 100% methanol over 45 min then 100% methanol for 20 min, maximum peak elution at 54.4 min). The methanol was removed from fractions containing product to afford a white solid. $^1$H NMR (CD$_3$OD, 500 MHz): $\delta_H$ 1.33 (m), 1.58 (m, 2H), 1.70 (q, 2H), 2.27 (t, 2H), 2.70 (t, 2H), 2.83 (t, 2H), 3.21 (q, 2H), 3.79 (dd, 2H), 4.39 (t, 2H), 5.33 (t, 1H), 7.30 (dd, 1H), 7.95 (d, 1H), 8.13 (d, 1H) Calcd for C$_{31}$H$_{45}$N$_2$O$_7$S$_4$ [M+H]$^+$ 685.2, found 685.2.

Scheme 2: Synthesis of Me-FFA-luc compound

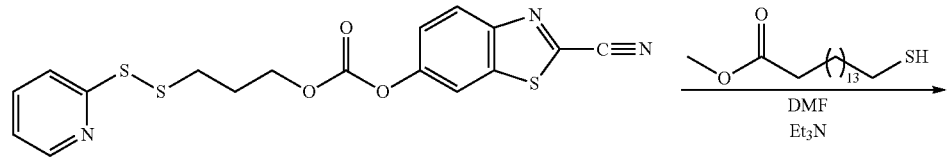

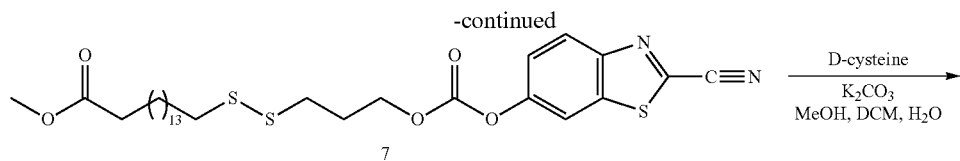

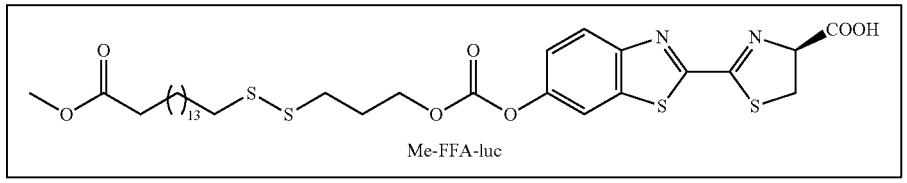

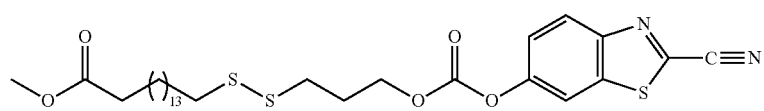

Methyl 16-((3-((2-cyanobenzo[d]thiazol-6-yloxy)carbonyloxy)propyl)disulfanyl)hexadecanoate (7). 5 (3.4 mg, 8.40 μmol) and methyl-16-mercaptohexadecanoate (1.8 mg, 6.13 μmol) were placed in a flask. To this flask was added N,N'-dimethylformamide (DMF) (0.55 mL) and triethylamine (1.75 μL, 12.60 μmol). The reaction was allowed to stir for 2 h at room temperature. The reaction was concentrated in vacuo and purified by RP-HPLC (40% methanol/60% water to 100% methanol over 45 min then 100% methanol for 20 min). The methanol was removed from fractions containing product. $^1$H NMR (CD$_3$OD, 400 MHz): $\delta_H$ 1.29 (m), 1.59 (t, 2H), 1.69 (q, 2H), 2.16 (q, 2H), 2.31 (t, 2H), 2.72 (t, 2H), 2.81 (t, 2H), 3.65 (s, 3H), 4.39 (t, 2H), 7.57 (dd, 1H), 8.09 (d, 1H), 8.24 (d, 1H).

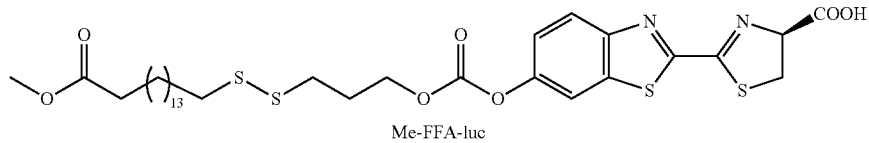

(S)-2-(6-((3-((16-methoxy-16-oxohexadecyl)disulfanyl)propoxy)carbonyloxy)benzo[d]thiazol-2-yl)-4,5-dihydrothiazole-4-carboxylic acid (Me-FFA-luc). D-cysteine hydrochloride (10.7 mg, 0.07 mmol) was placed in a flask which contained 7 (37.2 mg, 0.06 mmol). To this flask was added methanol (3.4 mL) and dichloromethane (3.4 mL). A solution of potassium carbonate (8.7 mg, 0.06 mmol) in water (1.4 mL) and methanol (3.4 mL) was added to the reaction. The reaction was allowed to stir for 30 min at room temperature at which time it was quenched by acidification to a pH of 3-4 with 1M HCl. The organic solvent was removed in vacuo and diluted further with methanol and DMF. The crude material was purified by RP-HPLC (40% methanol/60% water to 100% methanol over 45 min then 100% methanol for 30 min, maximum peak elution at 56.0 min). The methanol was removed from fractions containing product to afford a white solid. This was further purified by RP-HPLC (80% methanol/20% water to 100% methanol over 45 min then 100% methanol for 30 min, maximum peak elution at 47.6 min) followed by extraction (acetonitrile/hexanes) to yield a white solid (15.0 mg, 34%). $^1$H NMR (CD$_3$OD, 500 MHz): $\delta_H$ 1.24-1.32 (m, 20H), 1.36-1.45 (m, 2H), 1.59 (q, 2H, J=7.5 Hz), 1.69 (q, 2H, J=7.5 Hz), 2.15 (q, 2H, J=6.5 Hz), 2.30 (t, 2H, J=7.5 Hz), 2.72 (t, 2H, J=7.5 Hz), 2.83 (t, 2H, J=7.5 Hz), 3.65 (s, 3H), 3.78 (dd, 2H, J=2.0 Hz, 9.5 Hz), 4.39 (t, 2H, J=6.5 Hz), 5.36 (t, 1H, J=9.5 Hz), 7.43 (dd, 1H, J=2.0 Hz, 9.0 Hz), 7.95 (d, 1H, J=2.0 Hz), 8.11 (d, 1H, J=9.0 Hz). $^{13}$C NMR ((CD$_3$)$_2$CO, 150 MHz): $\delta_c$ 25.67, 28.98, 29.11, 30.36, 30.38, 30.46, 34.34, 35.15, 35.53, 35.64, 39.29, 51.44, 68.10, 79.46, 115.76, 122.21, 125.73, 137.49, 151.13, 152.00, 154.09, 162.48, 171.24, 174.13. Calcd for C$_{32}$H$_{47}$N$_2$O$_7$S$_4$ [M+H]$^+$ 699.2272, found 699.2268.

The synthesis of FFA-S-luc (3) is outlined in Scheme S3. 16-bromohexadecanoic acid is coupled to 3-mercapto-1-propanol in DMF using DBU as a base to give compound 10. 2-cyano-6-hydroxybenzothiazole 4 is converted into the chloroformate 5 by reaction with a solution of phosgene in toluene (20%) and N,N-diisopropylethylamine (DIPEA) in THF. Coupling of compound 10 with chloroformate 5 provided carbonate 11. Condensation with D-cysteine completed the luciferin scaffold, resulting in FFA-S-luc (3).

Scheme S3: Synthesis of FFA-S-luc (3)

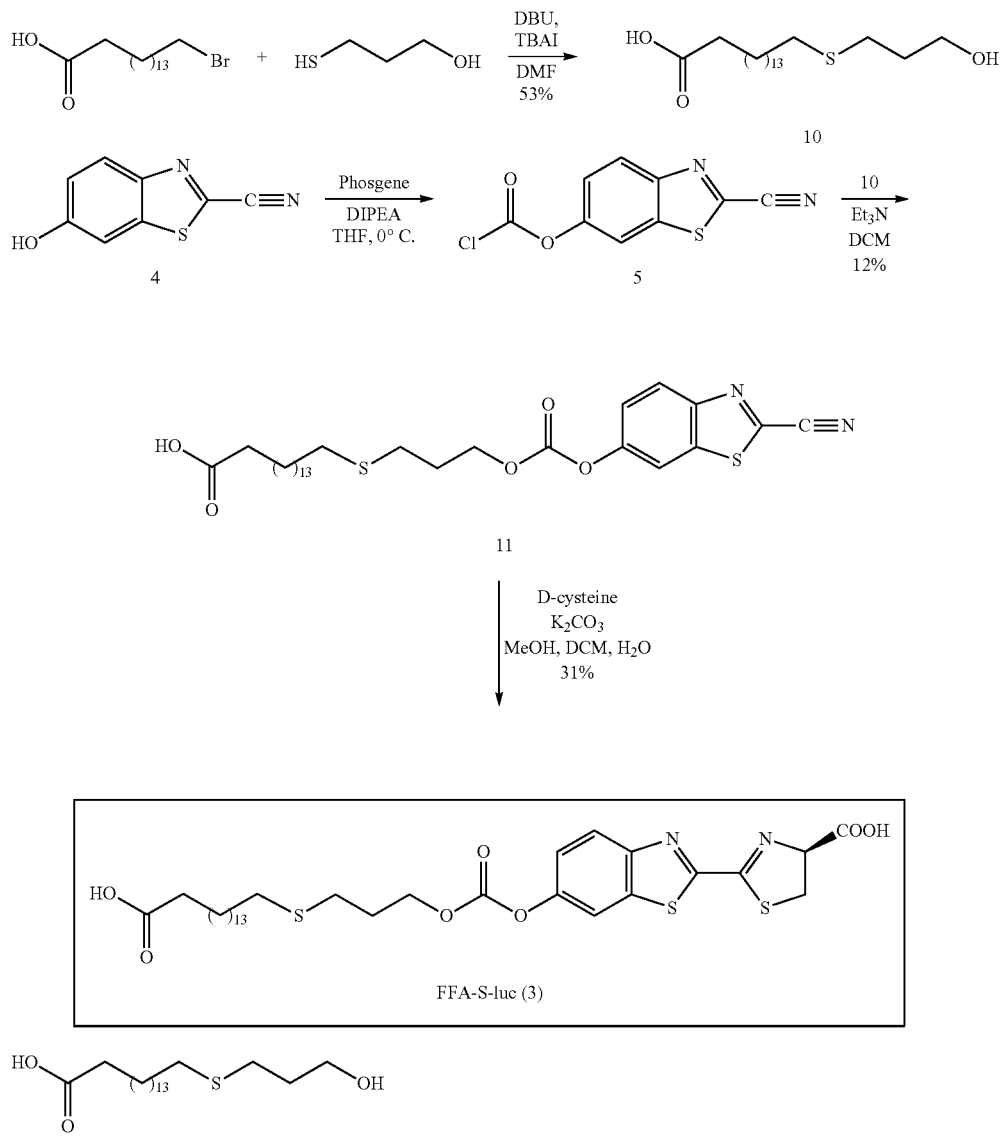

16-(3-hydroxypropylthio)hexadecanoic acid (10). 16-bromohexadecanoic acid (67.00 mg, 2.0 mmol) was dissolved in N,N'-dimethylformamide (DMF) (8 mL). To this was added 3-mercapto-1-propanol (0.172 mL, 2.0 mmol), tetrabutylammonium iodide (TBAI) (148.00 mg, 0.4 mmol), and 1,8-diazabicycloundec-7-ene (DBU) (0.657 mL, 4.4 mmol). The reaction flask was sealed under $N_2$ and the reaction was allowed to stir overnight at room temperature. The reaction was concentrated under a stream of nitrogen and then purified by silica gel chromatography (2:1 to 1:1 hexanes: ethyl acetate with 1% acetic acid) to yield a white solid (368.0 mg, 53%). $^1$H NMR (CDCl$_3$, 400 MHz): $\delta_H$ 1.25 (s, 20H), 1.33-1.43 (m, 2H), 1.54-1.64 (m, 4H), 1.86 (q, 2H, J=6.8 Hz), 2.35 (t, 2H, J=7.6 Hz), 2.53 (t, 2H, J=7.6 Hz), 2.64 (t, 2H, J=6.8 Hz), 3.77 (t, 2H, J=6.0 Hz). $^{13}$C NMR (CDCl$_3$, 125 MHz): $\delta_c$ 24.84, 29.06, 29.18, 29.37, 29.53, 29.63, 29.67, 29.72, 29.85, 31.97, 32.29, 33.95, 62.23, 178.65. HRMS (ESI): Calcd for C$_{19}$H$_{39}$O$_3$S [M+H]$^+$ 347.2614, found 347.2617.

16-(3-((2-cyanobenzo[d]thiazol-6-yloxy)carbonyloxy) propylthio)hexadecanoic acid (11). To an oven dried flask equipped with a stir bar and a Teflon cap under nitrogen was added phosgene (20% w/v in toluene) (0.73 mL, 1.47 mmol). The reaction was cooled to 0° C. in an ice bath. A solution of 2-cyano-6-hydroxybenzothiazole (4) (26.4 mg, 0.15 mmol) and N,N-diisopropylethylamine (DIPEA) (28.2 µL, 0.16 mmol) in tetrahydrofuran (1.8 mL) was added dropwise over 30 min to the reaction flask at 0° C. This was allowed to stir for 2 h. The flask was purged into a solution of aqueous sodium hydroxide for 15 min and then the solvent was evaporated in vacuo. A solution of 10 (51.1 mg, 0.15 mmol) and triethylamine (61.6 μL, 0.44 mmol) in methylene chloride (1.2 mL) was added to the flask at room temperature under nitrogen. This was allowed to stir overnight and then the solvent was evaporated in vacuo. The crude material was purified by RP-HPLC (40% methanol/60% water to 100% methanol over 45 min then 100% methanol for 20 min, maximum peak elution at 53.0 min). The methanol was removed from fractions containing product to afford a white solid (~30 mg). This solid was then further purified by flash chromatography using a Biotage Si 12+M column (4:1 to 1:1 hexanes:ethyl acetate) to yield a white solid (10.1 mg, 12%). $^1$H NMR (CDCl$_3$, 400 MHz): $\delta_H$ 1.25 (s, 20H), 1.33-1.43 (m, 2H), 1.55-1.68 (m, 4H), 2.06 (q, 2H, J=6.4 Hz), 2.35 (t, 2H, J=7.6 Hz), 2.53 (t, 2H, J=7.6 Hz), 2.66 (t, 2H, J=7.2 Hz), 4.42 (t, 2H, J=6.4 Hz), 7.48 (dd, 1H, J=2.4 Hz, 9.2 Hz), 7.88 (d, 1H, J=2.4 Hz), 8.23 (d, 1H, J=9.2 Hz). $^{13}$C NMR (CDCl$_3$, 125 MHz): $\delta_c$ 24.85, 28.32, 28.62, 29.07, 29.20, 29.38, 29.40, 29.57, 29.68, 29.72, 29.75, 29.77, 29.78, 29.85, 32.38, 33.78, 68.11, 112.81, 114.05, 122.47, 126.18, 136.26, 137.10, 150.21, 151.23, 153.22, 177.85. HRMS (ESI): Calcd for $C_{28}H_{41}N_2O_5S_2$ [M+H]$^+$ 549.2451, found 549.2455.

(S)-2-(6-((3-(15-carboxypentadecylthio)propoxy)carbonyloxy)benzo[d]thiazol-2-yl)-4,5-dihydrothiazole-4-carboxylic acid (FFA-S-luc) (3). D-cysteine hydrochloride (3.1 mg, 0.02 mmol) was placed in a flask which contained 11 (10.1 mg, 0.02 mmol). To this flask was added methanol (1 mL) and dichloromethane (1 mL). A solution of potassium carbonate (2.6 mg, 0.02 mmol) in water (0.4 mL) and methanol (1 mL) was added to the reaction. The reaction was allowed to stir for 30 min at room temperature at which time it was quenched by acidification to a pH of 3-4 with 1M HCl. The organic solvent was removed in vacuo and diluted further with methanol and DMF. The crude material was purified by RP-HPLC (40% methanol/60% water to 100% methanol over 45 min then 100% methanol for 20 min, maximum peak elution at 51.8 min). The methanol was removed from fractions containing product which was further purified by extraction (acetonitrile/hexanes) to afford a white solid (5.0 mg, 31%). $^1$H NMR (CD$_3$OD, 500 MHz): $\delta_H$ 1.24-1.37 (m, 20H), 1.37-1.45 (m, 2H), 1.59 (q, 4H, J=7.5 Hz), 2.02 (q, 2H, J=6.5 Hz), 2.27 (t, 2H, J=7.5 Hz), 2.54 (t, 2H, J=7.5 Hz), 2.65 (t, 2H, J=7.5 Hz), 3.78 (dd, 2H, J=3.0 Hz, 9.5 Hz), 4.38 (t, 2H, J=6.5 Hz), 5.37 (t, 1H, J=9.5 Hz), 7.43 (dd, 1H, J=2.5 Hz, 8.5 Hz), 7.96 (d, 1H, J=2.5 Hz), 8.11 (d, 1H, J=8.5 Hz). HRMS (ESI): Calcd for $C_{31}H_{43}N_2O_7S_3$ [M−H]$^−$ 651.2238, found 651.2233.

See FIG. 1 for lipid imaging approach as illustrated for a fatty acid substrate.

Synthesis of Compounds Including Various Lipids

Compounds including various lipids are prepared using similar methods to those described above. Various lipids include: unsaturated fatty acids, saturated fatty acids, essential fatty acids, trans fatty acids, tri and diglycerides, long and short fatty acids, cholesterol esters, vitamin derived fatty acids (as for example, Vitamin E and K) and phospholipids.

Synthesis of Compounds Including Various Cleavable Linkers

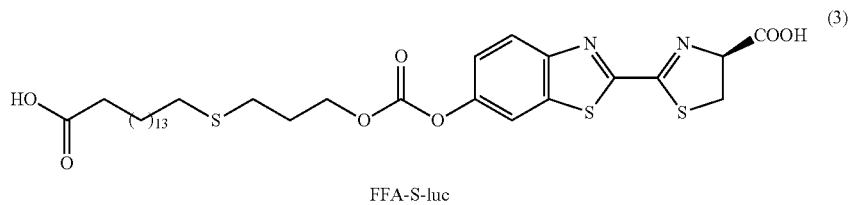

FFA-S-luc

Compounds including suitable cleavable linkers are prepared using similar methods to those described above. Various cleavable linkers are shown in Scheme 2 below, where the cleavable linkage is demonstrated using luciferin as an exemplary leaving group. Suitable linkers include: an enzyme specific peptide sequence, a chemical group specifically cleaved in the presence of an enzyme or a physiological condition (e.g., pH or high concentrations of glutathione).

Scheme 2. Examples of cleavable linkers for use in compounds (each Z is independently S, O or NH; L is a linker; and X is a fatty acid moiety).

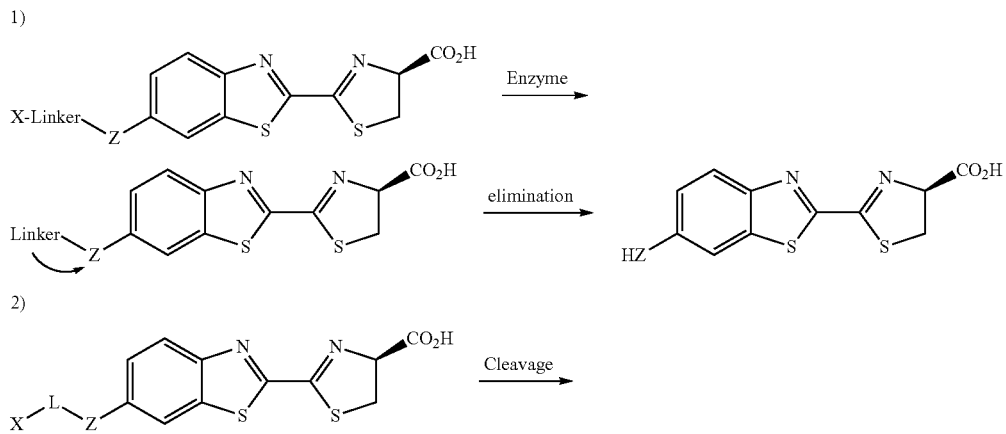

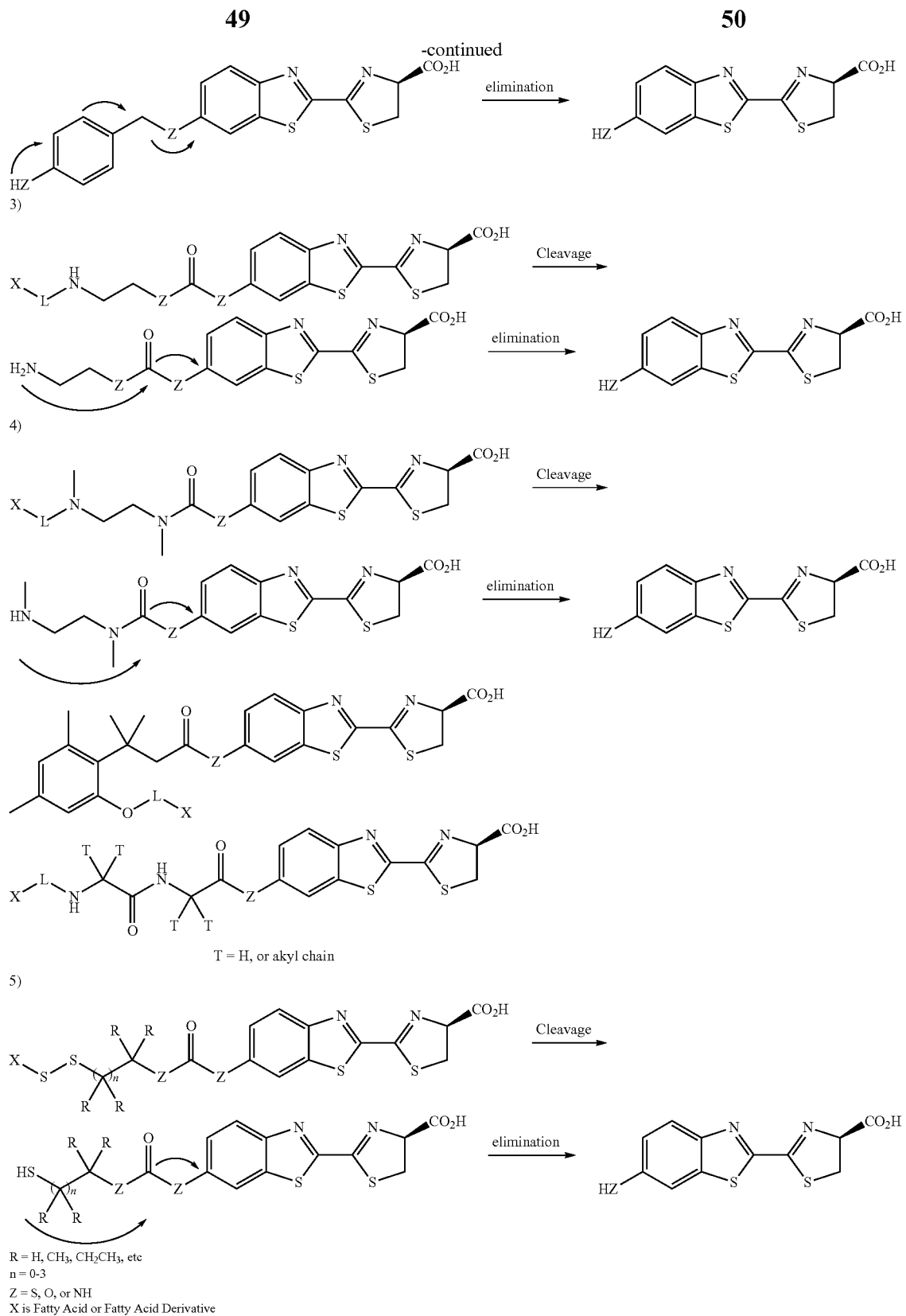

R = H, CH₃, CH₂CH₃, etc
n = 0-3
Z = S, O, or NH
X is Fatty Acid or Fatty Acid Derivative Synthesis of Compounds Including Various Detectable Moieties Compounds including suitable detectable moieties are prepared using similar methods to those described above. Suitable detectable moieties are probes used in optical imaging that are based on fluorescence, bioluminescence, absorption or reflectance as the source of contrast. For example, a compound is prepared using a detectable moiety with bioluminescence that is luciferin or coelenterazine. For example, a compound is prepared using a detectable moiety that is a magnetic resonance imaging (MRI) imaging probe of the following structure:

simultaneous addition of insulin to the cells at the beginning of the uptake assay the insulin effect in general was not only reproduced, but the kinetics of the insulin action was also discerned.

Structure 14

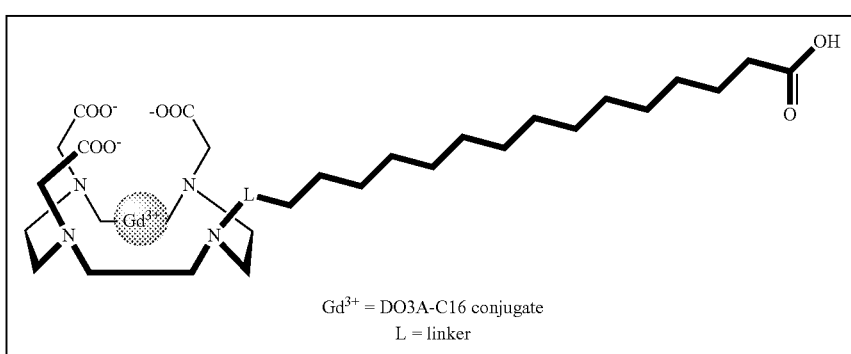

$Gd^{3+}$ = DO3A-C16 conjugate
L = linker

Example 2

Lipid Uptake Imaging

Lipid Imaging Approach

The lipid imaging approach is illustrated in FIG. 1 showing reactions following uptake by luciferase expressing cells.

Example 3

Uptake of FFA-luc In Vitro

Characterization of FFA-luc Uptake In Vitro

Figure 2:
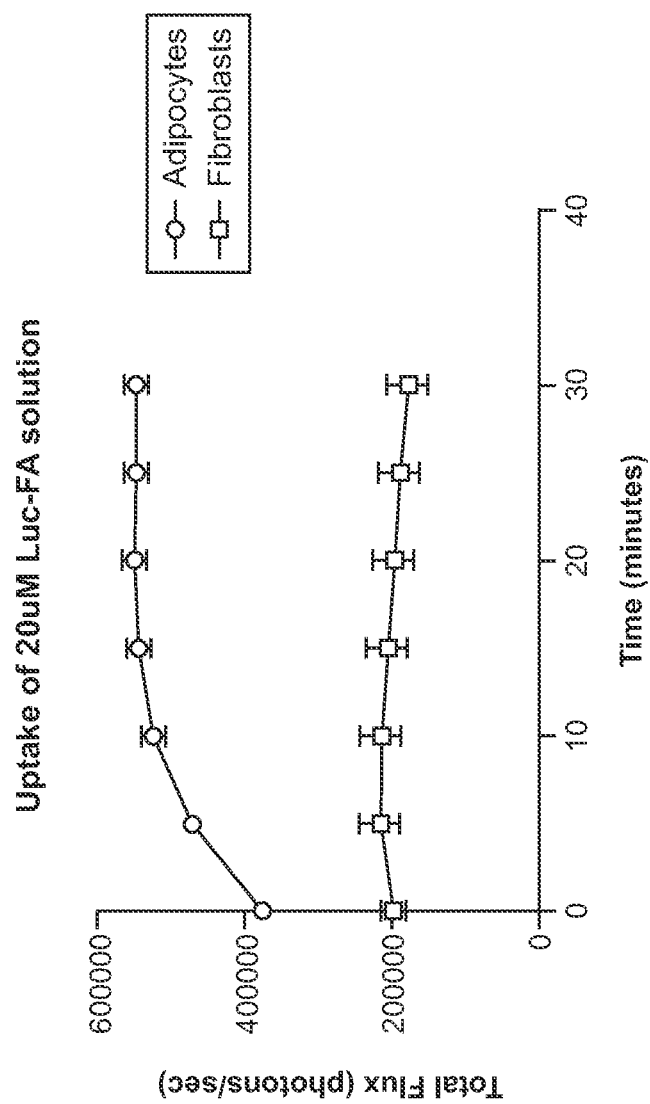
FIG. 2 illustrates FFA-luc probe (see structure on FIG. 1 and Scheme 1) uptake by luciferase expressing fibroblasts vs. adipocytes demonstrating enhanced uptake upon differentiation.
Figure 3:
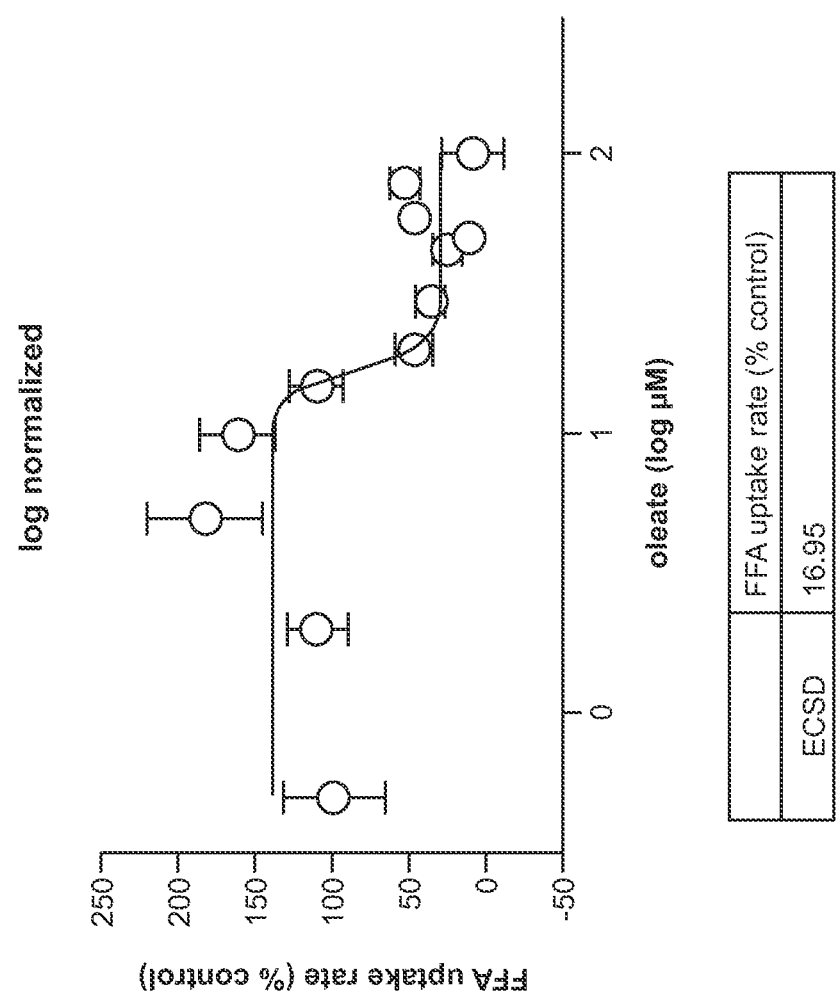
FIG. 3 illustrates the competition of FFA-luc uptake by adipocytes with the natural fatty acid oleate demonstrating that uptake of both compounds is mediated by the same physiological transport system.
Figure 4:
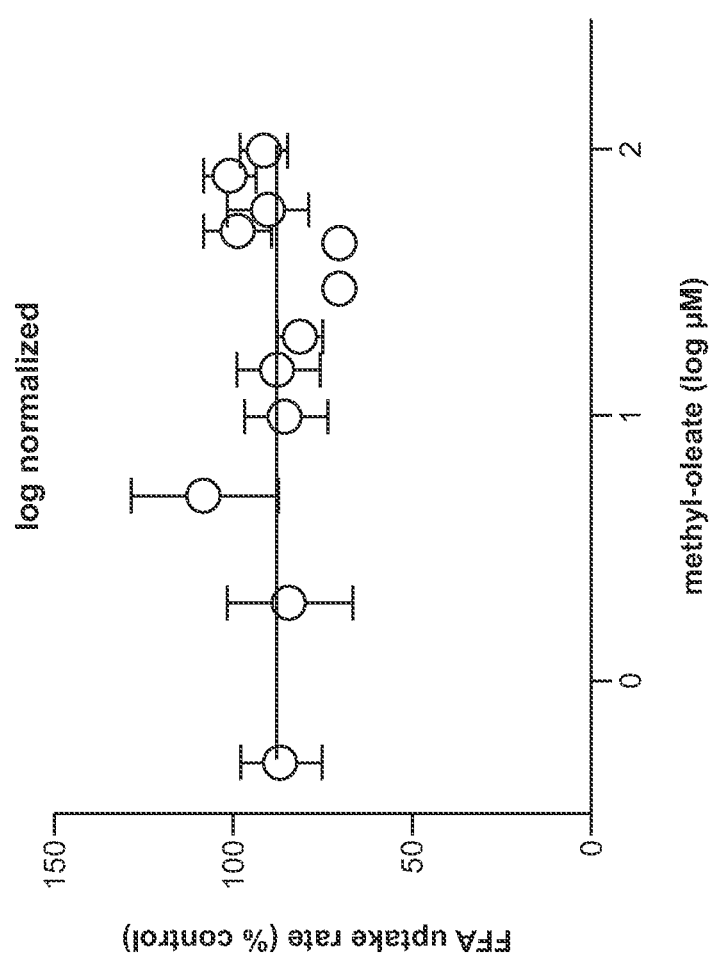
FIG. 4 illustrates the effect of methyl-oleate, which is not a substrate for fatty acid transporters, in competing with FFA-luc uptake by adipocytes.
Figure 5:
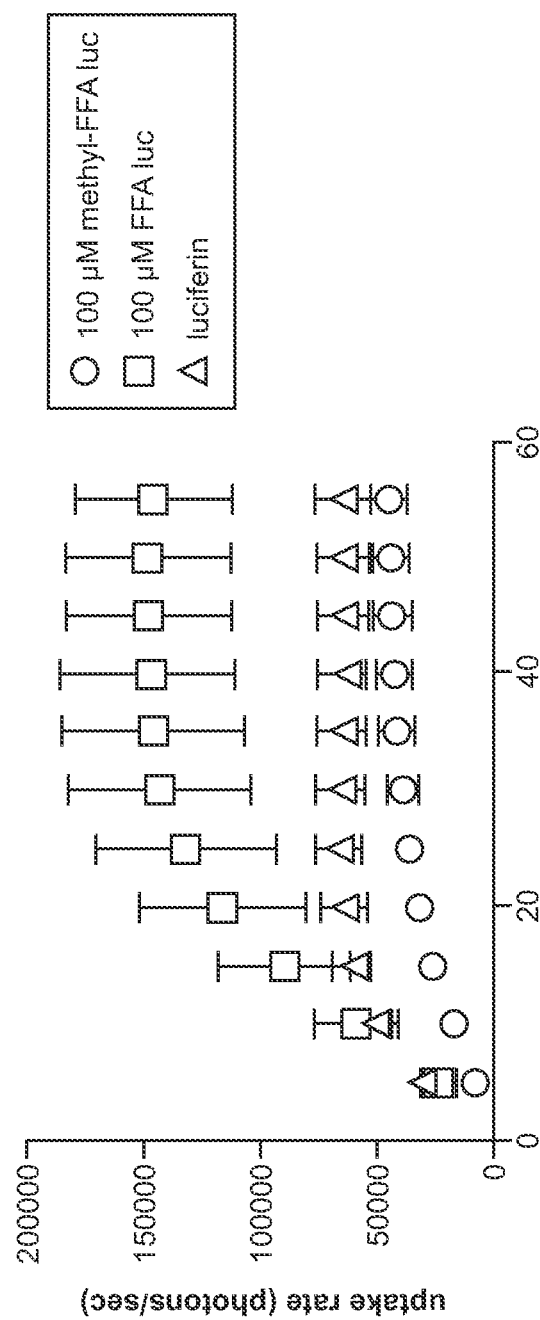
FIG. 5 illustrates uptake of FFA-luc versus a methyl ester of FFA-luc (Me-FFA-luc, see Scheme 2 for structure), that is not a substrate for fatty acid transporters, and unconjugated luciferin, demonstrating that rapid, saturable uptake by adipocytes is only observed for FFA-luc.
Figure 6:
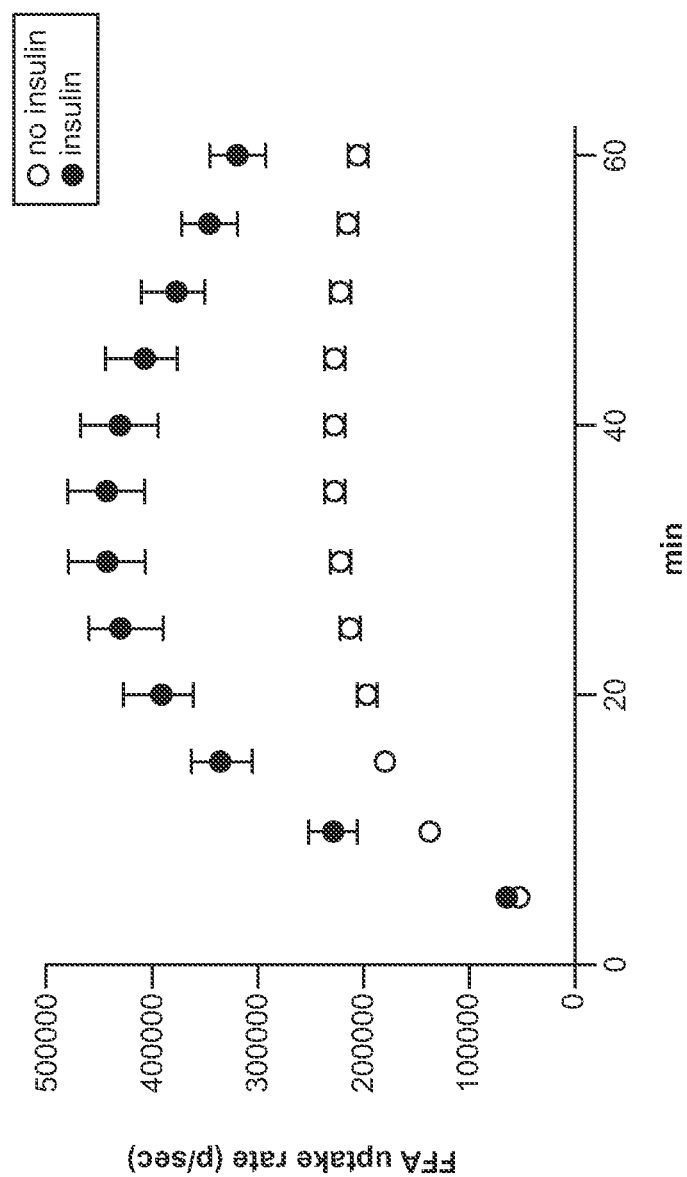
FIG. 6 illustrates the modulation of adipocyte fatty acid uptake by insulin. Addition of insulin at the beginning of the FFA-luc based assay allows discerning of kinetics of insulin effect showing physiological relevance of FFA-luc and demonstrating ability to monitor changes in uptake rates regardless of substrate accumulation over time.

Initial experiments were aimed at demonstrating that the FFA-luc compound is taken up by the same physiological transport process as natural fatty acids. To this end a luciferin expressing cell line was generated based on 3T3 L1 adipocytes. These cells can be differentiated in tissue culture from a fibroblast like precursor to terminally differentiated adipocytes. Since fibroblasts lack the FFA uptake systems of adipocytes, uptake by undifferentiated cells is expected to be significantly lower compared to adipocytes. FIG. 2 shows that this difference in uptake rates can be detected using the FFA-luc compound. If uptake of FFA-luc occurs through the same physiological transport pathway that is being utilized by natural FFA's, such as oleate, then an excess of oleate should compete with FFA-luc uptake, which was demonstrated to be the case (FIG. 3). If uptake of FFA-luc was via diffusion, then competition with oleate would not have been observed. Another prediction based on the same hypothesis was that other naturally occurring fatty acid derivatives, such as methyl-oleate, that are not substrates of the same fatty acid transporter should not compete for FFA-luc uptake even if they are chemically similar to oleate. Indeed methyl-oleate, unlike oleate did not compete for FFA-luc uptake (FIG. 4). As an additional control the methyl ester of the FFA-luc was synthesized, which should not be a substrate for transport. This compound showed indeed slower, non-saturable uptake indicative of simple diffusion (FIG. 5). Finally, the imaging system described herein was used to reproduce a known modifier of fatty acid uptake kinetics, insulin enhanced FFA uptake. FIG. 6 shows that with

Example 4

Uptake of FFA-luc In Vivo

Characterization of FFA-luc Uptake In Vivo

Figure 7:
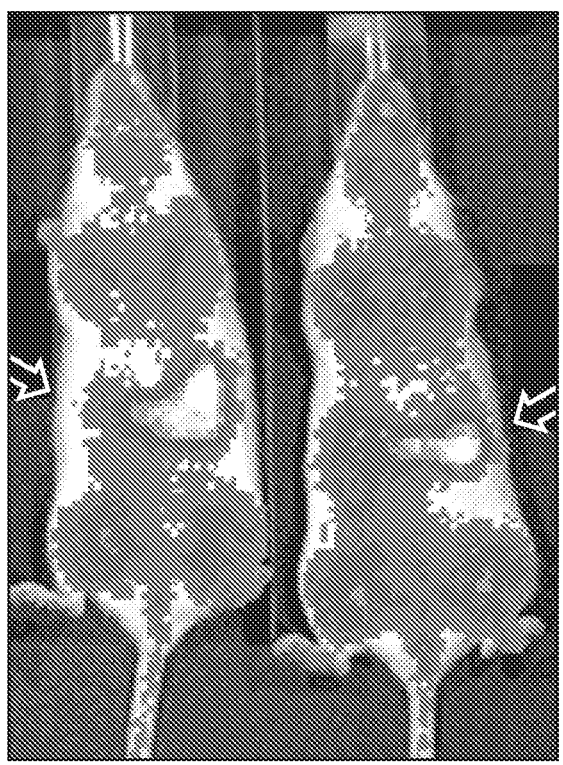
FIG. 7 illustrates intestinal uptake of FFA-luc in vivo at 1 hour (h) following oral gavage. Signal shows uptake by areas consistent with the small intestine. Both mice received 0.02 mg of FFA-luc (compound 1) in poly(ethylene glycol)-400 (PEG 400) vehicle.

To translate the imaging technique described above to in vivo systems, L2G85 mice were utilized. L2G85 mice express luciferase throughout their bodies. Initial experiments focused on detection of intestinal FFA uptake using oral gavages of the FFA-luc compound. Preliminary experiments showed that both propylene glycol and polyethylene glycol are useful vehicles for the oral administration of FFA-luc. Oral gavage of 50 µL of 0.05 mg of FFA-luc conjugate in PEG (FIG. 7) showed a distinct signal emanating from an area consistent with the small intestine (the site of FFA uptake) that slowly increased over time. This is consistent with known fatty acid uptake localization and kinetics.

Figure 8:
FIG. 8 illustrates intestinal uptake of FFA-luc in vivo in the presence of a 200 fold molar excess of oleate at 1 h following oral gavage. The diminished signal in the intestinal region suggests delayed absorption due to competition of FFA-luc with oleate, further demonstrating that FFA-luc is absorbed by the same physiological mechanisms as natural fatty acids.

Addition of a 200 fold excess of oleate over FFA-luc to the gavage medium significantly reduced signal intensity and delayed uptake kinetics (FIG. 8) which is what would be expected if a competition for uptake between oleate and FFA-luc was occurring in the small intestine, again supporting the hypothesis that the FFA-luc compound mirrors physiological uptake processes.

Figure 9:
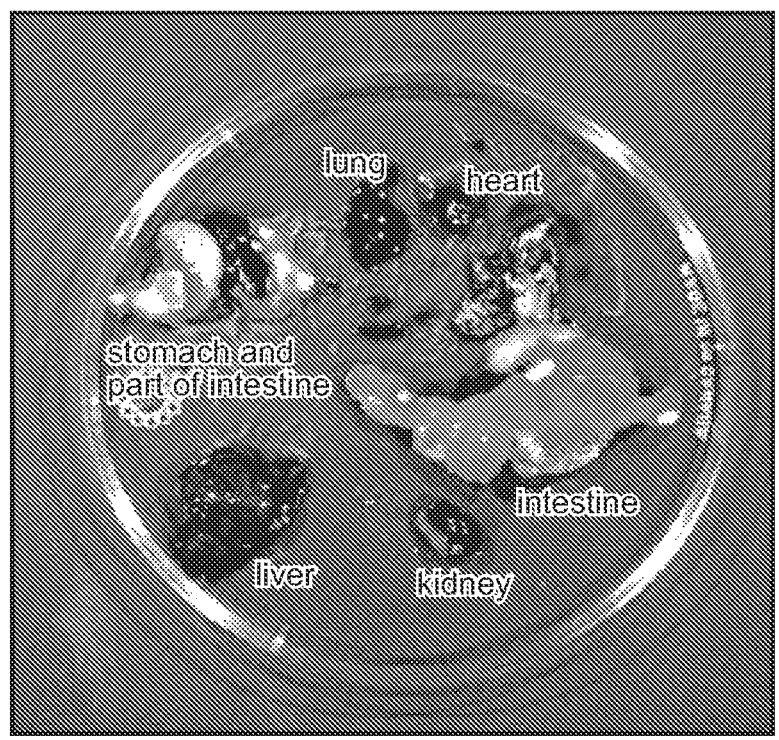
FIG. 9 illustrates bioluminescence from removed organs following oral gavage of FFA-luc demonstrating a strong signal from the small intestine, the principal site of FFA absorption, but none from the stomach, colon or other organs.

To verify that the signal was indeed emanating from the small intestine, animals were euthanized and dissected following oral gavage of FFA-luc. FIG. 9 shows that the small intestine was emitting a robust signal while the stomach and colon were negative. This is an important further argument for specificity as FFA-luc was in contact with all three parts of the GI system. However, physiological FFA absorption is only thought to occur in the small intestine as confirmed by the imaging studies presented herein.

Figure 10:
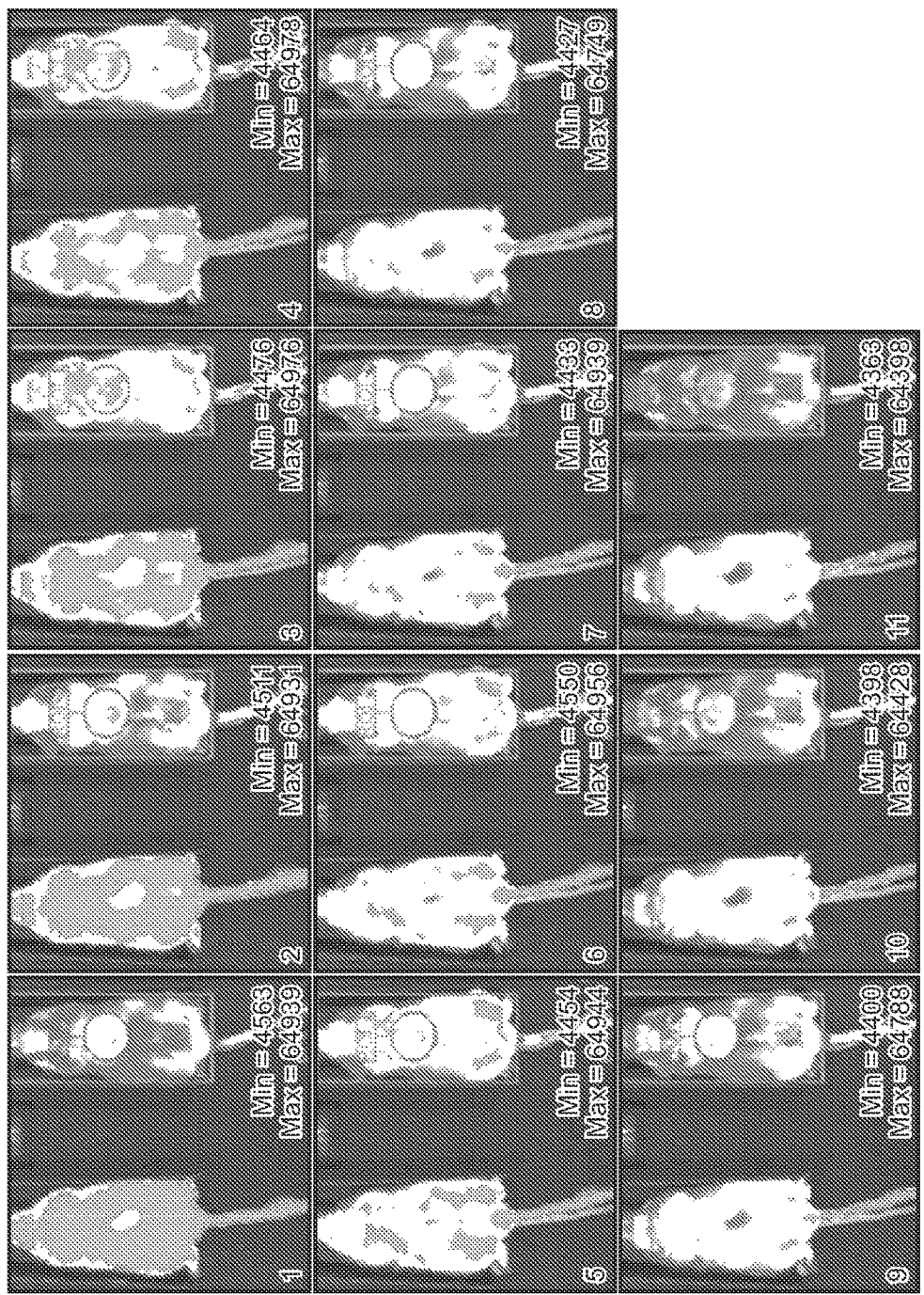
FIG. 10 illustrates in vivo imaging signal from mice injected intravenously with either luciferin alone (left mouse) or FFA-luc probe bound to albumin (right mouse). The time difference between each picture is 5 minutes. The sequence shows that while luciferin caused a strong and delocalized signal, FFA-luc showed a more specific and localized signal from the area of the heart, an organ known for its high fatty acid uptake and oxidation rate, with a rapid increase of signal followed by a slow decrease (see FIG. 11 for quantitation of results) consistent with rapid uptake of FFA-luc and slow depletion of the substrate from the circulation.
Figure 11:
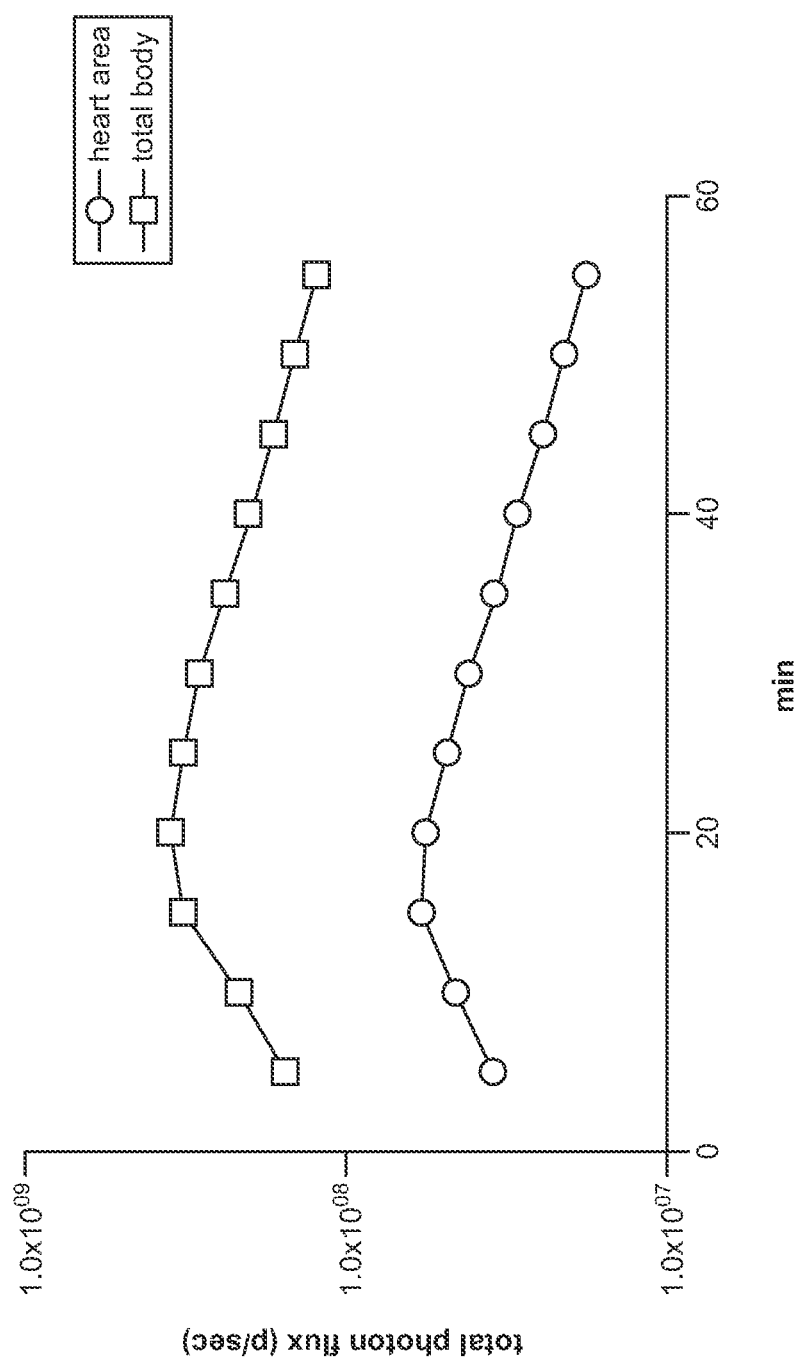
FIG. 11 illustrates the kinetics of photon flux from the heart and whole body area (areas shown in FIG. 10) from mice injected with FFA-luc demonstrating uptake kinetics that are consistent with the expectations for cardiac FFA utilization and slow depletion of substrate from the circulation.
Figure 12:
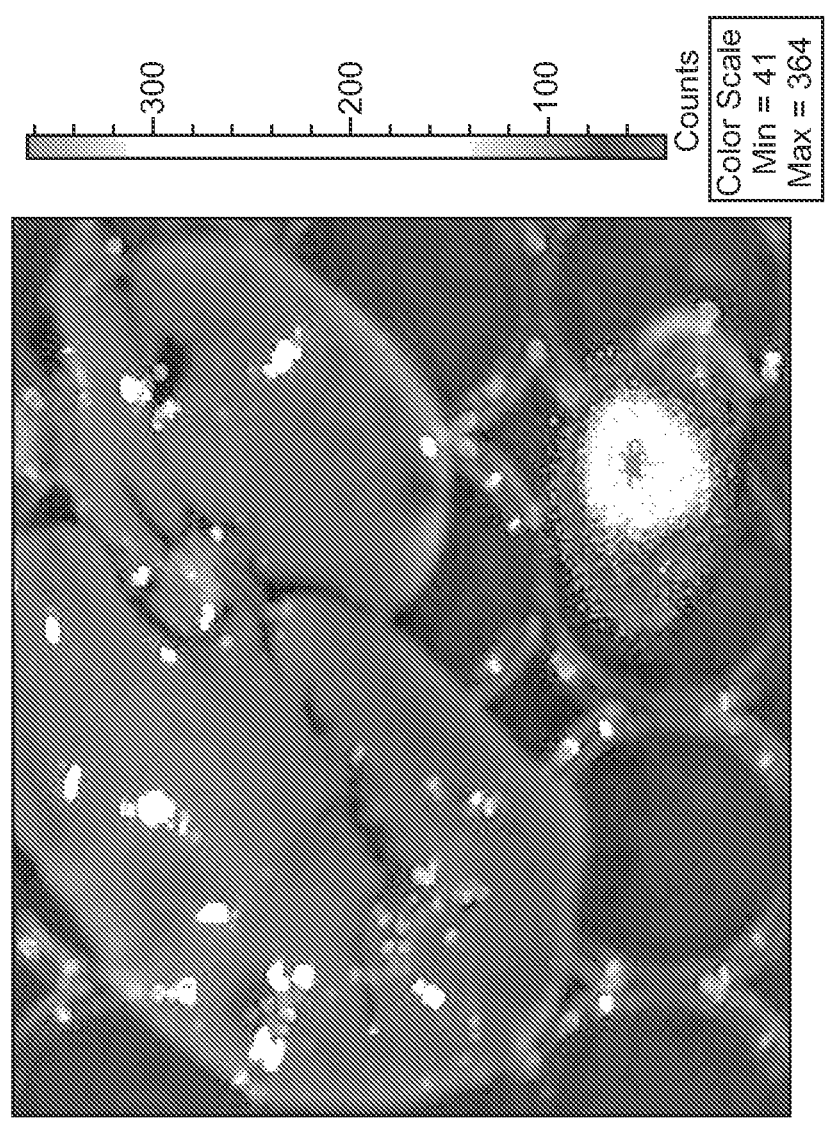
FIG. 12 illustrates the photon emissions from isolated organs following intravenous injection of FFA-luc, demonstrating high signal from the heart but low signal from liver.
Figure 13:
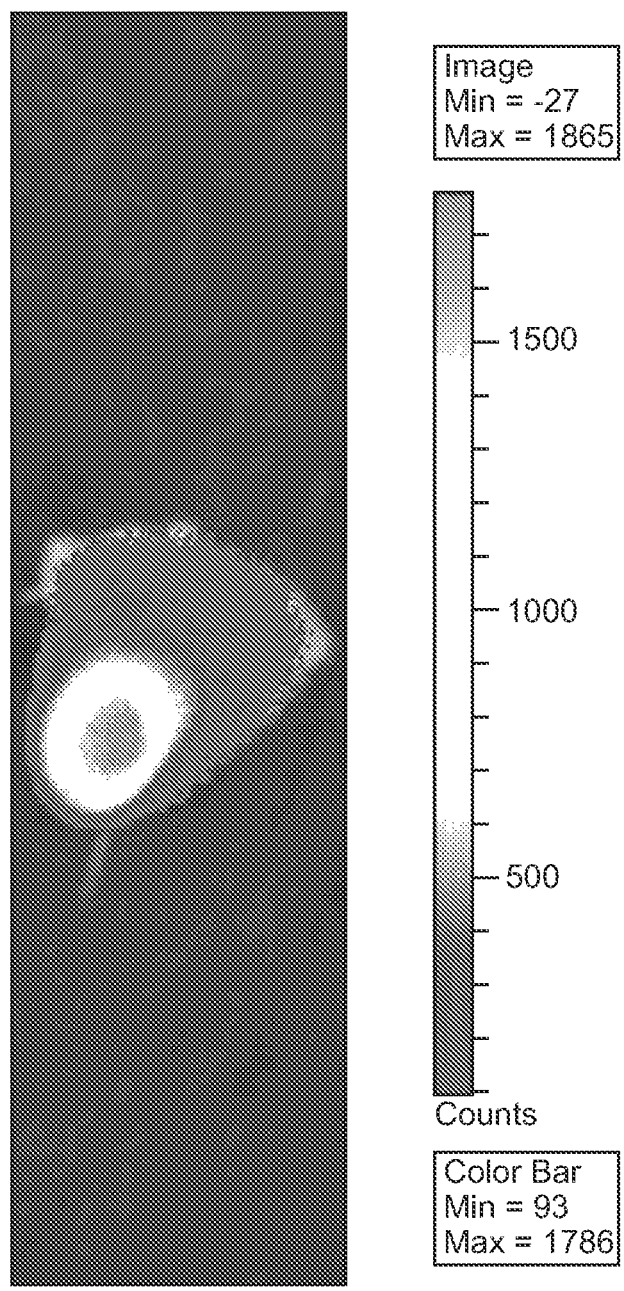
FIG. 13 illustrates the photon emissions from isolated interscapula brown adipose tissue (BAT) following intravenous injection of FFA-luc demonstrating high signal from this metabolically active tissue thus demonstrating that BAT FFA uptake can be imaged using this approach.

To monitor uptake of FFA-luc by internal organs, FFA-luc was bound to the physiological carrier of fatty acids in the serum, i.e. albumin. As a control, animals were injected with an albumin luciferin mix. While luciferin injections showed a very rapid, bright, and delocalized signal (FIG. 10, left mouse), FFA-luc showed slower kinetics with light being emitted particularly by the region of the heart (FIG. 10, right mouse). FIG. 11 shows kinetics of photon flux from the heart and whole body area (areas shown in FIG. 10) from mice injected with FFA-luc. These kinetics are consistent with the expectations for cardiac FFA utilization and slow depletion of substrate from the circulation. Further, it was confirmed with isolated organs that the strong signal from the upper left body cavity was indeed generated by the heart (FIG. 12). Finally, the interscapular brown adipose tissue was removed, an organ used for non-shivering thermogenesis, that is know to have a high FFA oxidation rate. Indeed, this organ also showed a robust light production following FFA-luc injection (FIG. 13), demonstrating the possibility of detection of physiological and pharmacological modulators of BAT FFA utilization.

Example 5

Methods and Materials

Luciferase expressing cellular model (3T3-L1-Luc Cells): 3T3-L1 fibroblasts (ATCC) were stably transfected with the pGL4.51[luc2/CMV/Neo] vector (Promega). Clones with the highest level of luciferase expression were isolated and expanded.

Cell culture and treatment: 3T3-L1-luc fibroblasts were grown in DMEM containing 10% fetal bovine serum with 2 mM L-glutamine and 1% penicillin/streptomycin (DMEM/FBS). A cell differentiation protocol was followed as previously described (Baldini et al., Cloning of a Rab3 isotype predominantly expressed in adipocytes. Proc Natl Acad Sci USA 89, 5049 (Jun. 1, 1992); Stahl et al., Insulin causes fatty acid transport protein translocation and enhanced fatty acid uptake in adipocytes. Dev Cell 2, 477 (2002)). Specifically, differentiated cells were generated by treating fibroblasts 48 hours post-confluency with DMEM/FBS supplemented with 0.83 µM insulin, 0.25 µM dexamethasone, and 0.25 mM IBMX for 48 hours, then DMEM/FBS supplemented with 0.83 µM insulin for 48 hours, followed by maintenance in DMEM/FBS for an additional 48-72 hours. Differentiated cells were used in experiments on days 8-12 of differentiation.

Animal models: Transgenic mice ubiquitously expressing luciferase under control of the actin promoter were used.

Imaging equipment and software: All luminescent/photographic images were captured with the IVIS Spectrum (Caliper Life Sciences). Total flux (photons/sec) of regions of interest were calculated with the IVIS Living Image software. CT data was acquired with the Quantum FX µCT (Caliper Life Sciences).

Cell-based fatty acid uptake assays: 3T3-L1-luc adipocytes or fibroblasts were seeded into black-wall/clear-bottom-96-well plates (Costar) and treated with 100 µl of a fatty acid uptake buffer consisting of 0.1% BSA in Hank's balanced salt solution (HBSS) in addition to 2-100 µM of the compound. Plates were read immediately and luminescent images were acquired with a 5-minute exposure time back to back for 60 minutes. All cell-based assays utilized the same kinetic acquisition settings.

FFA-SS-Luc competition assay: 3T3-L1-luc adipocytes were seeded into black-wall/clear-bottom-96-well plates (Costar) and treated with 100 µl fatty acid uptake buffer including 20 µM FFA-luc and a titration of 0-2 mM oleate or methyl-oleate immediately prior to imaging.

Insulin-mediated uptake of FFA-luc: 3T3-L1-luc adipocytes were seeded into black-wall/clear-bottom-96-well plates (Costar). One group of cells was serum starved in DMEM for 5 hours followed by the addition of 1000 fatty acid uptake buffer with 20 µM FFA-luc immediately prior to imaging. A second group of cells was treated with DMEM/fetal bovine serum (FBS) for 5 hours followed by the addition of 100 µl fatty acid uptake buffer with 20 µM FFA-luc and 1 ug/mL insulin immediately prior to imaging.

Gavage of FFA-luc and FFA-S-luc: Anesthetized mice received a 50 µl volume gavage of 300 µM FFA-luc or FFA-S-luc (0.01 mg) in a vehicle of 1:1 PEG 400 and propylene glycol. Mice were awake for 5 minutes post-gavage to stimulate peristalsis before they were re-anesthetized for imaging. Mice were under constant isoflurane administration in the IVIS Spectrum In Vivo Imager and luminescent images were acquired with a 5-minute exposure back to back for 60 minutes.

Intravenous injection: Restrained mice received 100 µl volume tail vein injections of 20 µM FFA-luc or FFA-S-luc (0.0014 mg) bound to 0.1% bovine serum albumin (BSA) in phosphate buffered saline (PBS). Mice were immediately anesthetized and luminescent images with a 1-minute exposure were acquired.

Intraperitoneal injection: Anesthetized mice received a 100 µl volume intraperitoneal injection of 200 µM FFA-luc or FFA-S-luc (0.014 mg) bound to 0.1% BSA in PBS immediately prior to imaging. Luminescent images were acquired with a 3-minute exposure back to back for 30-minutes.

BAT imaging: Anesthetized mice received 100 µl volume intraperitoneal injection of 200 µM FFA-luc (0.014 mg) immediately prior to imaging. Luminescent images were acquired with a 3-minute exposure back to back for 30-minutes. For BAT activation imaging, mice received intraperitoneal injections of the β-adrenergic stimulator CL316,243 at 1 mg/kg 20 minutes prior to the FFA-luc injection.

CT scans: Mice received a 100 µl volume gavage of 80 mg barium sulfate. After one hour, mice received a second barium sulfate gavage, immediately followed by a 50 µl volume gavage of 300 µM FFA-luc (0.01 mg) in a vehicle of 1:1 PEG 400 and propylene glycol. Mice were placed in a Mouse Imaging Shuttle Adaptor (Caliper Life Sciences) and luminescent images were acquired with a 5-minute exposure back to back for 60 minutes. Mice were then transferred to the Quantum FX µCT for CT imaging without disruption of position. Co-registration of luminescent and CT images were performed with Living Image software.

Results

Figure Legends

FIG. 16: Characterization of fatty acid probe uptake in vitro. A) Uptake kinetics of FFA-luc at the indicated concentrations by 3T3-L1 adipocytes. B) Uptake rate of FFA-luc, methyl-FFA-luc, and luciferin (each at 20 µM) over a 30 minute time course. C) Concentration-dependent inhibition curve of oleate against uptake of 20 µM FFA-luc by 3T3-L1 adipocytes ($IC_{50}$=17 µM). D) As (C), but with methyl-oleate. E) Uptake kinetics of 20 µM FFA-luc by 3T3-L1 adipocytes with or without a 5-hour pre-incubation with 5 µg/ml insulin.

FIG. 17: Uptake of FFA-luc by the small intestine in L2G85 mice. A) Ventral luminescent/photographic overlay sequence of animals following a gavage with 100 µl FFA-luc (20 µM) in cremophor. Scale min: 1.64e5 p/s and max: $2.60e^6$ p/s. B) Luminescent/µCT overlay of FFA-luc uptake by the small intestine following 2 barium sulfate administrations (80 mg each over 1 h) and gavage with 50 µl FFA-luc (300 µM) in 1:1 PEG 400 and PG. Bioluminescent signal was imaged for 1 h followed immediately by a µCT scan. 3D data sets from both imaging modalities were overlaid using Living Image 4.1 software. C) Luminescent/photographic overlay of excised GI tract one hour after gavage with 50 µl of a 300 µM FFA-luc (0.01 mg) solution in 1:1 PEG 400 and PG. Scale min: $9.8e^4$ p/s and max: $3.37e^5$ p/s. Numbers indicate 1: stomach; 2: duodenum; 3: colon. D) Ventral luminescent/photographic overlay comparing the bioluminescence imaging (BLI) of FFA-luc (right) and the control FFA-S-luc (left) 20 minutes post-gavage. Mice were gavaged with 50 µl of a 300 µM solution of either compound (0.01 mg) in 1:1 PEG 400 and PG. Scale min: $3.74e^5$ p/s and max: $4.52e^4$ p/s.

FIG. 18: Uptake of FFA-luc following injection into L2G85 mice. A) Ventral luminescent/photographic overlay of mouse five minutes after tail vein injection of FFA-luc (100 µL of a 20 µM solution bound to 0.1% BSA in PBS). Scale min: $8.04e^3$ p/s and max: $1.54e^5$ p/s. B) Luminescent/photographic overlay of FFA-luc uptake by (I.) white adipose tissue (WAT), (II.) liver, (III.) kidneys, (IV.) heart, and (V.) skeletal muscle, excised from L2G85 mice five minutes after FFA-luc administration as in A). C) Ventral luminescent/photographic overlay of intact (I.-III.) and excised (IV-VI.) BAT 30 minutes after IP injection of 100 µl of a 0.1% BSA PBS solution containing either 20 µM FFA-S-luc (I/IV), FFA-luc (II/V), or FFA-luc with 1 mg/kg of the β-adrenergic agonist CL316243 (III/VI). I-III scale min: $2.62e^5$ p/s and max: $5.02e^6$ p/s. IV-VI scale min: $1.85e^4$ p/s and max: $8.34e^5$ p/s. D) BAT uptake kinetics of FFA-S-luc (triangles), FFA-luc (circles), and FFA-luc+1 mg/kg CL316243 (red squares). All compounds were administered as stated in (C). BLI images were acquired every three minutes immediately after compound administration. FFA uptake rate by BAT was calculated by drawing regions of interest around the interscapular region of each mouse.

Figure 19:
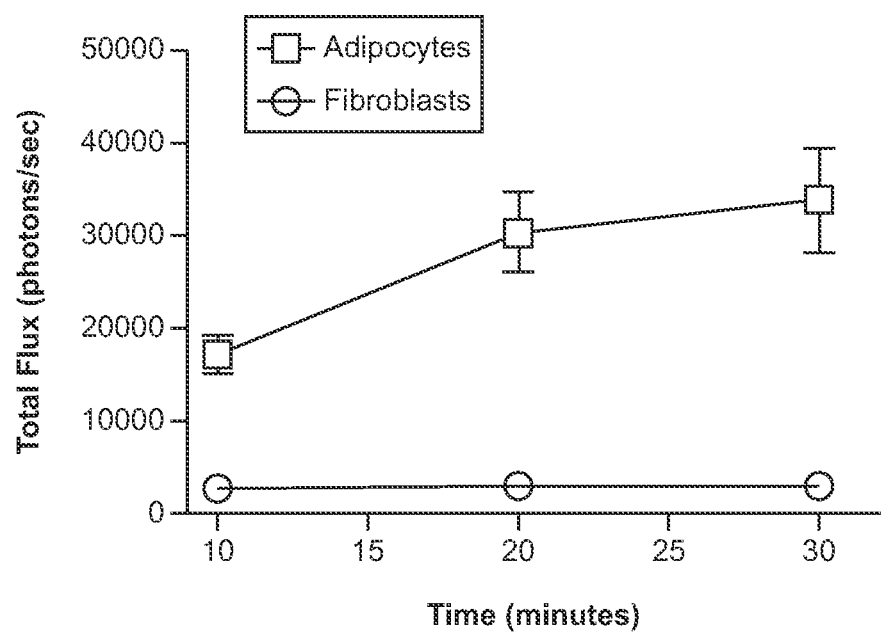
FIG. 19 depicts FFA-luc uptake by 3T3 L1 adipocytes and fibroblasts.

FIG. 19: FFA-luc uptake by 3T3 L1 adipocytes and fibroblasts. Uptake of 20 µM FFA-luc by luciferase expressing undifferentiated fibroblasts or 3T3 L1 adipocytes over 30 min.

Figure 20:
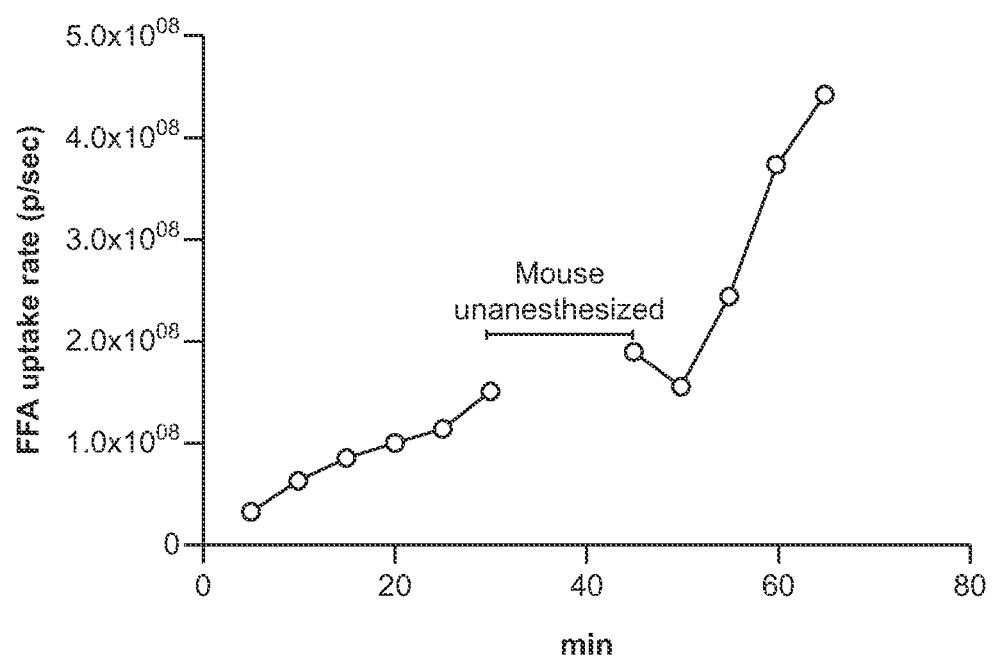
FIG. 20 depicts the kinetics of intestinal fatty acid absorption.

FIG. 20: Kinetics of intestinal fatty acid absorption. Quantitative analysis of a ventral luminescent/photographic overlay sequence of animals following a gavage with 100 µl compound 1 (20 µM) in cremophor (see FIG. 17A) using a region of interest over the animal's mid-section.

Based on fatty acid transporter (FATP) substrate specificity (A. Stahl et al., Identification of the major intestinal fatty acid transport protein. Mol Cell 4, 299 (September, 1999)), a >10 carbon, even numbered, unbranched and non-esterified FFA was selected as a lipid probe. The fatty acid was connected via a disulfide linker to luciferin as these linkers are stable outside of cells following injections into animals (Dubikovskaya et al. Overcoming multidrug resistance of small-molecule therapeutics through conjugation with releasable octaarginine transporters. Proc Natl Acad Sci USA 105, 12128 (Aug. 26, 2008); L. R. Jones et al., Releasable luciferin-transporter conjugates: tools for the real-time analysis of cellular uptake and release. J Am Chem Soc 128, 6526 (May 24, 2006); P. A. Wender et al., Real-time analysis of uptake and bioactivatable cleavage of luciferin-transporter conjugates in transgenic reporter mice. Proc Natl Acad Sci USA 104, 10340 (Jun. 19, 2007).). A non-toxic probe was utilized that upon liberation from the linker is activated by taking advantage of the fact that luciferin derivatives alkylated on the phenolic oxygen do not generate light (Denburg et al., Substrate-Binding Properties of Firefly Luciferase. Arch Biochem Biophys 134, 381 (1969)). Thus free luciferin is only generated and measured following disulfide linker reduction followed by thiol cylization. Free luciferin is then converted by luciferase to oxyluciferin and a photon of light (Jenkins et al., Bioluminescent imaging (BLI) to improve and refine traditional murine models of tumor growth and metastasis. Clin. Exp. Metastasis 20, 733 (2003)) (FIG. 1), facilitating real-time non-invasive detection of FFA uptake using bioluminescent imagers with an excellent signal-to-background ratio and the possibility of spatial localization of signal generating organs.

Figure 16A:
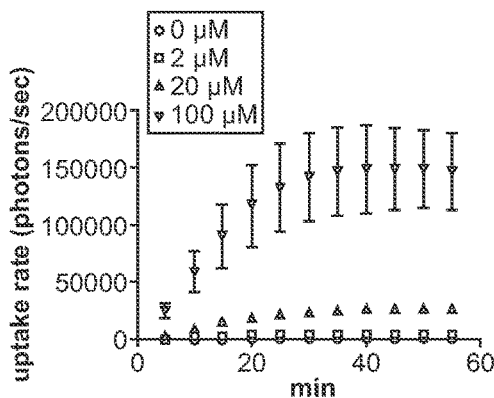
FIGS. 16A-16E depict the characterization of fatty acid probe uptake in vitro.
Figure 16B:
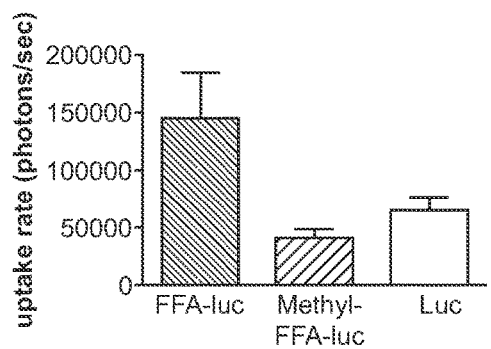
Figure 16C:
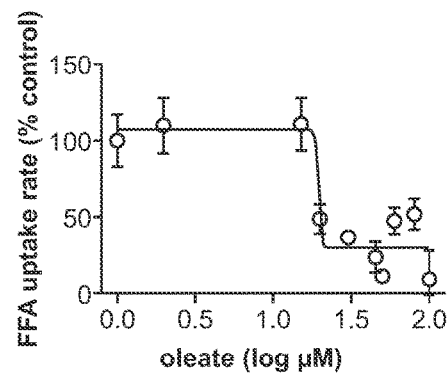
Figure 16D:
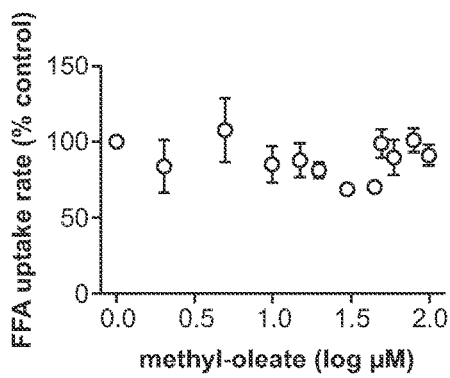

To determine the physiological parameters of cellular uptake, BSA-bound FFA-luc was added to luciferase-expressing 3T3 L1 adipocytes at a final concentration of 0-100 µM. This led to a robust, dose-dependent signal (FIG. 16A). In contrast, the uptake kinetics by undifferentiated fibroblast-like 3T3 L1 cells, which lack FATP expression, were significantly lower (FIG. 19). To further demonstrate physiological uptake, a methyl ester of FFA-luc, termed methyl-FFA-luc, was generated which should not be a substrate for FFA transporters (A. Stahl et al., Identification of the major intestinal fatty acid transport protein. Mol Cell 4, 299 (September, 1999)). Indeed both methyl-FFA-luc and unconjugated free luciferin showed significantly lower uptake rates in adipocytes compared to FFA-luc (FIG. 16B). Most importantly, FFA-luc inhibited uptake by adipocytes with an excess of oleate, but not methyl-oleate, demonstrating that the uptake process for the imaging compound overlaps with that of natural fatty acid substrates (FIG. 16C-D).

Figure 16E:
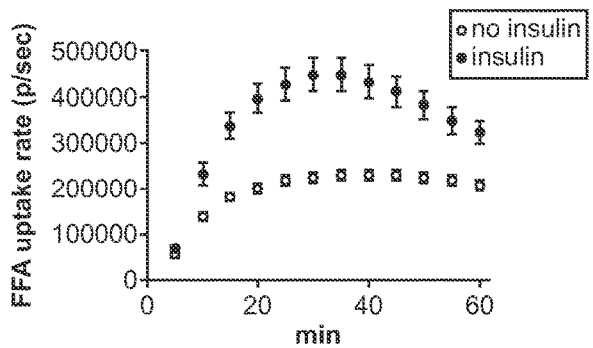

Physiological uptake of FFA-luc was further supported by reproducing the known stimulatory effect of insulin on FFA uptake (Q. Wu et al., FATP1 is an insulin-sensitive fatty acid transporter involved in diet-induced obesity. Mol Cell Biol 26, 3455 (May, 2006)). Changes in FFA uptake rates were monitored in real time immediately following insulin addition (FIG. 16E). The use of BLI, unlike other imaging methods, permitted monitoring of both signal increase and dissipation. The non-cumulative nature of the light signal generated upon uptake allowed clear detection of the decrease in FFA uptake rates. By contrast, traditional fluorescence or radio imaging methods produce signals that accumulate over time and thus make the detection of dynamic changes accompanying prolonged imaging more challenging.

After validation of FFA-luc in cultured adipocytes, its capabilities were tested in mice expressing luciferase under the control of the actin promoter (FIG. 17-18). Oral delivery of FFA-luc using cremophor, polyethylene glycol (PEG) 400, and 1:1 mixtures of PEG/PG as delivery vehicles all showed an abdominal signal as shown in FIG. 17A with uptake kinetics that slowly increased over the time frame of hours (FIG. 20), in line with expected kinetics of intestinal FFA absorption (Niot et al., Intestinal absorption of long-chain fatty acids: evidence and uncertainties. Progress in lipid research 48, 101 (March, 2009)). To verify that the signal was indeed emanating from the small intestine, multimodal imaging was performed with BLI and CT utilizing barium sulfate as a contrast reagent to highlight the GI tract (FIG. 17B). Coregistered overlays of the CT and BLI images (following 3D localization of the signal with diffuse luminescent imaging tomography (Kuo et al., Three-dimensional reconstruction of in vivo bioluminescent sources based on multispectral imaging. J Biomed Opt 12, 024007 (March-April, 2007))) show that the signal is indeed generated by FFA-luc in the small intestine (FIG. 17B). This was further confirmed by excising the GI tract from the stomach to the colon. Importantly, the strongest signal was generated by the proximal duodenum (FIG. 17C 2) while the stomach (FIG. 17C 1) and colon (FIG. 17C 3) were negative. This observation is in excellent agreement with the known pattern of long-chain fatty acid absorption in murine and human intestine (Goodman, Insights into digestion and absorption of major nutrients in humans. Adv Physiol Educ 34, 44 (June, 2010)) and highlights the specificity of uptake, as the stomach is negative in spite of receiving the largest dose of FFA-luc.

Figure 17C:
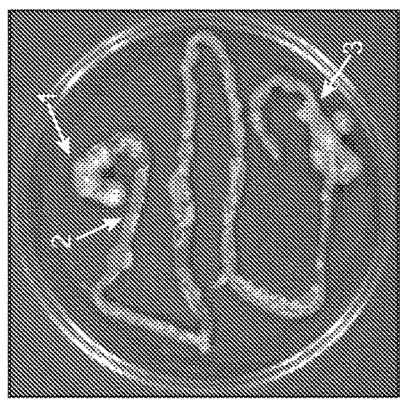
FIGS. 17A-17D depict the uptake of FFA-luc by the small intestine in mice.
Figure 17D:
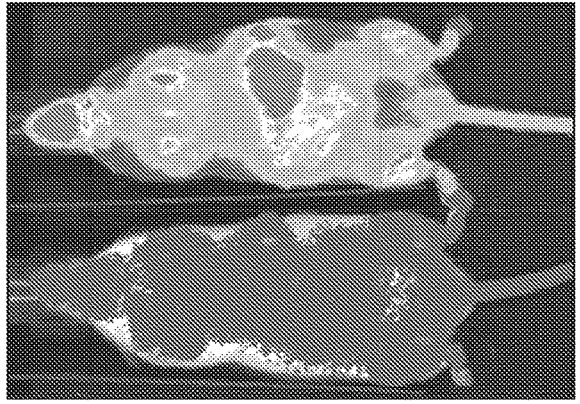
Figure 17A:
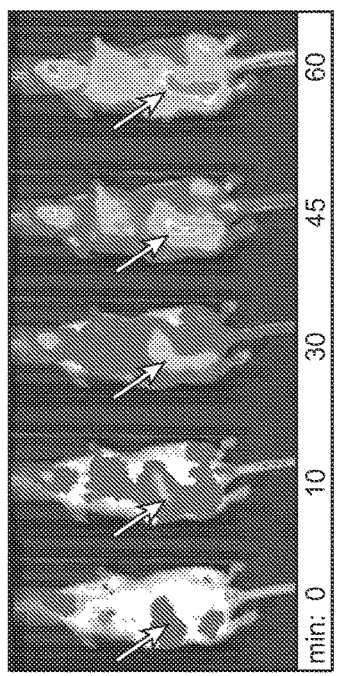
Figure 17B:
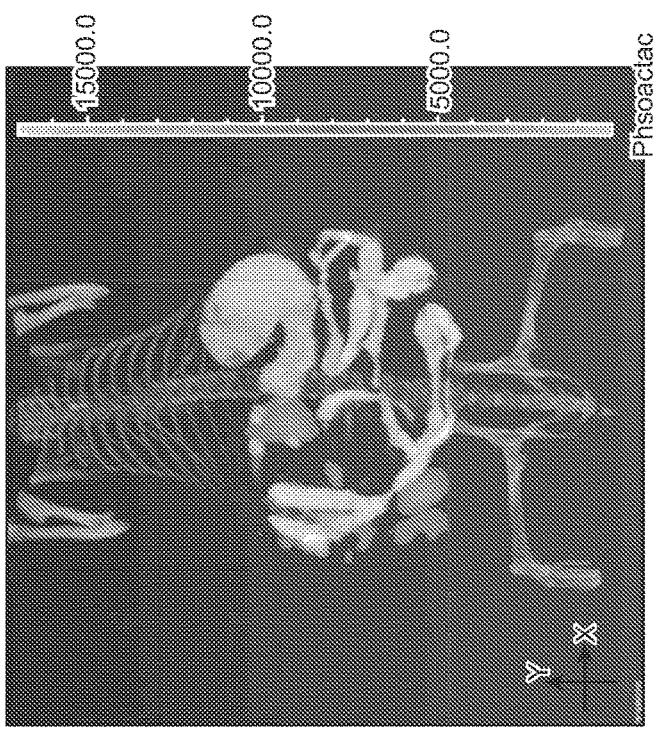

The mechanism of BLI generated by FFA-luc was further validated using control compound FFA-S-luc, which lacks a cleavable linker and instead includes a single sulfide bond. Using the same procedures as with FFA-luc, a weak and diffuse signal was observed upon oral gavage of control compound FFA-S-luc (FIG. 17D).

To further demonstrate the versatility of the method, FFA-luc (20 μM) was bound to 0.1% BSA and injected intravenously into the tail vein of mice globally expressing luciferase and the mice were imaged immediately. FFA-luc rapidly generated strong signals from the upper body cavity and the leg musculature (FIG. 18A). As expected for a natural long-chain fatty acid, FFA-luc was taken up by several organs as confirmed ex vivo. Particularly, the adipose tissue, liver, kidneys, heart and skeletal muscle strong signals (FIG. 18B 1-V) in line with known fuel and FFA uptake preferences. Using the actin promoter luciferase transgenic mice, a robust light signal was detected from the BAT area (see arrows in FIG. 18C) that increased in intensity over the initial 20 minutes following the intraperitoneal injection of compound 1 (FIG. 18D). Excision of the BAT confirmed that the signal in the interscapular area was indeed emanating from the BAT pads (FIG. 18C IV-VI) while little or no signal from intact (FIG. 18C I) or excised (FIG. 18C IV) BAT was seen following injection of compound 3, confirming the specificity of the imaging reagent. β-adrenergic stimulation enhances FFA uptake by BAT in a FATP1-dependent fashion (Wu et al., Fatty acid transport protein 1 is required for nonshivering thermogenesis in brown adipose tissue. Diabetes 55, 3229 (December, 2006)). Importantly, injection of the β-3 adrenergic stimulator, CL316,243, led to a highly reproducible and significant increase in compound 1 uptake by BAT (FIG. 18C II/V vs. III/VI). The β-3 adrenergic agonist-induced changes in BAT bioluminescence were highly reproducible in a cohort of 16 animals (FIG. 4D), demonstrating detection in vivo of physiologically meaningful quantitative changes in the spaciotemporal flux of fatty acids in real time.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound of the formula:

Q-L-X—Y wherein Q is a lipid;
X is an optional leaving group;
L is a cleavable linker comprising a cleavable bond that provides for release of Y or X—Y following cleavage of the linker; and
Y comprises a detectable moiety that, after release, generates a direct or indirect detectable signal wherein Y is selected from a luciferin, an aminoluciferin, coelenterazine, a modified coelenterazine, a coelenterazine analog, a membrane permeant coelenterazine analog, a dihydroluciferin, a luciferin 6' methylether, a luciferin 6' chloroethylether;

wherein L is described by one of the following structures:

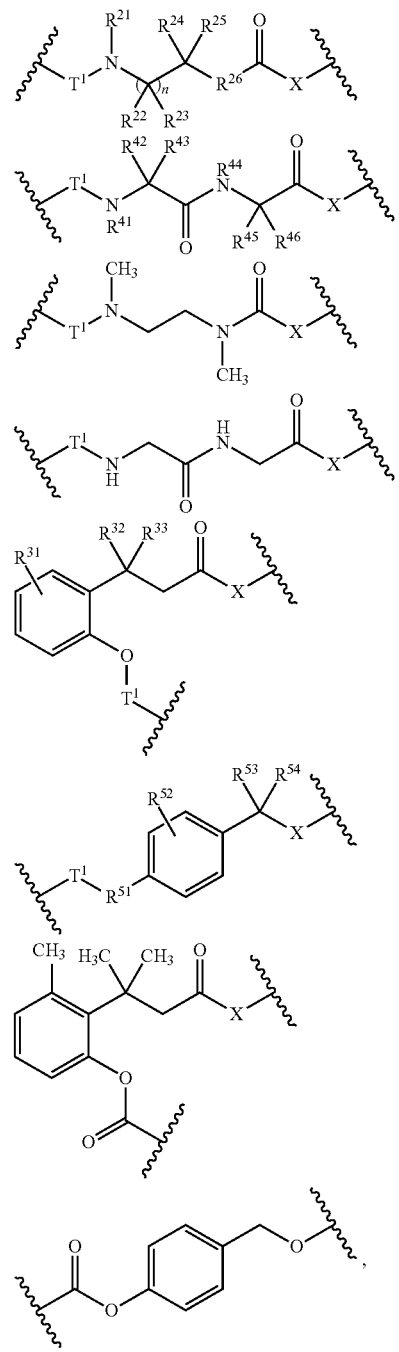

wherein:
n is 1, 2 or 3;
$R^{26}$ and $R^{51}$ are independently selected from O, S and NR, where R is hydrogen or alkyl;
$T^1$ is a single bond or a linking group that is bound to Q;
$R^{31}$ and $R^{52}$ are independently one or more groups, each $R^{31}$ and $R^{52}$ independently selected from H, an alkyl, an aliphatic, an amino, an aryl, an acyl, an alkoxy, an aryloxy, an acyloxy, a carbonyl, a cyano, a halogen, hydroxyl, a heterocyclic group, a nitro, a thio, a sulfinyl, a sulfonyl and trifluoromethyl; and $R^{21}$, $R^{22}$, $R^{23}$, $R^{24}$, $R^{25}$, $R^{32}$, $R^{33}$, $R^{41}$, $R^{42}$, $R^{43}$, $R^{44}$, $R^{45}$, $R^{46}$, $R^{53}$ and $R^{54}$ are independently selected from hydrogen, an alkyl, an aryl, a heterocyclic group and an amino acid sidechain group.

2. The compound of claim 1, wherein:

Q is selected from an unsaturated fatty acid, a polyunsaturated fatty acid, a saturated fatty acid, an essential fatty acid, a trans fatty acid, a glycerolipid, a triglyceride, a diglyceride, a monoglyceride, a fatty acid, a sterol, an oxisterol, a cholesterol ester, cholesterol, a bile acid, a steroid hormone, a vitamin derived fatty acid, vitamin E, vitamin K, a phospholipid, a sphingolipid, a ganglioside, a prenol lipid, a carotenoid, and a ubiquinone.

3. The compound of claim 1, wherein:

L comprises an enzyme substrate and is cleaved using an enzyme.

4. The compound of claim 1, wherein:

L is susceptible to cleavage under particular physiological conditions selected from reducing conditions, oxidizing conditions, acidic pH, and basic pH.

5. The compound of claim 1, wherein:

cleavage of the cleavable bond of linker L unmasks a functional group that triggers the release of Y or X—Y.

6. The compound of claim 1, wherein:

upon cleavage of the cleavable bond of linker L, a nucleophilic moiety is unmasked, that provides for intramolecular reaction at an electrophilic site adjacent to the leaving group X leading to the release of X—Y.

7. The compound of claim 1, wherein:

L is described by the structure:

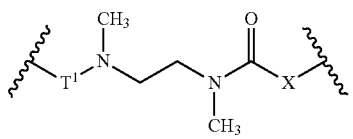

wherein;

$T^1$ is a single bond or a linking group that is bound to Q; and

X is O or S.

8. The compound of claim 1, wherein:

Y comprises:

a) an optionally substituted luciferin moiety, where luciferin moiety has one of the following structures:

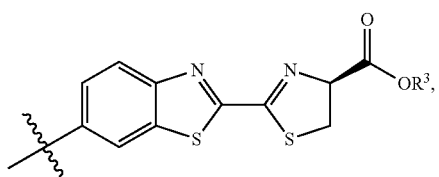

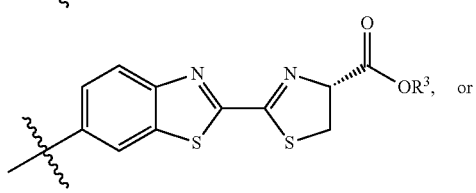

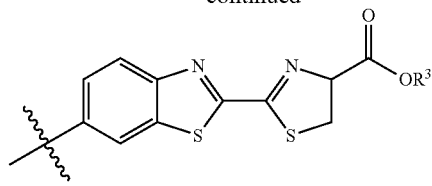

wherein $R^3$ is hydrogen, alkyl or substituted alkyl;

b) an optionally substituted coelenterazine moiety, wherein coelenterazine has the structure:

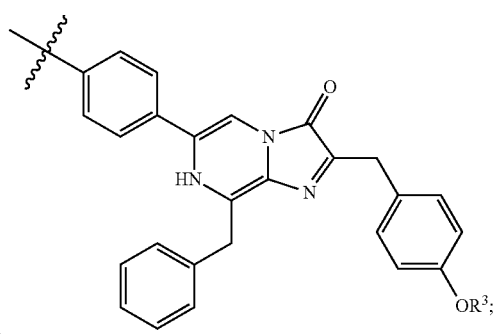

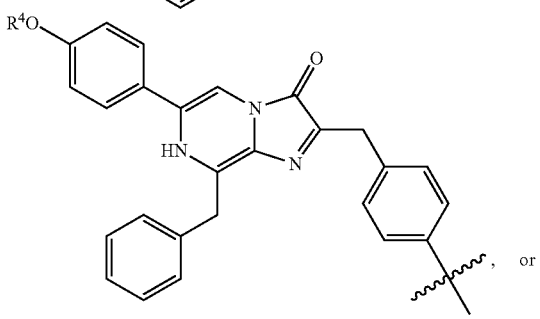

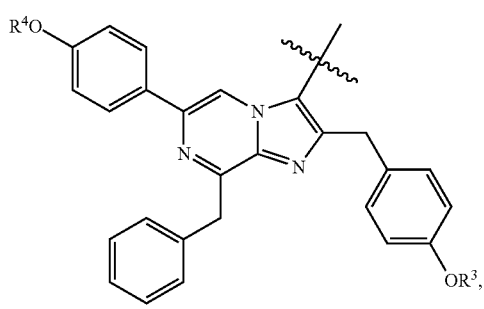

wherein $R^3$ and $R^4$ are independently selected from hydrogen, an acyl, an acyloxy, and an acylamino;

c) the following structure:

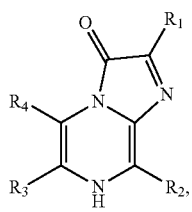

61 wherein $R^1$, $R^2$, $R^3$, and $R^4$ are independently H, alkyl, heteroalkyl, aryl, or combinations thereof, wherein the structure is attached to the linker via any one of $R^1$, $R^2$, $R^3$ and $R^4$;

d) an optionally substituted membrane-permeant coelenterazine moiety of one of the following structures:

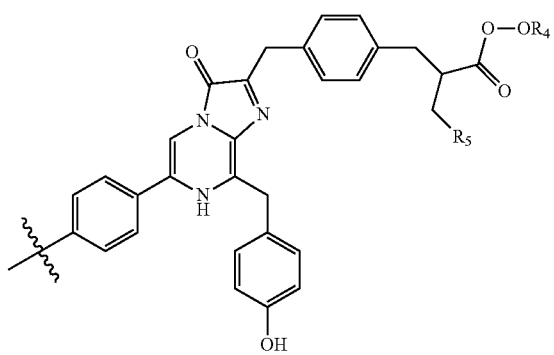

62

-continued

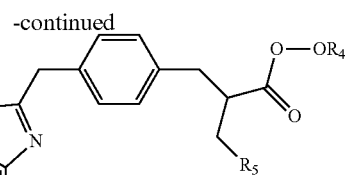

wherein $R_4$ and $R_5$ are independently an alkyl, an aryl, an aralkyl, an alkoxy, or a heterocyclic group;

e) an optionally substituted membrane-permeant coelenterazine moiety of one of the following structures:

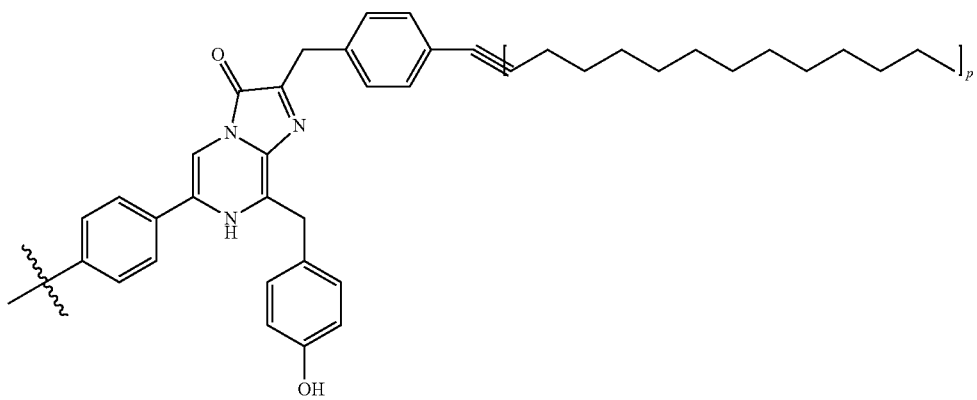

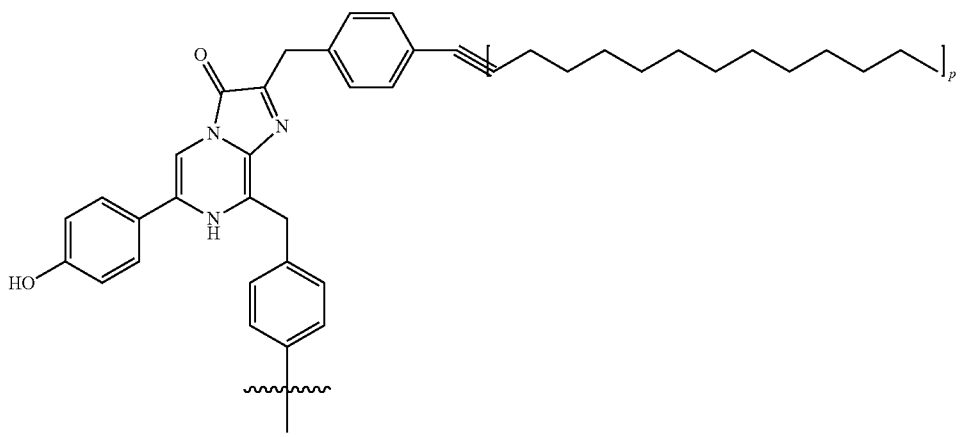

wherein p is an integer of about 1 to 20;

f) an optionally substituted membrane-permeant coelenterazine moiety of one of the following structures:
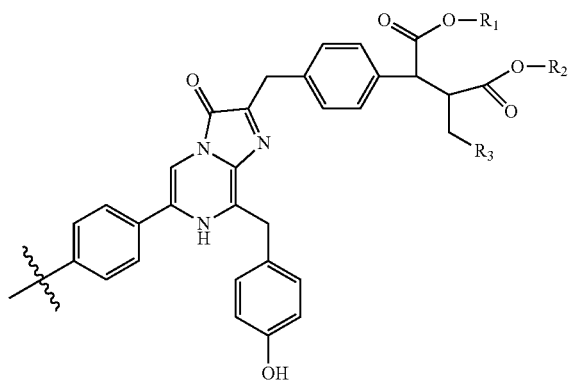
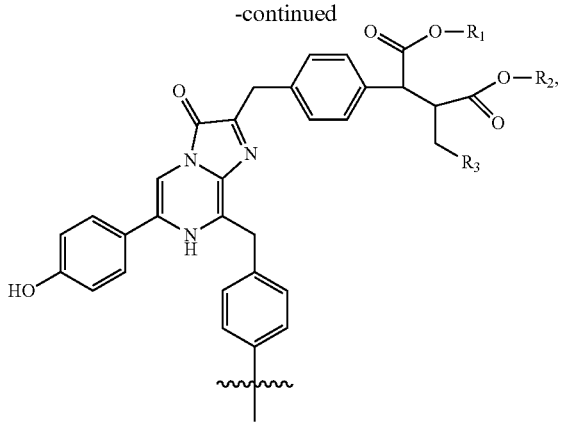
wherein $R_1$, $R_2$, and $R_3$ are independently an alkyl, an alkenyl, or an aralkyl;
g) an optionally substituted membrane-permeant coelenterazine moiety of one of the following structures:
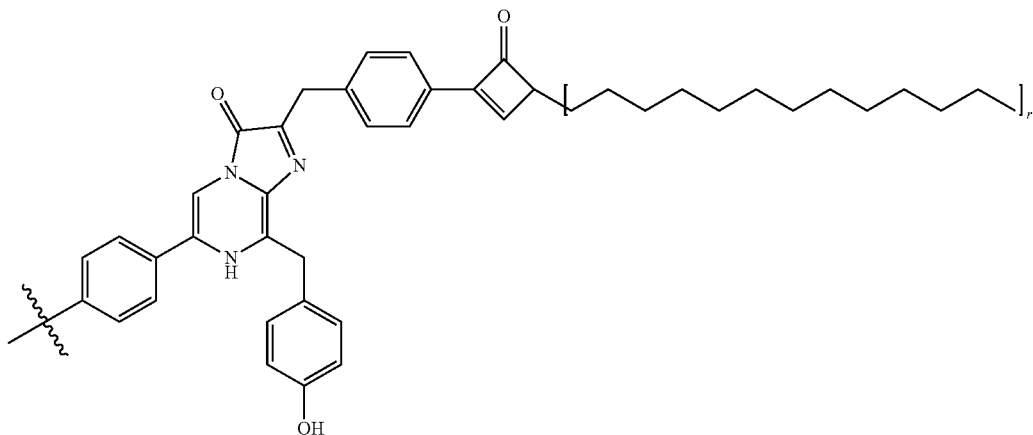
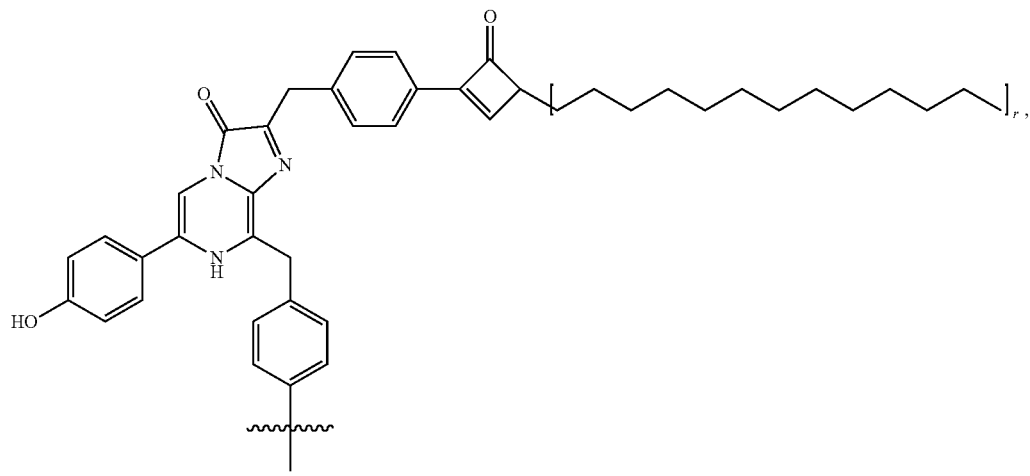
wherein r is an integer of about 1 to 20;

h) an optionally substituted membrane-permeant coelenterazine moiety of one of the following structures:

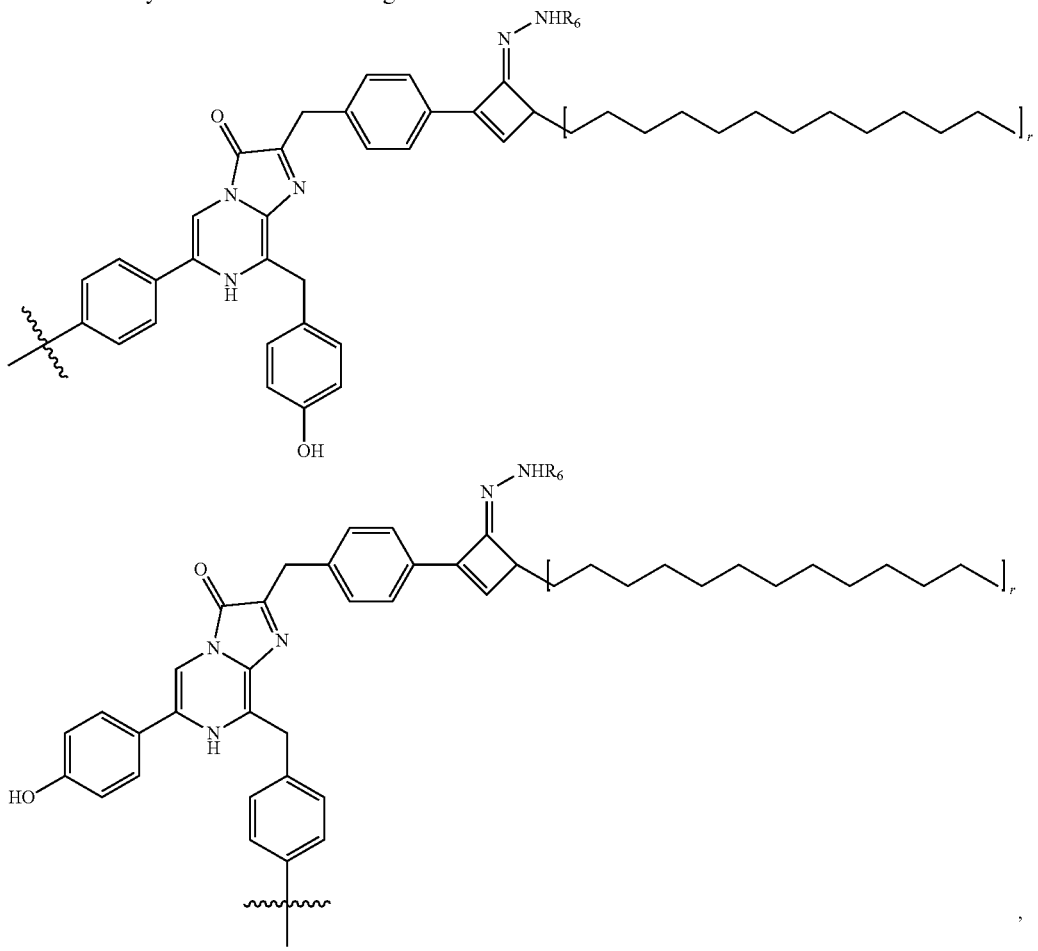

wherein r is an integer of about 1 to 20; and
R$^6$ is an alkyl, an aryl, an aralkyl, or an alkoxyalkyl;

i) one of the following structures:

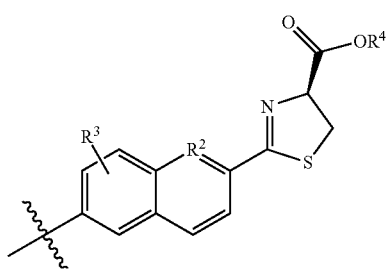

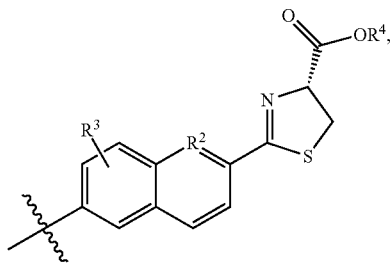

wherein R$^2$ is N or CH;

R$^3$ is hydrogen, a halo, an alkyl, an alkoxy, an amino, —CH$_2$N═R, or CH$_2$NRR', wherein R is alkyl and R' is alkyl; and R$^4$ is hydrogen, alkyl or substituted alkyl;

j) one of the following structures:

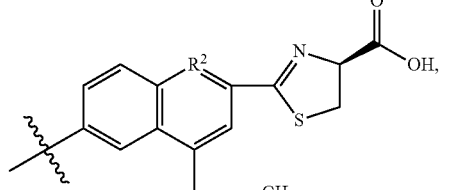

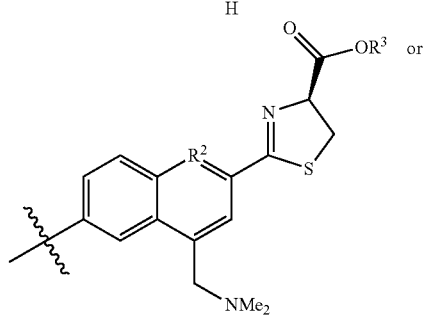

-continued

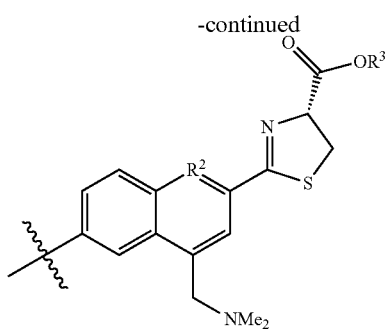

wherein R² is N or CH; and R³ is hydrogen, alkyl or substituted alkyl;

k) one of the following structures:

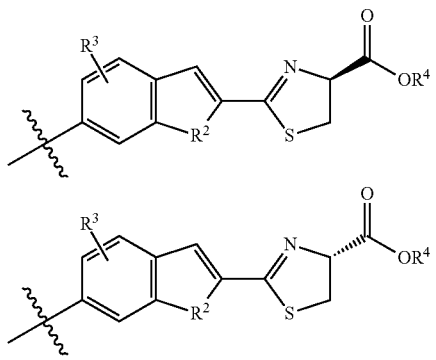

wherein R² is O or S;
R³ is hydrogen, a halo, an alkyl, an alkoxy, an amino, —CH₂N═R, or CH₂NRR', wherein R is alkyl and R' is alkyl; and
R⁴ is hydrogen, alkyl or substituted alkyl; or l) one of the following structures:

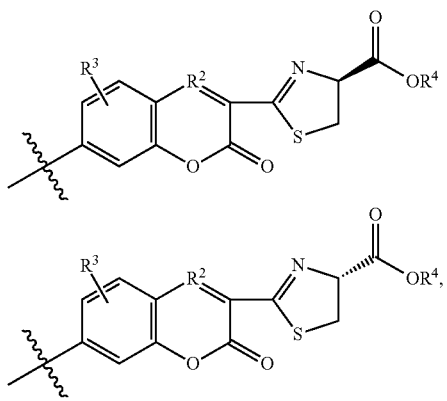

wherein R² is N or CH;
R³ is hydrogen, a halo, an alkyl, an alkoxy, an amino, —CH₂N═R, or CH₂NRR', wherein R is alkyl and R' is alkyl; and
R⁴ is hydrogen, alkyl or substituted alkyl.

9. The compound of claim 1, wherein:
release of Y produces a luciferin of one of the following structures:

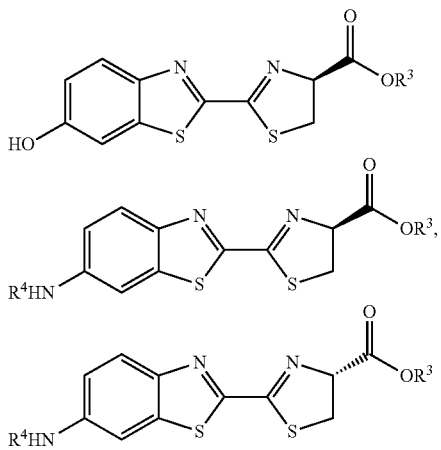

wherein R³ is hydrogen, alkyl or substituted alkyl; and R⁴ is hydrogen, alkyl, substituted alkyl or alkoxy.

10. The compound of claim 1, wherein:
Y comprises;
a) a contrast agent or a radioisotope suitable for use in imaging;
b) a detectable moiety that comprises $^{123}$I (iodine), $^{18}$F (fluorine), $^{99}$Tc (technetium), $^{111}$In (indium), and $^{67}$Ga (gallium), gadolinium (Gd), dysprosium, or iron;
c) a chelating ligand for a gadolinium ion;
d) a chelating ligand of the structure:

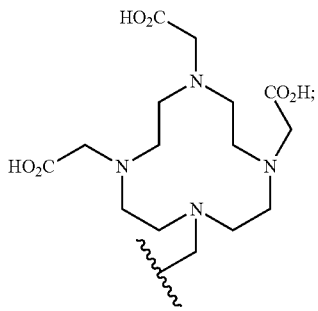 [SMILES: *CN1CCN(CC(=O)O)CCN(CC(=O)O)CCN(CC(=O)O)CC1]

e) a PET or SPECT radiotracer; or
f) a fluorophore.

11. The compound of claim 1, wherein:
L is T¹-Z-T² such that the compound is of the structure:

Q-T¹-Z-T²-X—Y wherein T¹ and T² are independently a single bond or a linking group; and
Z comprises a cleavable bond that after cleavage unmasks a functional group that provides for release of Y or X—Y.

12. The compound of claim 11, wherein:
T² comprises an electrophilic center adjacent to X; and
the functional group is a nucleophilic group that provides for intramolecular reaction at the electrophilic center to release X—Y.

13. The compound of claim 11, wherein the cleavable bond is part of the T¹-Z¹-T² backbone.

14. The compound of claim 11, wherein the cleavable bond is NOT part of the T¹-Z¹-T² backbone.

15. The compound of claim 11, wherein:

cleavage of the cleavable bond provides for spontaneous release of X—Y, via electron pair donation.

16. The compound of claim 11, wherein the compound is of the structure:

a)

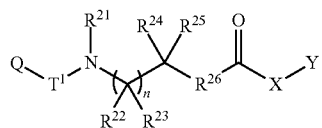

wherein n is 1, 2 or 3;

$R^{26}$ is selected from O, S and NH; and $R^{21}$, $R^{22}$, $R^{23}$, $R^{24}$ and $R^{25}$ are independently selected from hydrogen, an alkyl, an aryl and a heterocycle;

b)

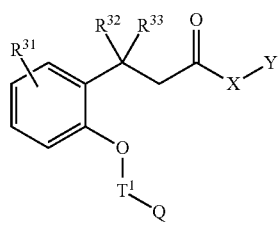

wherein $R^{31}$ is one or more groups, each $R^{31}$ independently selected from H, an alkyl, an aliphatic, an amino, an aryl, an acyl, an alkoxy, an aryloxy, an acyloxy, a carbonyl, a cyano, a halogen, hydroxyl, a heterocyclic group, a nitro, a thio, a sulfinyl, a sulfonyl, and a trifluoromethyl; and $R^{32}$ and $R^{33}$ are independently selected from hydrogen, an alkyl, an aryl and a heterocycle;

c)

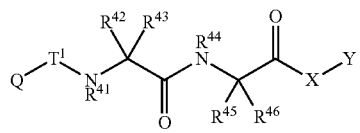

wherein $R^{41}$ and $R^{44}$ are independently selected from hydrogen, an alkyl, an aryl and a heterocycle; and $R^{42}$, $R^{43}$, $R^{45}$ and $R^{46}$ are independently selected from hydrogen an alkyl, an aryl a heterocyclic group and an amino acid sidechain; or d)

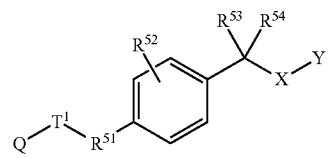

wherein $R^{51}$ is O, S or NH;

$R^{52}$ is one or more groups, each $R^{52}$ independently selected from H, an alkyl, an aliphatic, an amino, an aryl, an acyl, an alkoxy, an aryloxy, an acyloxy, a carbonyl, a cyano, a halogen, hydroxyl, a heterocyclic group, a nitro, a thio, a sulfinyl, a sulfonyl, and a trifluoromethyl; and $R^{53}$ and $R^{54}$ are independently selected from hydrogen, an alkyl, an aryl, and a heterocyclic group.

17. The compound of claim 16, wherein the compound is of the structure (a), and wherein:

n is 1;

$R^{21}$ is methyl;

$R^{22}$, $R^{23}$, $R^{24}$ and $R^{25}$ are hydrogen; and $R^{26}$ is O or NCH$_3$.

18. The compound of claim 16, wherein the compound is of the structure (a), and wherein Q is a saturated fatty acid comprising 20 carbons or less; and X—Y is a luciferin.

19. The compound of claim 16, wherein the compound is of the structure (b), and wherein:

$R^{31}$, $R^{32}$ and $R^{33}$ are hydrogen.

20. The compound of claim 16, wherein the compound is of the structure (b), and wherein:

Q is a saturated fatty acid comprising 20 carbons or less; and

X—Y is a luciferin.

21. The compound of claim 16, wherein the compound is of the structure (c), and wherein:

$R^{41}$ and $R^{44}$ are hydrogen; and $R^{42}$, $R^{43}$, $R^{45}$ and $R^{46}$ are independently selected from hydrogen and an amino acid sidechain, wherein at least one of $R^{42}$ and $R^{43}$ are hydrogen, and at least one of $R^{45}$ and $R^{46}$ are hydrogen.

22. The compound of claim 16, wherein the compound is of the structure (c), and wherein:

Q is a saturated fatty acid comprising 20 carbons or less; and

X—Y is a luciferin.

23. The compound of claim 16, wherein the compound is of the structure (d), and wherein:

$R^{51}$ is NH or O; and $R^{52}$, $R^{53}$ and $R^{54}$ are hydrogen.

24. The compound of claim 16, wherein the compound is of the structure (d), and wherein:

Q is a saturated fatty acid comprising 20 carbons or less; and

X—Y is luciferin.

25. The compound of claim 1, wherein the compound is of one of the following structures:

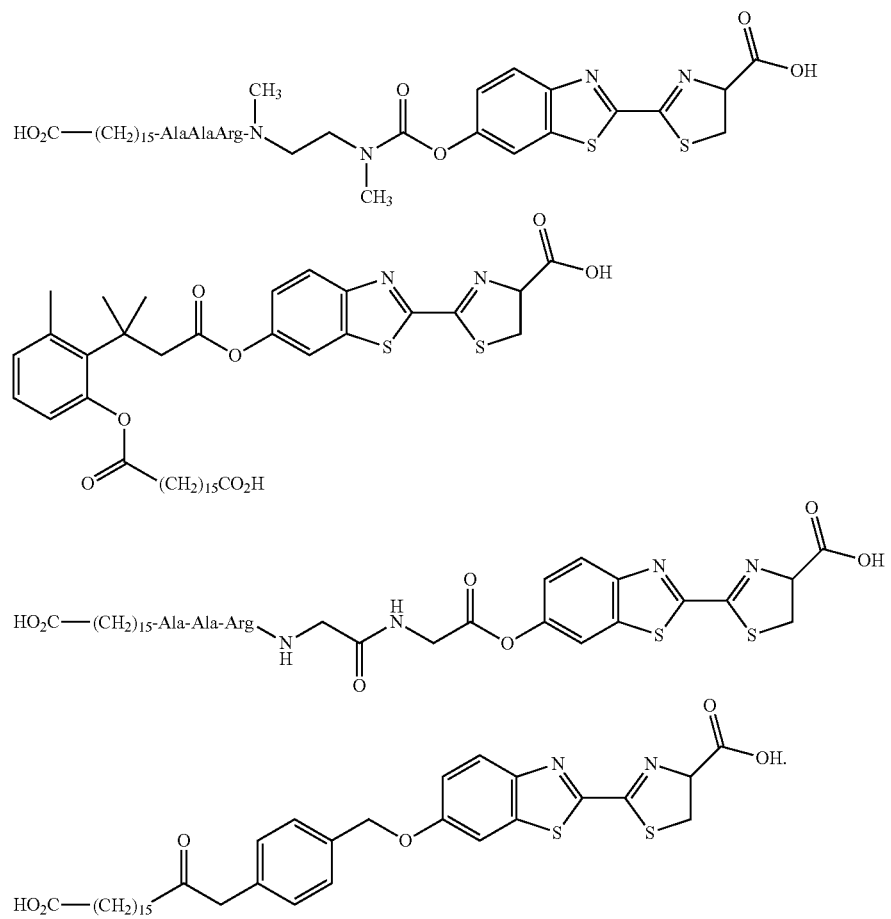
* * * * *

UNITED STATES PATENT AND TRADEMARK OFFICE
CERTIFICATE OF CORRECTION

PATENT NO. : 10,010,629 B2
APPLICATION NO. : 14/806207
DATED : July 3, 2018
INVENTOR(S) : Bertozzi et al.

Page 1 of 1

It is certified that error appears in the above-identified patent and that said Letters Patent is hereby corrected as shown below:

In the Claims

Claim 25 should read:
25. The compound of Claim 1, wherein the compound is of one of the following structures:

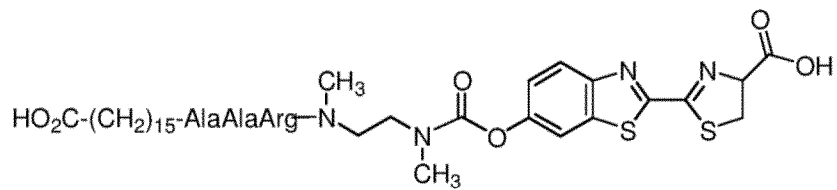

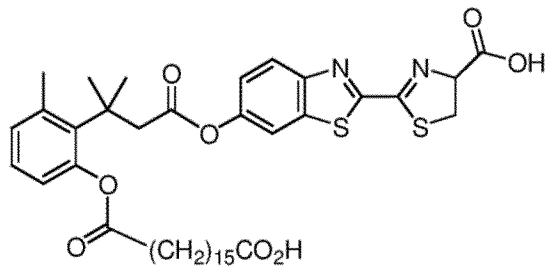

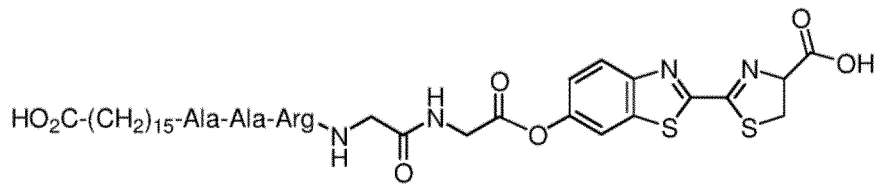

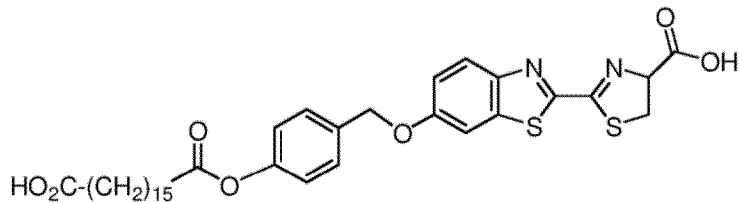

Signed and Sealed this
Sixteenth Day of October, 2018

Andrei Iancu
*Director of the United States Patent and Trademark Office*